(12) United States Patent
Masters

(10) Patent No.: US 7,662,409 B2
(45) Date of Patent: *Feb. 16, 2010

(54) PROTEIN MATRIX MATERIALS, DEVICES AND METHODS OF MAKING AND USING THEREOF

(75) Inventor: David B. Masters, Hastings, MN (US)

(73) Assignee: Gel-Del Technologies, Inc., Saint Paul, MN (US)

( * ) Notice: Subject to any disclaimer, the term of this patent is extended or adjusted under 35 U.S.C. 154(b) by 421 days.

This patent is subject to a terminal disclaimer.

(21) Appl. No.: 09/796,170

(22) Filed: Feb. 28, 2001

(65) Prior Publication Data

US 2002/0028243 A1 Mar. 7, 2002

Related U.S. Application Data

(63) Continuation-in-part of application No. 09/160,421, filed on Sep. 25, 1998, now Pat. No. 6,342,250.

(60) Provisional application No. 60/185,420, filed on Feb. 28, 2000, provisional application No. 60/222,762, filed on Aug. 3, 2000.

(51) Int. Cl.
*A61K 9/00* (2006.01)
*A61K 9/70* (2006.01)
*A61K 47/42* (2006.01)

(52) U.S. Cl. ...................... 424/484; 424/400; 424/409; 424/422; 424/423; 424/439; 424/443; 514/773; 514/774; 514/775; 514/776; 514/950; 514/953; 514/955; 514/964

(58) Field of Classification Search ................. 424/400, 424/409, 422, 423, 439, 443, 484, 489, 499, 424/500, 449; 514/952, 773, 774, 775, 776, 514/950, 953, 955, 964
See application file for complete search history.

(56) References Cited

U.S. PATENT DOCUMENTS

| | | | |
|---|---|---|---|
| 3,800,792 A | 4/1974 | McKnight | |
| 3,996,934 A | 12/1976 | Zaffaroni | |
| 4,226,848 A | 10/1980 | Nagai | |
| 4,250,163 A | 2/1981 | Nagai | |
| 4,286,592 A | 9/1981 | Chandrasekaran | |
| 4,292,299 A | 9/1981 | Suzuki | |
| 4,347,234 A | 8/1982 | Wahlig et al. | 424/426 |
| 4,438,253 A | 3/1984 | Casey | |
| 4,474,752 A | 10/1984 | Haslam et al. | 424/78 |
| 4,517,173 A | 5/1985 | Kizawa | |
| 4,518,721 A | 5/1985 | Dhabhar | |
| 4,526,938 A | 7/1985 | Churchill | |
| 4,572,832 A | 2/1986 | Kigasawa | |
| 4,652,441 A | 3/1987 | Okada | |
| 4,713,243 A | 12/1987 | Schiraldi | |
| 4,733,665 A | 3/1988 | Palmaz | |
| 4,739,762 A | 4/1988 | Palmaz | |
| 4,800,882 A | 1/1989 | Gianturco | |
| 4,801,299 A | 1/1989 | Brendel | |
| 4,849,141 A | 7/1989 | Fujioka et al. | |
| 4,894,232 A | 1/1990 | Reul | |
| 4,900,554 A | 2/1990 | Yanagibashi | |
| 4,907,336 A | 3/1990 | Gianturco | |
| 4,915,948 A | 4/1990 | Gallopo | |
| 4,917,161 A * | 4/1990 | Townsend | |
| 4,959,217 A | 9/1990 | Sanders et al. | 424/473 |
| 5,035,706 A | 7/1991 | Giantureo | |
| 5,037,392 A | 8/1991 | Hillstead | |
| 5,041,126 A | 8/1991 | Gianturco | |
| 5,041,292 A | 8/1991 | Feijen | 424/484 |
| 5,100,669 A | 3/1992 | Hyon | |
| 5,102,417 A | 4/1992 | Palmaz | |
| 5,137,729 A | 8/1992 | Kuroya | |

(Continued)

FOREIGN PATENT DOCUMENTS

| | | |
|---|---|---|
| CA | 1239755 | 8/1988 |
| CA | 1245527 | 11/1988 |
| CA | 2134997 | 11/1994 |
| CA | 2171047 | 3/1996 |
| CA | 2175722 | 5/1996 |
| CA | 2185740 | 9/1996 |
| CA | 2192520 | 12/1996 |
| EP | 0224934 | 6/1987 |
| EP | 0258780 A2 | 8/1987 |
| EP | 0485210 | 5/1992 |

(Continued)

OTHER PUBLICATIONS

Masters, et al., *Liposphere Local Anesthetic Timed-Release for Perineural Site Application*, Pharmaceutical Research, vol. 15, No. 7, 1998, pp. 1038-1045.

(Continued)

*Primary Examiner*—John Pak
(74) *Attorney, Agent, or Firm*—Fredrikson & Byron, PA

(57) ABSTRACT

The present invention relates to protein matrix materials and devices and the methods of making and using protein matrix materials and devices. More specifically the present invention relates to protein matrix materials and devices that may be utilized for various medical applications including, but not limited to, drug delivery devices for the controlled release of pharmacologically active agents, encapsulated or coated stent devices, vessels, tubular grafts, vascular grafts, wound healing devices including protein matrix suture material and meshes, skin/bone/tissue grafts, biocompatible electricity conducting matrices, clear protein matrices, protein matrix adhesion prevention barriers, cell scaffolding and other biocompatible protein matrix devices. Furthermore, the present invention relates to protein matrix materials and devices made by forming a film comprising one or more biodegradable protein materials, one or more biocompatible solvents and optionally one or more pharmacologically active agents. The film is then partially dried, rolled or otherwise shaped, and then compressed to form the desired protein matrix device.

66 Claims, 32 Drawing Sheets

U.S. PATENT DOCUMENTS

| | | | |
|---|---|---|---|
| 5,147,385 A | 9/1992 | Beck | |
| 5,188,837 A | 2/1993 | Domb | 424/450 |
| 5,192,802 A | 3/1993 | Rencher | |
| 5,282,824 A | 2/1994 | Gianturco | |
| 5,298,258 A | 3/1994 | Akemi | |
| 5,314,915 A | 5/1994 | Rencher | |
| 5,316,023 A | 5/1994 | Palmaz | |
| 5,324,775 A | 6/1994 | Ree et al. | 525/54.2 |
| 5,330,768 A | 7/1994 | Park | |
| 5,418,222 A | 5/1995 | Song | |
| 5,423,739 A * | 6/1995 | Phipps et al. | |
| 5,443,483 A | 8/1995 | Kirsch | |
| 5,447,940 A | 9/1995 | Harvey | |
| 5,573,934 A | 11/1996 | Hubbell et al. | 435/177 |
| 5,642,749 A | 7/1997 | Perryman | |
| 5,665,428 A | 9/1997 | Cha et al. | 427/213.3 |
| 5,700,478 A | 12/1997 | Biegajski | |
| 5,709,683 A | 1/1998 | Bagby | |
| RE35,748 E | 3/1998 | Luck | |
| 5,741,670 A | 4/1998 | Goetinck | |
| 5,773,019 A | 6/1998 | Ashton et al. | 424/423 |
| 5,783,214 A | 7/1998 | Royer | |
| 5,834,232 A | 11/1998 | Bishop | |
| 6,004,943 A | 12/1999 | Shi | |
| 6,248,110 B1 | 6/2001 | Reiley | |
| 6,287,765 B1 | 9/2001 | Cubicciotti | |
| 6,291,582 B1 | 9/2001 | Dordick | |
| 6,342,250 B1 | 1/2002 | Masters | |
| 6,371,988 B1 | 4/2002 | Pafford | |
| 2001/0020086 A1 | 9/2001 | Hubbell | |
| 2002/0028243 A1 | 3/2002 | Masters | |
| 2003/0007991 A1* | 1/2003 | Masters | 424/423 |
| 2005/0147690 A1* | 7/2005 | Masters et al. | 424/499 |

FOREIGN PATENT DOCUMENTS

| | | |
|---|---|---|
| EP | 0567234 A1 | 3/1993 |
| EP | 0636378 B1 | 7/1994 |
| WO | WO 93/24150 | 12/1993 |
| WO | WO 97/32543 | 9/1997 |
| WO | WO 97/32544 | 9/1997 |
| WO | 9741899 | 11/1997 |
| WO | WO 97/41803 | 11/1997 |
| WO | WO 99/32613 | 7/1999 |
| WO | 9938546 | 8/1999 |
| WO | 9949907 | 10/1999 |
| WO | 0119305 | 3/2001 |
| WO | WO 0183522 | 11/2001 |
| WO | WO 0187267 | 11/2001 |

OTHER PUBLICATIONS

Ghandehari, et al., *Genetic Engineering of Protein-Based Polymers: Potential in Controlled Drug Delivery*, Pharmaceutical Research, vol. 15, No. 6, 1998, pp. 813-815.

Masters, Letter to Joseph Cappello, Jul. 1, 1996.

Skarda, et al., *Biodegradable Hydrogel for Controlled Release of Biologically Active Macromolecules*, Journal of Bioactive and Compatible Polymers, vol. 8, Jan. 1993, pp. 24-40.

Masters, et al., *Prolonged Regional Nerve Blockade by Controlled Release of Local Anesthetic from a Biodegradable Polymer Matrix*, Anesthesiology, vol. 79, No. 2, Aug. 1993, pp. 340-346.

Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.

Davis, et al., *Chemically Cross-Linked Albumin Microspheres for the Controlled Release of Incorporated Rose Bengal After Instramuscular Injection Into Rabbits*, Journal of Controlled Release, 4 (1987) 293-302.

Lee, *J. Controlled Release*, 2, 227 (1985).

Heller, et al., *Controlled release of water-soluble macromolecules from Bioerodible Hydrogels*, Biomaterials 1983, vol. 4 October, pp. 262-266.

Dickinson, et al., *Biodegradation of a poly(α-amino acid) hydrogel. I.* In vivo, Journal of Biomedical Materials Research, vol. 15, 577-589 (1981).

Chvapil, et al., *Some Chemical and Biological Characteristics of a New Collagen-Polymer\* Compound Material*, J. Biomed. Mater. Res. vol. 3, pp. 315-331 (1969).

Fernandes, et al., *Regulation of Polymeric Implants for Site-specific Drug Delivery*, Polymeric Site-specific Pharmcotherapy, Chapter 16, pp. 424-441.

Masters, *Improvements in Perineural Local Anesthetic Block*, Abstract, CRISP—Computer Retrieval of Information on Scientific Projects, printed Sep. 22, 1998.

Cappello, et al., *Microbial Production of Structural Polymers*, (ed. Mobley), 1994 Carl Hanser Verlag, Munich, pp. 35-92.

Ranade, *Drug Delivery Systems: 3A. Role of Polymers in Drug Delivery*, J.Clin. Pharmacol 1990; 30: 10-23.

Ranade, *Drug Delivery Systems: 3A. Role of Polymers in Drug Delivery*, J.Clin. Pharmacol 1990; 30: 107-120.

Choi, et al. Implantation Biology: The Host Response and Biomedical Devices. *The Effect of Biomaterials on the Host*, CRC Press, Boca Raton 405 pages, 1994. Chapter 3, pp. 39-53.

Abstracts, *Eighth International Symposium on Recent Advances in Drug Delivery Systems*, Feb. 24, 1997, Salt Lake City, UT, pp. 36-39, 138-140.

AAPS: Annual Meeting & Exposition, *Symposia Abstracts & Biographies*, Boston, MA, Nov. 2, 1997, pp. 25-27.

Masters, Course Syllabus for Mayo Graduate Course, *Polymeric Site-Specific Drug Delivery*, Apr. 1998.

Protein Polymer Technologies: 1994 Annual Report, *BioEngineered Tissue Repair and Regeneration*.

R&D, A Cahners Publication, *BioDerived Materials*, Jun. 1990, p. 58.

Peppas, et al. *New Challenges in Biomaterials*, Science, Mar. 1994, vol. 263, pp. 1715-1720.

*American Red Cross Open to Partners for New Fibrin Sealant*, Genetic Engineering News, Mar. 1995, p. 30.

Harvey, *Utilizing Prostheses for Drug Delivery*, Implantation Biology, CRC Press, Boca Raton, 1994, pp. 329-345.

Dunn, et al., *Biomaterials Used in Orthopaedic Surgery*, Implantation Biology, CRC Press, Boca Raton, 1994, pp. 229-252.

Drug Delivery Systems (Program), Feb. 1998, San Francisco.

Masters, et al., *Prolonged Regional Nerve Blockade by Controlled Release of Local Anesthetic from a Biodegradable Polymer Matrix*, Anesthesiology, vol. 79, No. 2, 1993, pp. 340-346.

Cappello, *Protein Engineering for Biomaterials Applications*, Current Opinion in Structural Biology, 1992, 2:582-586.

Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.

Ohtani, *Three-Dimensional Organization of the Collagen Fibrillar Framework of the Human and Rat Livers*, Arch. Hist. Cytol., vol. 51, No. 5, 1988, pp. 473-788.

Sedlak, *Hyal Pharmaceutical Looks for Home Run with HIT Drug Delivery System*, Genetic Engineering News, Sep. 1, 1995, p. 16.

Pramik, *Drug Delivery Firms Focus on Controlled Release Techniques*, Genetic Engineering News, Oct. 1, 1996, pp. 1, 38, 40.

Morrow, *Companies to Take Broad Range of Approaches to Develop Rheumatoid Arthritis Therapies*, Genetic Engineering News, Jan. 15, 1997, pp. 1, 7, 9, 24.

Kelly, *Researchers Advancing Biopolymer Systems as Vehicles for Delivering Drugs*, Genetic Engineering News, May 15, 1997, pp. 1, 25, 32, 35, 36, 41.

Lewis, *New Directions in Research on Blood Substitutes*, Genetic Engineering News, Jun. 15, 1997, pp. 1, 10, 12, 20, 26, 33, 35, 36, 41.

Sedlak, *Signal Transduction Companies Moving Some Products to the Clinical Testing Environment*, Genetic Engineering News, Mar. 15, 1997, vol. 17, No. 6, pp. 1, 27, 36.

*Tissue Engineering*, Genetic Engineering News, Jan. 1998, pp. 33.

Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.

Dutton, *Tissue Engineering: Continued Growth Expected as New Techniques Evolve*, Genetic Engineering News, Apr. 1998, pp. 12, 37.

Masters, *Drug Delivery to Peripheral Nerves*, Polymeric Site-Specific Pharmacotherapy, 1994, pp. 443-455.

Langer, *1994 Whitaker Lecture: Polymers for Drug Delivery and Tissue Engineering*, Annals of Biomedical Engineering, 1995, vol. 23, pp. 101-111.

*The Biological Production of Protein Polymers and Their Use*, Trends in Biotechnology, Nov. 1990, vol. 8, No. 11.

Ratner, et al., *An Introduction to Materials in Medicine*, Biomaterials Science, 1996.

Urry, et al., *Protein-Based Materials with a Profound Range of Properties and Applications: The Elastin $\Delta T_t$ Hydrophobic Paradigm*, Protein-Based Materials, 1997, pp. 133-177.

Cappello, et al., *Genetic Engineering of Structural Protein Polymers*, Biotechnology Progress, 1990, pp. 198-202.

Anderson, *Characterization of Silk-like Proteins and Processing for Biomedical Applications*, Protein-Based Materials, 1997, pp. 371-433.

Abbott, et al., *Vascular Grafts: Characteristics and Routine Selection of Prostheses*, Vascular Surgery, a Comprehensive Review, 5$^{th}$ Edition.

Caruana, *New Drugs Spur Novel Delivery Systems*, Chemical Engineering Progress, Jul. 1997, pp. 15-19.

Cappello "In situ self-assembling protein polymer gel systems for administration, delivery, and release of drugs", Journal of controlled Release, Elsevier, Amsterdam, NL, vol. 53, No. 1-3, Apr. 30, 1998, pp. 105-117.

Cappello "The Biological Production of Protein Polymers and Their Use", Trends in Biotechnology, Elsevier, Amsterdam, vol. 8, No. 11, Nov. 1, 1990, pp. 309-311.

Foscolo "Full Length article" Biofutur. Le Mensuel Europeen DE Biotechnology, Lavoisier, Cachan, FR vol. 1997 (Oct. 1997), pp. 14-17.

Bradley "Some mechanical property considerations of reconstituted collagen for drug release supports", Biomaterials, Medical Devices, and Artificial Organs, 1997, vol. 5, No. 2, pp. 159-175.

Anderson "Morphology and Primary Crystal Structure of a Silk-like Protein Polymer Synthesized by Genetically Engineered *Escherichia Coli* Bacteria", Biopolymers, New York, NY, vol. 34, No. 8, Aug. 1, 1994, pp. 1049-1058.

Ferrari "Biosynthesis of Protein Polymers", Protein-Based Materials, 1997, pp. 37-60.

\* cited by examiner

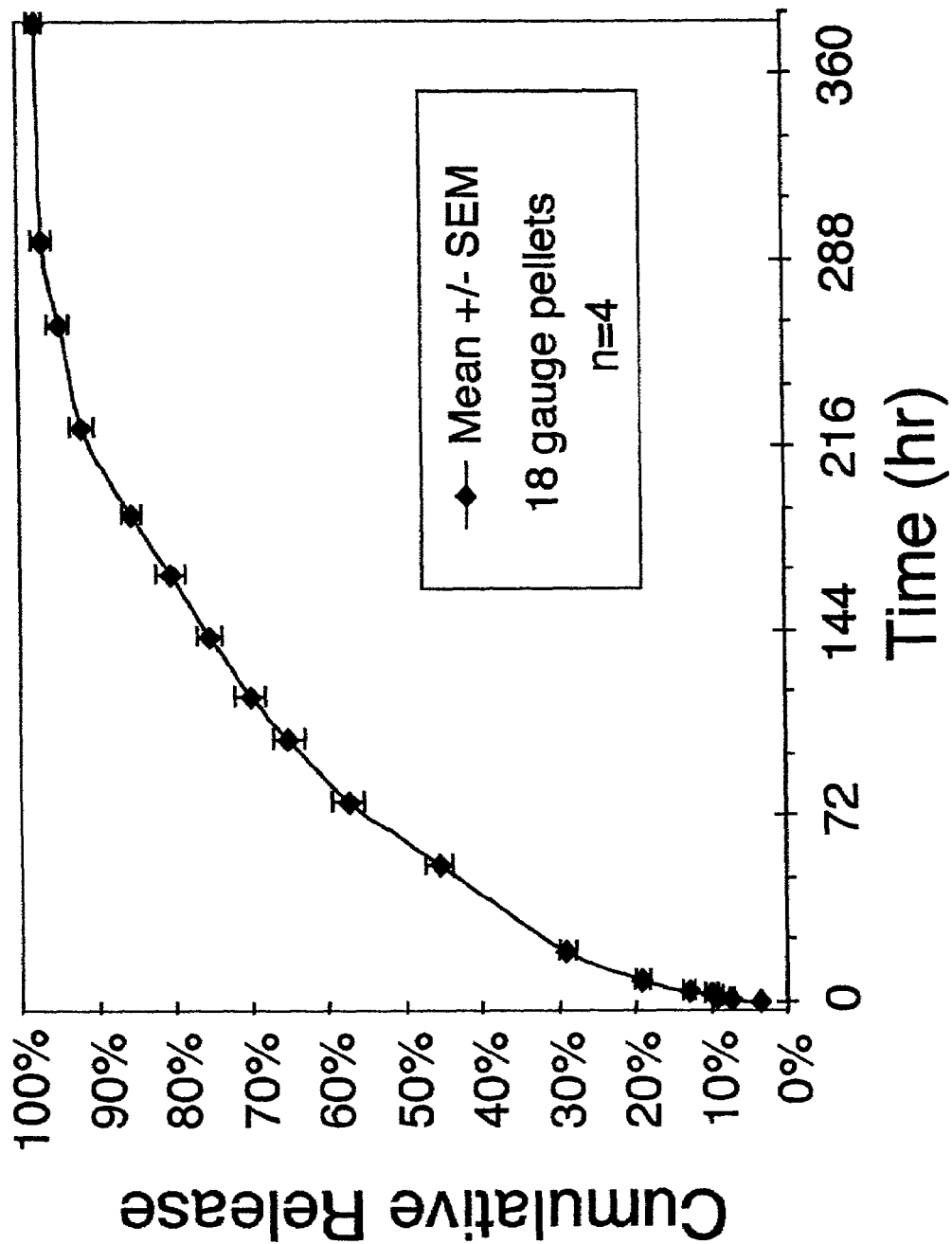

insert

```
SEQUENCE LISTING

<160> NUMBER OF SEQ ID NOS: 21

<210> SEQ ID NO 1
<211> LENGTH: 59
<212> TYPE: PRT
<213> ORGANISM: Artificial
<220> FEATURE:
<223> OTHER INFORMATION: synthetic construct similar to silk protein

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Gly Tyr
    50                  55

<210> SEQ ID NO 2
<211> LENGTH: 6
<212> TYPE: PRT
<213> ORGANISM: Artificial
<220> FEATURE:
<223> OTHER INFORMATION: seq. repeated indefinitely, synthetic construct
      similar to silk protein

<400> SEQUENCE: 2

Gly Ala Gly Ala Gly Ser
1               5

<210> SEQ ID NO 3
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing RGD sequence from fibronectin.

<400> SEQUENCE: 3

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45
```

-continued

```
Gly Ala Gly Ala Gly Ser Gly Ala Ala Val Thr Gly Arg Gly Asp Ser
 50                  55                  60

Pro Ala Ser Ala Ala Gly Tyr
 65                  70

<210> SEQ ID NO 4
<211> LENGTH: 74
<212> TYPE: PRT
<213> ORGANISM: Artificial
<220> FEATURE:
<223> OTHER INFORMATION: seq. repeated indefinitely, synthetic construct
      similar to silk protein containing sequence from laminin protein.

<400> SEQUENCE: 4

Gly Ala Gly Ala Gly Ser Gly Ala Gly Ala Gly Ser Gly Ala Gly Ala
 1               5                  10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Pro Gly Ala Ser Ile Lys Val
 50                  55                  60

Ala Val Ser Ala Gly Pro Ser Ala Gly Tyr
 65                  70

<210> SEQ ID NO 5
<211> LENGTH: 73
<212> TYPE: PRT
<213> ORGANISM: Artificial
<220> FEATURE:
<223> OTHER INFORMATION: seq. repeated indefinitely, synthetic construct
      similar to silk protein containing a different sequence from
      laminin protein.

<400> SEQUENCE: 5

Gly Ala Gly Ala Gly Ser Gly Ala Gly Ala Gly Ser Gly Ala Gly Ala
 1               5                  10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Pro Gly Ala Ser Ile Lys Val
 50                  55                  60

Ala Val Ser Gly Pro Ser Ala Gly Tyr
 65                  70

<210> SEQ ID NO 6
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing the RGD sequence from
      fibronectin.

<400> SEQUENCE: 6

Gly Ala Gly Ala Gly Ser Gly Ala Gly Ala Gly Ser Gly Ala Gly Ala
 1               5                  10                  15

Gly Ser Gly Ala Gly Ala Gly Ser Gly Ala Gly Ala Gly Ser Gly Ala
                20                  25                  30

Gly Ala Gly Ser Gly Ala Gly Ala Gly Ser Gly Ala Gly Ala Gly Ser
            35                  40                  45
```

-continued

```
Gly Ala Gly Ala Gly Ser Arg Tyr Val Val Leu Pro Arg Pro Val Cys
         50                  55                  60

Phe Glu Lys Ala Ala Gly Tyr
 65                  70

<210> SEQ ID NO 7
<211> LENGTH: 20
<212> TYPE: PRT
<213> ORGANISM: Artificial
<220> FEATURE:
<223> OTHER INFORMATION: seq. repeated indefinitely, synthetic construct
      similar to elastin protein.

<400> SEQUENCE: 7

Val Pro Gly Val Gly Val Pro Gly Val Gly Val Pro Gly Val Gly Val
 1               5                  10                  15

Pro Gly Val Gly
             20

<210> SEQ ID NO 8
<211> LENGTH: 52
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 8

Gly Val Gly Val Pro Gly Val Gly Val Pro Gly Val Gly Val Pro Gly
 1               5                  10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
             35                  40                  45

Gly Ala Gly Ser
         50

<210> SEQ ID NO 9
<211> LENGTH: 82
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 9

Gly Ala Ala Val Pro Gly Val Gly Val Pro Gly Val Gly Val Pro Gly
 1               5                  10                  15

Val Gly Val Pro Gly Val Gly Val Ala Ala Gly Tyr Gly Ala Gly Ala
                20                  25                  30

Gly Ser Gly Ala Gly Ala Gly Ser Gly Ala Gly Ala Gly Ser Gly Ala
             35                  40                  45

Gly Ala Gly Ser Gly Ala Gly Ala Gly Ser Gly Ala Gly Ala Gly Ser
         50                  55                  60

Gly Ala Gly Ala Gly Ser Gly Ala Gly Ala Gly Ser Gly Ala Gly Ala
 65                  70                  75                  80

Gly Ser

<210> SEQ ID NO 10
<211> LENGTH: 111
<212> TYPE: PRT
<213> ORGANISM: Artificial
```

```
<220> FEATURE:
<223> OTHER INFORMATION: seq. repeated indefinitely, synthetic construct
      similar to silk and elastin proteins.

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                  25                  30

Gly Ala Gly Ser Gly Ala Ala Gly Tyr Gly Ala Gly Ala Gly Ser Gly
            35                  40                  45

Ala Gly Ala Gly Ser Gly Ala Gly Ala Gly Ser Gly Ala Gly Ala Gly
        50                  55                  60

Ser Gly Ala Gly Ala Gly Ser Gly Val Gly Val Pro Gly Val Gly Val
65                  70                  75                  80

Pro Gly Val Gly Val Pro Gly Val Gly Val Pro Gly Val Gly Val Pro
                85                  90                  95

Gly Val Gly Val Pro Gly Val Gly Val Pro Gly Val Gly Val Pro
                100                 105                 110

<210> SEQ ID NO 11
<211> LENGTH: 88
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Ala Gly Ala Gly Ser Gly Ala
            35                  40                  45

Gly Ala Gly Ser Gly Ala Gly Ala Gly Ser Gly Ala Gly Ala Gly Ser
        50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser
                85

<210> SEQ ID NO 12
<211> LENGTH: 108
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 12

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Ala Gly Ala
        50                  55                  60
```

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser
            100                 105

<210> SEQ ID NO 13
<211> LENGTH: 128
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 13

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

<210> SEQ ID NO 14
<211> LENGTH: 208
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 14

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

```
Val Pro Gly Val Gly Val Pro Gly Val Gly Val Pro Gly Val Gly Val
    130                 135                 140
Pro Gly Val Gly Val Pro Gly Val Gly Val Pro Gly Val Gly Val Pro
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Gly Ala Gly Ser
        195                 200                 205

<210> SEQ ID NO 15
<211> LENGTH: 76
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 15

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Ala Gly Ala Gly Ser Gly Ala
            35                  40                  45
Gly Ala Gly Ser Gly Ala Gly Ala Gly Ser Gly Ala Gly Ala Gly Ser
        50                  55                  60
Gly Ala Gly Ala Gly Ser Gly Ala Gly Ala Gly Ser
65                  70                  75

<210> SEQ ID NO 16
<211> LENGTH: 64
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 16

Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Ala Gly Ala Gly Ser Gly Ala
            35                  40                  45
Gly Ala Gly Ser Gly Ala Gly Ala Gly Ser Gly Ala Gly Ala Gly Ser
        50                  55                  60

<210> SEQ ID NO 17
<211> LENGTH: 56
<212> TYPE: PRT
<213> ORGANISM: Artificial
<220> FEATURE:
<223> OTHER INFORMATION: seq. repeated indefinitely, synthetic construct
      similar to keratin protein.
```

-continued

```
<400> SEQUENCE: 17

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55

<210> SEQ ID NO 18
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 18

Gly Ala Pro Gly Pro Pro Gly Pro Pro Gly Pro Pro Gly Pro Pro
1               5                   10                  15

<210> SEQ ID NO 19
<211> LENGTH: 39
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 19

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 20
<211> LENGTH: 63
<212> TYPE: PRT
<213> ORGANISM: Artificial
<220> FEATURE:
<223> OTHER INFORMATION: seq. repeated indefinitely, synthetic construct
      similar to collagen protein with a cell binding domain from human
      collagen.

<400> SEQUENCE: 20

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 21
<211> LENGTH: 15
<212> TYPE: PRT
<213> ORGANISM: Artificial
```

-continued

```
<220> FEATURE:
<223> OTHER INFORMATION: seq. repeated indefinitely, synthetic construct
      similar to collagen protein.

<400> SEQUENCE: 21

Gly Ala Pro Gly Ala Pro Gly Ser Gln Gly Ala Pro Gly Leu Gln
1               5                   10                  15
```

PROTEIN MATRIX MATERIALS, DEVICES AND METHODS OF MAKING AND USING THEREOF

CROSS-REFERENCE TO RELATED APPLICATION

This application is a continuation in part of U.S. application Ser. No. 09/160,421 filed on Sep. 25, 1998 now U.S. Pat. No. 6,342,250. This patent incorporates by reference the entire contents of the previously mentioned application and furthermore claims priority to and incorporates by reference herein the entire contents of U.S. Provisional Application Ser. No. 60/185,420, filed Feb. 28, 2000, and U.S. Provisional Application Ser. No. 60/222,762, filed Aug. 3, 2000.

GOVERNMENT RIGHTS

At least a portion of the research described in this application was supported in part by Governmental funding in the form of NIH Grant No. 5R01GM51917. The Government has certain rights in the invention.

FIELD OF THE INVENTION

The present invention relates to protein matrix materials and devices and the methods of making and using protein matrix materials and devices. More specifically the present invention relates to protein matrix materials and devices that may be utilized for various medical applications including, but not limited to, drug delivery devices for the controlled release of pharmacologically active agents, encapsulated or coated stent devices, vessels, tubular grafts, vascular grafts, wound healing devices including protein matrix suture material and meshes, skin/bone/tissue grafts, clear protein matrices, protein matrix adhesion prevention barriers, cell scaffolding and other biocompatible protein matrix devices. Furthermore, the present invention relates to protein matrix materials and devices made by forming a film comprising one or more biodegradable protein materials, one or more biocompatible solvents and optionally one or more pharmacologically active agents. The film is then partially dried, rolled or otherwise shaped, and then compressed to form the desired protein matrix device.

BACKGROUND OF THE INVENTION

Protein materials are generally present in the tissues of many biological species. Therefore, the development of medical devices that utilize protein materials, which mimic and/or are biocompatible with the host tissue, have been pursued as desirable devices due to their acceptance and incorporation into such tissue. For example the utilization of protein materials to prepare drug delivery devices, tissue grafts, wound healing and other types of medical devices have been perceived as being valuable products due to their biocompatibility.

The use of dried protein, gelatins and/or hydrogels have previously been used as components for the preparation of devices for drug delivery, wound healing, tissue repair, medical device coating and the like. However, many of these previously developed devices do not offer sufficient strength, stability and support when administered to tissue environments that contain high solvent content, such as the tissue environment of the human body. Furthermore, the features of such medical devices that additionally incorporated pharmacologically active agents often provided an ineffective and uncontrollable release of such agents, thereby not providing an optimal device for controlled drug delivery.

A concern and disadvantage of such devices is the rapid dissolving or degradation of the device upon entry into an aqueous or high solvent environment. For example, gelatins and compressed dry proteins tend to rapidly disintegrate and/or lose their form when placed in an aqueous environment. Therefore, many dried or gelatin type devices do not provide optimal drug delivery and/or structural and durability characteristics. Also, gelatins often contain large amounts of water or other liquid that makes the structure fragile, non-rigid and unstable. Alternatively, dried protein devices are often very rigid, tend to be brittle and are extremely susceptible to disintegration upon contact with solvents. It is also noted that the proteins of gelatins usually denature during preparation caused by heating, thereby reducing or eliminating the beneficial characteristics of the protein. The deficiencies gelatins and dried matrices have with regards to rapid degradation and structure make such devices less than optimal for the controlled release of pharmacologically active agents, or for operating as the structural scaffolding for devices such as vessels, stents or wound healing implants.

Hydrogel-forming polymeric materials, in particular, have been found to be useful in the formulation of medical devices, such as drug delivery devices. See, e.g., Lee, *J. Controlled Release*, 2, 277 (1985). Hydrogel-forming polymers are polymers that are capable of absorbing a substantial amount of water to form elastic or inelastic gels. Many non-toxic hydrogel-forming polymers are known and are easy to formulate. Furthermore, medical devices incorporating hydrogel-forming polymers offer the flexibility of being capable of being implantable in liquid or gelled form. Once implanted, the hydrogel forming polymer absorbs water and swells. The release of a pharmacologically active agent incorporated into the device takes place through this gelled matrix via a diffusion mechanism.

However, many hydrogels, although biocompatible, are not biodegradable or are not capable of being remodeled and incorporated into the host tissue. Furthermore, most medical devices comprising of hydrogels require the use of undesirable organic solvents for their manufacture. Residual amounts of such solvents could potentially remain in the medical device, where they could cause solvent-induced toxicity in surrounding tissues or cause structural or pharmacological degradation to the pharmacologically active agents incorporated within the medical device. Finally, implanted medical devices that incorporate pharmacologically active agents in general, and such implanted medical devices comprising hydrogel-forming polymers in particular, oftentimes provide suboptimal release characteristics of the drug(s) incorporated therein. That is, typically, the release of pharmacologically active agents from an implanted medical device that includes pharmacologically active agent(s) is irregular, e.g., there is an initial burst period when the drug is released primarily from the surface of the device, followed by a second period during which little or no drug is released, and a third period during which most of the remainder of the drug is released or alternatively, the drug is released in one large burst.

It would be desirable to provide a medical device that would biocompatibly degrade and resorb into the host tissue for which it is administered. Alternatively, it would be desirable to provide a medical device that can be incorporated and remodeled by the host tissue to remain in the tissue and provide a prolonged intended function of the device. Furthermore, it would be desirable to provide improved medical devices capable of sustained, controlled local delivery of pharmacologically active agents when implanted while also being biodegradable and resorbable or alternatively capable of being incorporated and remodeled into the host tissue, such that removal of the device is not necessary. It would further be desirable to control the rate of delivery from such devices to avoid possible side effects associated with irregular delivery, e.g., high drug concentration induced tissue toxicity. Finally, it would be advantageous if such devices could be manufactured with biocompatible proteins and solvents so that the potential for residual solvent toxicity and immunogenicity is reduced.

SUMMARY OF THE INVENTION

The present invention relates to protein matrix materials and devices and the methods of making and using protein matrix materials and devices. Embodiments of the present invention may include, but are not limited to, drug delivery devices for the controlled release of pharmacologically active agents, encapsulated or coated stent devices, vessels, tubular grafts, vascular grafts, wound healing devices including protein matrix suture material and meshes, skin/bone/tissue grafts, clear protein matrices, protein matrix adhesion prevention barriers, cell scaffolding and other biocompatible protein matrix devices.

Furthermore, the present invention relates to a method of making a protein matrix material and devices by forming a coatable composition comprising one or more biocompatible protein materials, one or more biocompatible solvents and optionally one or more pharmacologically active agents. The coatable composition may also include additional polymeric materials and/or therapeutic entities that would provide additional beneficial characteristics or features to the protein matrix. The coatable composition is then coated so as to form a film (preferably a substantially planar body having opposed major surfaces and preferably having a thickness between the major surfaces of from about 0.1 millimeters to about 5 millimeters). Next, the film is at least partially dried until it is cohesive, and then formed (rolled, folded, accordion-pleated, crumpled, or otherwise shaped) into a cohesive body having a surface area less than that of the film. The cohesive body is then compressed to provide the desired protein matrix device in accordance with the present invention.

The protein matrix material is compressed to limit bulk biocompatible solvent, such as bulk or trapped water (i.e., iceberg water). The elimination of the bulk biocompatible solvent by compressing enhances the strength and durability of the matrix by initiating, stimulating and forcing additional intramolecular and intermolecular attraction between the biocompatible solvent molecules, such as hydrogen bonding activity, and also initiates, stimulates and forces intramolecular and intermolecular activity between the protein molecules, the biocompatible solvent molecules and the optional pharmacologically active agents.

The above described process has many advantages if one or more pharmacologically active agents are incorporated into the matrix. For example, the controlled release characteristics of the protein matrix provides for a higher amount of pharmacologically active agent(s) that may be incorporated into the matrix. Additionally, the pharmacologically active agent(s) is/are substantially homogeneously distributed throughout the protein matrix material or device. This homogenous distribution provides for a more systematic and consistent release of the pharmacologically active agent(s). As a result, the release characteristics of the pharmacologically active agent from the protein matrix material and/or device are enhanced.

As previously suggested, embodiments of the protein matrix devices produced utilizing the method of the present invention are capable of the sustainable, controllable local delivery of pharmacologically active agent(s), while also providing the advantage of being capable of being degraded, and preferably safely resorbed. The resorbable characteristic of various embodiments of the present invention eliminates the need for the removal of the drug delivery device from the patient once the pharmacologically active agent(s) have been completely delivered from the matrix.

Additionally, other embodiments of the present invention may be produced to remain in the patient. This may be accomplished by utilizing protein materials that do not readily degrade and resorb, but are remodeled by the host tissue, by incorporating an additional polymeric material into the protein matrix or by treating the protein matrix material with a reagent. For example, the protein matrix material may be partially or totally treated with a reagent, such as glutaraldehyde, to create crosslinking of the protein fibers in the matrix. The crosslinking of the protein material may be utilized to produce a biocompatible device that has a desired function, form or shape, such as a graft, valve or tube, and additionally may retain its form without resorbing or degrading into the patient or until the matrix has been incorporated and/or remodeled into the host tissue. Examples of protein matrix devices that would benefit from such a nonresorbable or nondegradable characteristic include, but are not limited to, stent covers, vessels, valves, tissue grafts, electronic implant coverings and other devices that need a biocompatible sustaining structure to remain in the patient. Such devices may further include one or more pharmacologically agents. The nonresorbable and nondegradable protein matrix device would still retain the systematic release of the pharmacological active agents, thereby diffusing out of the device rather than releasing upon degradation of the protein matrix material.

Whether the device is intended to be entirely resorbable or not, the method of making the protein matrix devices is generally the same. In describing the method more specifically, the method comprises the steps of preparing a coatable composition comprising one or more biodegradable protein materials, one or more biocompatible solvents and optionally one or more pharmacologically active agents. Additional biodegradable polymeric materials may be added in the preparation of the coatable composition to provide optimum features desired for the particular protein matrix device being prepared. For example, polyanhydride may be added to the protein matrix to inhibit the absorption of physiological body fluids and slows the diffusion and/or degradation of the protein matrix and/or pharmacological active agent. Preferably, the biocompatible solvent is water, dimethyl sulfoxide (DMSO), ethanol, an oil, combinations of these, or the like. More preferably, the biocompatible solvent comprises water. The coatable composition is then coated to form a film and partially dried until the coated film can be formed into a cohesive body, e.g., preferably until the film has a solvent content of from about 50% to about 70%. The film is then formed into the cohesive body, preferably with a surface area less than that of the film. The film is then shaped into a cohesive body, e.g., rolled, folded, accordion-pleated, crumpled, or otherwise shaped into a cylinder or shaped into a ball, cube and the like, preferably with a surface area less than that of the film. The cohesive body is then compressed to remove as much of the solvent as possible so that the compressed body remains cohesive, but without removing so much solvent that the compressed body becomes brittle or otherwise lacks cohesiveness. Typically, the resulting protein matrix device has a solvent content of from about 10% to about 60%, preferably from about 30% to about 50%. If desired, the compressed body may next be treated with a crosslinking reagent, such as glutaraldehyde to form a compressed body that has additional structural and nonresorbable features.

As previously suggested, by coating the aforementioned components into a film, partially drying the film, forming the film into a cohesive body and subsequently compressing the cohesive body, a protein matrix device, which includes one or more pharmacologically active agents, has a substantially homogeneous distribution of the pharmacologically active agent(s). Due to this substantially homogeneous distribution, the protein matrix devices of the present invention that include one or more pharmacologically active agents provide a sustainable and controllable release of the pharmacologically active agent(s). Furthermore, the method of the present invention utilizes biocompatible, and if selected, resorbable and biodegradable, protein materials. As a result, protein matrix devices formed in accordance with the method of the present invention may include the benefit of remaining in the patient indefinitely or simply resorbing and/or degrading into the tissue surrounding it. Finally, since the protein matrix material is biocompatible, any solvent remaining in the protein matrix device after the manufacture thereof presents a reduced, if not substantially eliminated, risk of producing undesirable side effects when implanted into a patient.

The biocompatible protein material incorporated into a device in accordance with the present invention generally comprises one or more biocompatible proteins, which preferably are a water-absorbing, biocompatible protein. Additionally, the biocompatible protein may be synthetic, genetically engineered or natural. In various embodiments of the present invention, the genetically engineered protein material comprises silklike blocks and elastinlike blocks. As previously indicated, the protein matrix device can incorporate any desired pharmacologically active agent or even a second drug delivery device, e.g., corticosteroids, opioid analgesics, neurotoxins, local anesthetics, vesicles, lipospheres, microspheres, nanospheres, enzymes, combinations of these, and the like.

It has now additionally been discovered that the sustainable release and rate controllable characteristics of the present protein matrix device may also been beneficially utilized to deliver other drug delivery devices that are either vulnerable to migration from the delivery site and/or are potentially undesirably reactive with surrounding bodily fluids or tissues. That is, not only can the protein matrix device of the present invention be beneficially utilized to deliver a pharmacologically active agent to a particular site where a therapeutic effect is desired, but also the protein matrix device of the present invention may be a "two-stage drug delivery device" utilized to deliver a second, migration-vulnerable drug delivery device comprising a pharmacologically active agent so that the second, migration-vulnerable and/or reactive drug delivery device is held in place, e.g., by the protein matrix provided by the protein matrix device of the present invention. In the instance that the two-stage protein matrix device is used to deliver a reactive drug delivery device, the protein matrix of the two stage drug delivery device reduces, if not substantially prevents the second drug delivery device from undesirably reacting with surrounding bodily tissues and/or fluids.

Thus, in another aspect, the present invention provides a protein matrix device comprising a compressed matrix comprising at least one biodegradable polymeric material and at least one such substance vulnerable to migration and/or reaction with surrounding tissues or bodily fluids, wherein said substance is substantially homogeneously distributed within the matrix. Examples of such substances include, but are not limited to, vesicles, such as liposheres or liposomes, comprising an encapsulated pharmacologically active agent, microspheres comprising an encapsulated pharmacologically active agent, combinations of these, and the like. Other examples of such substances include, but are not limited to, stents, electronic devices and other non-tissue implant that may illicit an adverse reaction from surrounding tissues.

Inasmuch as the protein matrix devices of the present invention provide the sustained release of one or more pharmacologically active agents in a rate controllable fashion, they are also capable of delivering other migration-vulnerable and/or reactive drug delivery devices and furthermore are produced in a manner that reduces, if not eliminates, the risk of residual solvent toxicity or adverse tissue reaction. Also, the protein matrix devices of the present invention provide a method of effecting a local therapeutic response in a patient in need of such treatment. Specifically, the method comprises the step of administering a protein matrix device in accordance with the present invention to the site at which a local therapeutic response is desired. Additionally, the protein matrix devices may be administered for systemic delivery of pharmacologically active agents, including oral, as well as nasal, pulmonary, subcutaneous, or any other parenteral mode of delivery. Preferably, the therapeutic response effected is an analgesic response, an anti-inflammatory response, an anesthetic response, a response preventative of an immunogenic response, an anti-coagulatory response, a genetic response, a protein assembly response, an antibacterial response, a vaccination response, combinations of these, and the like. As used herein, unless stated otherwise, all percentages are percentages based upon the total mass of the composition being described, e.g., 100% is total.

BRIEF DESCRIPTION OF THE FIGURES

The above mentioned and other advantages of the present invention, and the manner of attaining them, will become more apparent and the invention itself will be better understood by reference to the following description of the embodiments of the invention taken in conjunction with the accompanying drawing, wherein:

FIG. 17 is a graphical illustration of the in vitro release characteristics of the pharmacologically active agent, sufentanil, from a drug delivery device in accordance with the present invention.

DETAILED DESCRIPTION OF THE INVENTION

Figure 1:
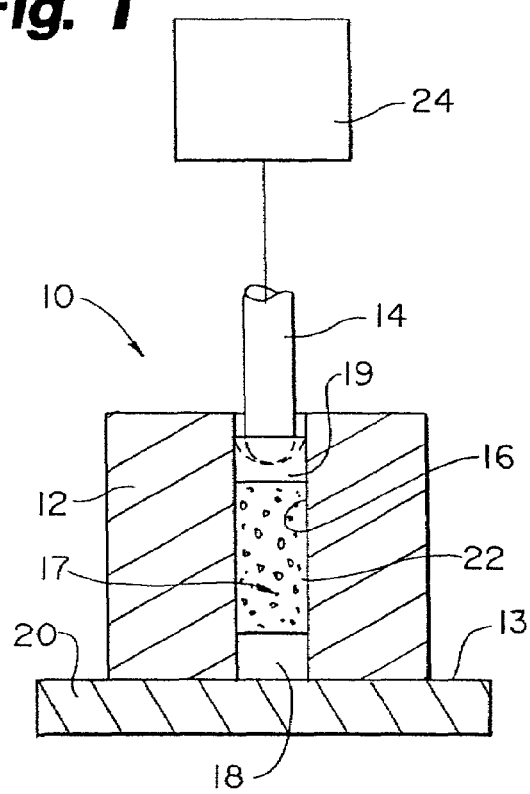
FIG. 1 is a schematic illustration, in partial cross-sectional view, of a compression molding device that may be used in the method of the present invention in a configuration prior to compression.

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention. The present invention relates to protein matrix materials and devices and a method of making such protein matrix materials and devices. More specifically, the method of the present invention involves preparing a coatable composition comprising one or more biocompatible protein materials, one or more biocompatible solvents and optionally one or more pharmacologically active agents. It is noted that additional polymeric materials and/or therapeutic entities may be included in the coatable composition to provide various beneficial features such as strength, elasticity, structure and/or any other desirable characteristics. The coatable composition is then coated to form a film that is subsequently partially dried, formed into a cohesive body, and then compressed to provide a protein matrix device in accordance with the present invention.

While not wishing to be bound by any theory, it is believed that by preparing a coatable composition from the aforementioned components, coating this composition to form a film that is subsequently partially dried, and then forming the film into a cohesive body, a relatively homogeneous distribution of the components is obtained in the cohesive body. Furthermore, when the film has dried enough so as to be cohesive unto itself, e.g., to a solvent content from about 50% to about 70%, subsequently formed into a cohesive body and then compressed many, if not all, of any distribution anomalies are removed or resolved. Therefore, when the protein matrix device includes a pharmacologically active agent, the distribution of the pharmacologically active agent is rendered substantially homogenous throughout the resulting drug delivery device.

In addition, the removal of such distribution anomalies also includes the removal of bulk or trapped biocompatible solvent, such as aqueous solutions, i.e. bulk water (i.e., iceberg water) from the matrix. For example, in aqueous solutions, proteins bind some of the water molecules very firmly and others are either very loosely bound or form islands of water molecules between loops of folded peptide chains. Because the water molecules in such an island are thought to be oriented as in ice, which is crystalline water, the islands of water in proteins are called icebergs. Furthermore, water molecules may also form bridges between the carbonyl (C=O) and imino (NH) groups of adjacent peptide chains, resulting in structures similar to those of a pleated sheet (β-sheets) but with a water molecule in the position of the hydrogen bonds of that configuration. Generally, the amount of water bound to one gram of a globular protein in solution varies from 0.2 to 0.5 grams. Much larger amounts of water are mechanically immobilized between the elongated peptide chains of fibrous proteins, such as gelatin. For example, one gram of gelatin can immobilize at room temperature 25 to 30 grams of water. It is noted that other biocompatible solvents may also interact with protein molecules to effect intra- and inter-molecular forces upon compression. The compression of the cohesive body removes the bulk solvent from the resulting protein matrix.

The protein matrix of the present invention traps biocompatible solvent molecules, such as water molecules, and forces them to interact with the protein to produce a protein-water matrix with natural physical, biological and chemical characteristics. The compression of the cohesive body eliminates the islands of water or bulk water resulting in a strengthened protein matrix structure. Furthermore, the elimination of bulk water enhances the homogenous characteristics of the protein matrix by reducing the pooling of water and spacing of the protein molecules and pharmacologically active agent molecules. Upon compression of the cohesive body, the remaining water molecules are forced to interact with most to all protein molecules and thereby add strength, structure and stability to the protein matrix. The compression forces out most of the non-structural bulk water (immobilized water) from the matrix. As previously suggested, the bulk water is extra water that is only loosely bound to the matrix. The water that interacts with the protein molecules of the protein matrix reduces and/or prevents the protein from denaturing during compression and facilitates the protein binding with the water through intra- and inter-molecular forces (i.e., ionic, dipole-dipole such as hydrogen bonding, London dispersion, hydrophobic, etc.). The enhanced binding characteristics of the protein matrix further inhibits the loss of non-bulk solvent molecules that interact with protein molecules. Experiments have indicated that a protein matrix dries to 25-45% water during overnight drying processes that would normally dry over 100 times that same amount of water if it were not in the matrix.

Furthermore, the resulting protein matrix device preferably has as little solvent as possible while still being cohesive and possessing the desired features relevant to the device's function, e.g., preferably a solvent content of from about 10% to about 60%, more preferably a solvent content of from about 30% to about 50%. It is found that when a protein matrix device of the present invention includes a pharmacologically active agent, the partial drying of the film to form a cohesive body and subsequent compressing of the cohesive body, forces more solvent out of the body, thereby producing a resulting protein matrix device that has a significantly higher concentration of pharmacologically active agent relative to other components of the device than is obtainable in protein matrix devices produced by other methods. As a result of the substantially uniform dispersion of a greater concentration of pharmacologically active agent, a sustained, controlled release of the pharmacologically active agent is achieved, while reducing the initial high concentration effects that can be associated with other devices that include pharmacologically active agents or bolus injections of pharmacologically active agents.

Reducing the solvent content has the additional effect that the resulting drug delivery device is more structurally sound, easy to handle, and thus, easy to insert or implant. Upon insertion, the cells of the tissue contacting the implanted protein matrix holds the protein matrix device substantially in the desired location. Alternatively, embodiments of the protein matrix may be held in the desired location by tissue contact, pressure, sutures, adhesives and/or tissue folds or creases. Embodiments of the protein matrix device may biodegrade and resorbs over time or retain their structural integrity.

To form the coatable composition, the biocompatible protein material(s), the biocompatible solvent(s), and optionally the pharmacologically active agent(s) may be combined in any manner. It is noted that one or more additional polymeric materials and/or therapeutic entities may be added to the coatable composition during the combination step to provide additional desirable characteristics to the coatable composition. For example, the components may simply be combined in one step, or alternatively, the biocompatible protein materials may be dissolved and/or suspended in a biocompatible solvent and an additional protein material and/or the pharmacologically active agent may be dissolved and/or suspended in the same or another biocompatible solvent and then the resulting two solutions mixed.

Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 5 millimeters, more preferably from about 0.05 millimeters to about 2 millimeters.

Initially, when the film is first coated, it is likely to be non-cohesive, fluidly-flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum, conditions of mild heating, i.e., heating to a temperature of from about 25° C. to about 50° C., or conditions of mild cooling, i.e. cooling to a temperature of from about 0° C. to about 10° C. When utilizing heat to dry the film, care should be taken to avoid denaturation or structural degradation of the pharmacologically active agent incorporated therein.

The specific solvent content at which the film becomes cohesive unto itself will depend on the individual components incorporated into the coatable composition. Generally, films that have too high of a solvent content will not be cohesive. Films that have too low of a solvent content will tend to crack, shatter, or otherwise break apart upon efforts to form them into a cohesive body. With these considerations in mind, the solvent content of a partially dried film will preferably be from about 20% to about 80%, more preferably from about 30% to about 65% and most preferably from about 35% to about 50%.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like. Preferably, the cohesive body is formed by rolling the coated film to form a cylinder.

Once so formed, the cohesive body is compressed to form a protein matrix device in accordance with the present invention. Any manually or automatically operable mechanical, pneumatic, hydraulic, or electrical molding device capable of subjecting the cohesive body to pressure is suitable for use in the method of the present invention. In the production of various embodiments of the present invention, a molding device may be utilized that is capable of applying a pressure of from about 100 pounds per square inch (psi) to about 100,000 psi for a time period of from about 2 seconds to about 48 hours. Preferably, the molding device used in the method of the present invention will be capable of applying a pressure of from about 1000 psi to about 30,000 psi for a time period of from about 10 seconds to about 60 minutes. More preferably, the molding device used in the method of the present invention will be capable of applying a pressure of from about 3,000 psi to about 25,000 psi for a time period of from about one minute to about ten minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available.

An embodiment of a compression molding device 10 suitable for use in the method of the present invention is schematically shown in FIG. 1. Compression molding device 10 is equipped with a mold body 12 in which cohesive body 22 can be subjected to pressure in order to compress and mold the cohesive body 22 into a protein matrix device in accordance with the present invention. Mold body 12 is shown supported in position on a base plate 20. More specifically, mold body 12 has provided therein a cavity 16 that preferably extends all the way through mold body 12. Within the cavity 16 a molding chamber 17 can be defined into which a cohesive body in accordance with the present invention may be inserted. The molding chamber 17 may be configured in any shape and size depending upon the shape and size of the protein matrix device. For example, the chamber may take the shape or form of a tube, heart valve, cylinder or any other desired shape. The cavity 16 may comprise a bore of any shape that may be machined, formed, cast or otherwise provided into the mold body 12. The compression molding device may optionally include one or more apertures of approximately 0.004 to 0.0001 inches for biocompatible solvent to escape the chamber 17 during compression of the cohesive body. An inner insert 18 is preferably slidably fit within cavity 16 to be positioned against one surface 13 of the base plate 20 to define the molding chamber 17 and support to cohesive body 22 when positioned within the molding chamber 17. The insert 18 may be any shape that is desired for molding the protein matrix device. For example the insert 18 may be a solid cylindrical mandrel that can form the lumen of a tube or vessel. The insert 18 is thus fixed with respect to the mold body 12 to define the inner extent of the molding chamber 17. An outer insert 19 is also preferably provided to be slidable within the cavity 16.

Outer insert 19 is used to close the molding chamber 17 of cavity 16 after the inner insert 18 and the cohesive body 22 are provided in that order within the cavity 16. The inner and outer inserts 18 and 19, respectively, can be the same or different from one another, but both are preferably slidably movable within the cavity 16. The inner and outer inserts 18 and 19, respectively, are configured to create the desired form or shape of the protein matrix device. Additionally, the inserts 18 and 19 may be shaped similarly to the shape of the cavity 16 to slide therein and are sized to effectively prevent the material of the cohesive body 22 to pass between the inserts 18 and 19 and the walls of cavity 16 when the cohesive body 22 is compressed as described below. However, the sizing may be such that moisture can escape between the outer edges of one or both inserts 18 and 19 and the surface walls of the cavity 16 from the cohesive body 22 during compression. Otherwise, other conventional or developed means can be provided to permit moisture to escape from the mold cavity during compression. For example, small openings could pass through one or both of the inserts 18 and 19 or mold body 12 which may also include one-way valve devices. Insert 18 may be eliminated so that surface 13 of base plate 20 defines the lower constraint to molding chamber 17. However, the use of insert 18 is beneficial, in that its presence facilitates easy removal of the cohesive body 22 after compression (described below) and provides a sufficiently hard surface against which the cohesive body 22 can be compressed. Moreover, by utilizing a series of differently sized and/or shaped inner inserts 18, the volume of the molding chamber can be varied, or different end features may be provided to the cohesive body 22. Outer inserts 19 can likewise be varied.

Outer insert 19 is also positioned to be advanced within cavity 16 or retracted from cavity 16 by a plunger 14. Preferably, the contacting surfaces of outer insert 19 and plunger 14 provide a cooperating alignment structure so that pressure can be evenly applied to the cohesive body 22. The plunger 14 may comprise a part of, or may be operatively connected with a pressure generation mechanism 24 that has the ability to apply pressure of the type and force necessary to achieve the results of the present invention. Conventional or developed technologies are contemplated, such as using mechanical, hydraulic, pneumatic, electrical, or other systems. Such systems can be manually or automatically operable.

Plunger 14 operates independently of mold body 12 and is operationally coupled to the pressure generation mechanism 24. Pressure generation mechanism 24 may be any pressure source capable of applying from about 100 psi to about 100,000 psi for a time period of from about 2 seconds to about 48 hours, preferably capable of applying from about 1000 psi to about 30,000 psi for a time period of from about 10 seconds to about 60 minutes, and more preferably, capable of applying a pressure of from about 3000 psi to about 25,000 psi for a time period of from about 1 minute to about 10 minutes. Preferably, plunger 14 is formulated of a material capable of translating substantially all of the pressure applied by pressure generation mechanism 24 to cohesive body 22.

Mold body 12 may be fabricated from any material capable of withstanding the pressure to be applied from pressure generation mechanism 24, e.g., high density polyethylene, Teflon®, steel, stainless steel, titanium, brass, copper, combinations of these and the like. Desirably, mold body 12 is fabricated from a material that provides low surface friction to inserts 18 and 19 and cohesive body 22. Alternatively, surfaces defining the cavity 16 may be coated with a low friction material, e.g., Teflon®), to provide such low surface friction. Due to its relatively low cost, sufficient strength and surface friction characteristics, mold body 12 is desirably fabricated from brass. Cavity 16, extending substantially through mold body 12, may be of any shape and configuration, as determined by the desired configuration of the resulting, compressed protein matrix devices. In one embodiment, cavity 16 is cylindrical. However, the shape of the cavity 16 can be configured to accommodate the shape and size of the resulting, compressed protein matrix device. As above, inserts 18 and 19 preferably fit within cavity 16 in a manner that allows moisture to escape from mold body 12, and so that inserts 18 and 19 may be easily inserted into and removed from cavity 16. Furthermore, it is preferred that inserts 18 and 19 fit within cavity 16 in a manner that provides adequate support and containment for cohesive body 22, so that, upon compression, the material of cohesive body 22 does not escape cavity 16 in a manner that would produce irregularly shaped edges on the resulting protein matrix device.

Figure 2:
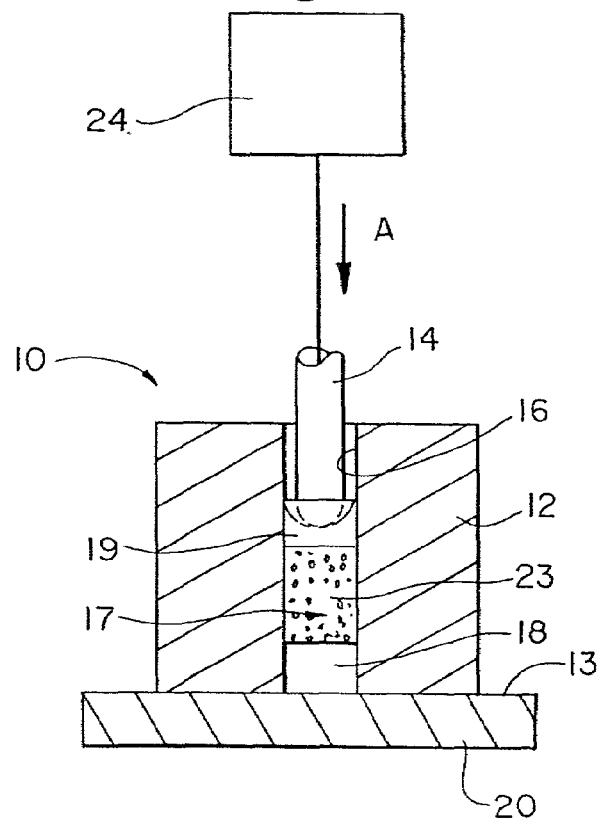
FIG. 2 is a schematic illustration, in partial cross-sectional view, of a compression molding device that may be used in the method of the present invention in a configuration during compression.

According to one procedure for using compression molding device 10 to carry out the method of the present invention, the mold body 12 is positioned as shown in FIG. 1 on the base plate 20, which itself may be supported in any manner. Then, an inner insert 18 is placed into cavity 16 followed by a cohesive body 22 to be compressed and an outer insert 19 as shown. Plunger 14 is then positioned so as to be in driving engagement with outer insert 19. Then, as schematically illustrated in FIG. 2, the pressure generation mechanism 24 is activated to move plunger 14 in the direction of arrow A to reduce the volume of the molding cavity 17 to make a compressed cohesive body 23. Pressure generation mechanism 24 applies sufficient pressure, i.e., from about 100 psi to about 100,000 psi for a time period of from about 2 seconds to about 48 hours, to plunger 14, insert 19 and cohesive body 22 against the inner insert 18, thereby driving moisture from and compressing cohesive body 22 into a protein matrix device in accordance with the present invention.

Figure 3:
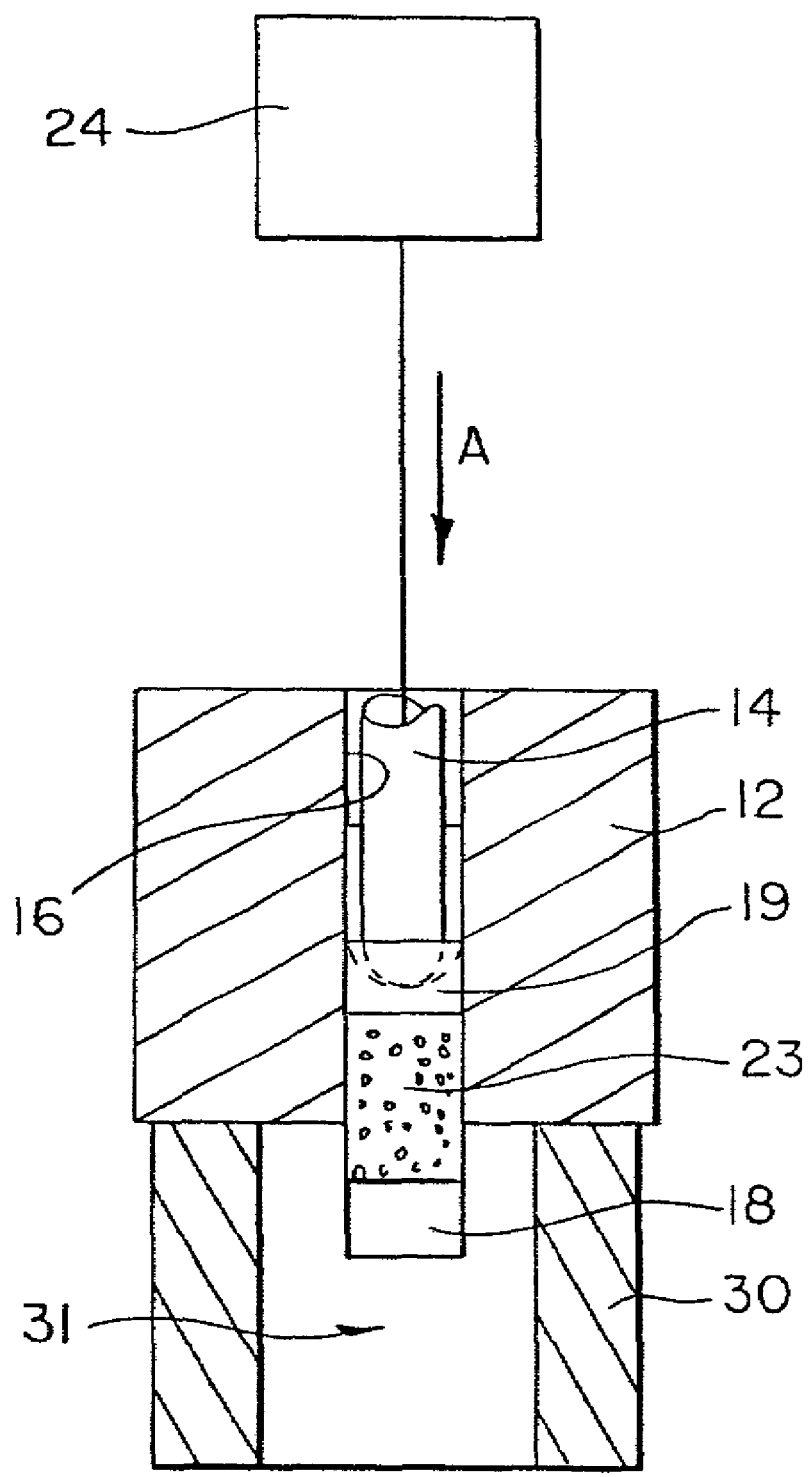
FIG. 3 is a schematic illustration, in partial cross-sectional view, of a compression molding device that may be used in the method of the present invention in a configuration during ejection.

As shown in FIG. 3, the compressed cohesive body 23 can then be ejected from the mold body 12 along with inserts 18 and 19 by positioning the mold body 12 on a support spacer 30 and further advancing the plunger 14 in the direction of arrow A by the pressure generation mechanism 24. Generally, base plate 20 is separated from the mold body 12 when ejecting the protein matrix device and inserts 18 and 19. The support spacer 30 is preferably shaped and dimensioned to provide an open volume 31 for the compressed cohesive body 23 to be easily removed. That is, when the plunger 14 is sufficiently advanced, the insert 18 and compressed cohesive body 23 can fall into the open volume 31 within the support spacer 30. After completion, the plunger 14 can be fully retracted so that the compression molding device 10 can be reconfigured for a next operation.

Any biocompatible protein material may be utilized in the protein matrix devices and corresponding methods of the present invention. Preferably, any such material will at least be water-compatible, and more preferably will be water-absorbing or hydrogel forming. Furthermore, one or more biocompatible protein materials may be incorporated into the protein matrix device of the present invention and may desirably be selected based upon their biocompatible and/or degradation properties. The combination of more than one biocompatible protein can be utilized to mimic the environment in which the device is to be administered, optimize the biofunctional characteristics, such as cell attachment and growth, nonimmuno-response reaction and/or alter the release characteristics, or duration of an included pharmacologically active agent, if a pharmacologically active agent is to be included in the device.

The biocompatible protein material comprises one or more biocompatible synthetic protein, genetically-engineered protein, natural protein or any combination thereof. In many embodiments of the present invention, the biocompatible protein material comprises a water-absorbing, biocompatible protein. In various embodiments of the present invention, the utilization of a water-absorbing biocompatible protein provides the advantage that, not only will the protein matrix device be biodegradable, but also resorbable. That is, that the metabolites of the degradation of the water-absorbing biodegradable protein may be reused by the patient's body rather than excreted. In other embodiments that do not degrade or resorb the water absorbing material provides enhanced biocompatible characteristics since the device is generally administered to environments that contain water.

The biocompatible protein utilized may either be naturally occurring, synthetic or genetically engineered. Naturally occurring protein that may be utilized in the protein matrix device of the present invention include, but are not limited to elastin, collagen, albumin, keratin, fibronectin, silk, silk fibroin, actin, myosin, fibrinogen, thrombin, aprotinin, antithrombin III and any other biocompatible natural protein. It is noted that combinations of natural proteins may be utilized to optimize desirable characteristics of the resulting protein matrix, such as strength, degradability, resorption, etc. Inasmuch as heterogeneity in molecular weight, sequence and stereochemistry can influence the function of a protein in a protein matrix device, in some embodiments of the present invention synthetic or genetically engineered proteins are preferred in that a higher degree of control can be exercised over these parameters.

Synthetic proteins are generally prepared by chemical synthesis utilizing techniques known in the art. Examples of such synthetic proteins include but are not limited to natural protein made synthetically and collagen linked GAGS like collagen-heparin, collagen-chondroitin and the like. Also, individual proteins may be chemically combined with one or more other proteins of the same or different type to produce a dimer, trimer or other multimer. A simple advantage of having a larger protein molecule is that it will make interconnections with other protein molecules to create a stronger matrix that is less susceptible to dissolving in aqueous solutions.

Additional, protein molecules can also be chemically combined to any other chemical so that the chemical does not release from the matrix. In this way, the chemical entity can provide surface modifications to the matrix or structural contributions to the matrix to produce specific characteristics. The surface modifications can enhance and/or facilitate cell attachment depending on the chemical substance or the cell type. The structural modifications can be used to facilitate or impede dissolution, enzymatic degradation or dissolution of the matrix.

Synthetic biocompatible materials may be cross-linked, linked, bonded or chemically and/or physically linked to pharmacological active agents and utilized alone or in combination with other biocompatible proteins to form the cohesive body. Examples of such cohesive body materials include, but are not limited to heparin-protein, heparin-polymer, chondroitin-protein, chondroitin-polymer, heparin-cellulose, heparin-alginate, heparin-polylactide, GAGs-collagen, heparin-collagen.

Specific examples of a particularly preferred genetically engineered proteins for use in the protein matrix devices of the present invention is that commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
| --- | --- |
| SLP 3 | [(GAGAGS)$_9$GAAGY)] |
| SLP 4 | (GAGAGS)$_n$ |
| SLP F | [(GAGAGS)$_9$GAAVTGRGDSPASAAGY]$_n$ |
| SLP L3.0 | [(GAGAGS)$_9$GAAPGASIKVAVSAGPSAGY]$_n$ |
| SLP L3.1 | [(GAGAGS)$_9$GAAPGASIKVAVSGPSAGY]$_n$ |
| SLP F9 | [(GAGAGS)$_9$RYVVLPRPVCFEKAAGY]$_n$ |
| ELP I | [(VPGVG)$_4$]$_n$ |
| SELP 0 | [(GVGVP)$_8$(GAGAGS)$_2$]$_n$ |
| SELP 1 | [GAA(VPGVG)$_4$VAAGY(GAGAGS)$_9$]$_n$ |
| SELP 2 | [(GAGAGS)$_6$GAAGY(GAGAGS)$_5$(GVGVP)$_8$]$_n$ |
| SELP 3 | [(GVGVP)$_8$(GAGAGS)$_8$]$_n$ |
| SELP 4 | [(GVGVP)$_{12}$(GAGAGS)$_8$]$_n$ |
| SELP 5 | [(GVGVP)$_{16}$(GAGAGS)$_8$]$_n$ |
| SELP 6 | [(GVGVP)$_{32}$(GAGAGS)$_8$]$_n$ |
| SELP 7 | [(GVGVP)$_8$(GAGAGS)$_6$]$_n$ |
| SELP 8 | [(GVGVP)$_8$(GAGAGS)$_4$]$_n$ |
| KLP 1.2 | [(AKLKLAEAKLELAE)$_4$]$_n$ |
| CLP 1 | [GAP(GPP)$_4$]$_n$ |
| CLP 2 | {[GAP(GPP)$_4$]$_2$GPAGPVGSP}$_n$ |
| CLP-CB | {[GAP(GPP)$_4$]$_2$(GLPGPKGDRGDAGPKGADGSPGPA)GPAGPVGSP}$_n$ |
| CLP 3 | (GAPGAPGSQGAPGLQ)$_n$ |

Repetitive amino acid sequences of selected protein polymers. SLP = silk like protein; SLPF = SLP containing the RGD sequence from fibronectin; SLPL 3/0 and SLPL 3/1 = SLP containing two difference sequences from laminin protein; ELP = elastin like protein; SELP = silk elastin like protein; CLP = collagen like protein; CLP-CB = CLP containing a cell binding domain from human collagen; KLP = keratin like protein The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The amount of the biocompatible protein component utilized in the coatable composition will be dependent upon the amount of coatable composition desired in relation to the other components of the device and the particular biocompatible protein component chosen for use in the coatable composition. Furthermore, the amount of coatable composition utilized in the coating of the film will be determinative of the size of the film, and thus, the size of the cohesive body and the resulting protein matrix device. That is, inasmuch as the amounts of the remaining components are dependent upon the amount of biocompatible protein component utilized, the amount of biocompatible protein component may be chosen based upon the aforementioned parameters.

Any biocompatible solvent may be utilized in the method and corresponding protein matrix device of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); biocompatible alcohols, such as methanol and ethanol; various acids, such as formic acid; oils, such as olive oil, peanut oil and the like; ethylene glycol, glycols; and combinations of these and the like. Preferably, the biocompatible solvent comprises water. The amount of biocompatible solvent utilized in the coatable composition will preferably be that amount sufficient to result in the composition being fluid and flowable enough to be coatable. Generally, the amount of biocompatible solvent suitable for use in the method of the present invention will range from about 50% to about 500%, preferably from about 100% to about 300% by weight, based upon the weight of the biodegradable polymeric material.

In addition to the biocompatible protein material(s) and the biocompatible solvent(s), the protein matrix devices of the present invention may optionally comprise one or more pharmacologically active agents. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the protein matrix device of the present invention include, but are not limited to, (grouped by therapeutic class):

Antidiarrhoeals such as diphenoxylate, loperamide and hyoscyamine;

Antihypertensives such as hydralazine, minoxidil, captopril, enalapril, clonidine, prazosin, debrisoquine, diazoxide, guanethidine, methyldopa, reserpine, trimethaphan;

Calcium channel blockers such as diltiazem, felodipine, amodipine, nitrendipine, nifedipine and verapamil;

Antiarrythmics such as amiodarone, flecainide, disopyramide, procainamide, mexiletene and quinidine, Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antimigraine preparations such as ergotanmine, dihydroergotamine, methysergide, pizotifen and sumatriptan;

Anticoagulants and thrombolytic agents such as warfarin, dicoumarol, low molecular weight hepafins such as enoxaparin, streptokinase and its active derivatives;

Hemostatic agents such as aprotinin, tranexarnic acid and protarnine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Neurotoxins such as capsaicin;

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, flupbenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, bipefiden, benzhexol, procyclidine and dopamine-2 agonists such as S(−)-2-(N-propyl-N-2-thi enyl ethyl amino)-5-hydroxytetralin (N-0923)-, Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketoralac, flufenisal, salsalate, triethanolamine salicylate, atninopyrine, antipyrine, oxyphenbutazone, apazone, cintazone, flufenamic acid, clonixerl, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testostero 17-(a-methyl-19-noriestosterone and fluoxymesterone;

5-alpha reductase inhibitors such as finastride, turosteride, LY-191704 and MK-306-1;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Glycosylated proteins, proteoglycans, glycosaminoglycans such as chondroitin sulfate; chitin, acetyl-glucosamine, hyaluronic acid;

Complex carbohydrates such as glucans;

Further examples of steroidal anti-inflammatory agents such as cortodoxone, fludroacetonide, fludrocortisone, difluorsone diacetate, flurandrenolone acetonide, medrysone, amcinafel, amcinafide, betamethasone and its other esters, chloroprednisone, clorcortelone, descinolone, desonide, dichlofisone, difluprednate, flucloronide, flumethasone, flunisolide, flucortolone, fluoromethalone, fluperolone, fluprednisolone, meprednisone, methylmeprednisolone, paramethasone, cortisone acetate, hydrocortisone cyclopentylpropionate, cortodoxone, flucetonide, fludrocortisone acetate, amcinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazoll;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometfine, oxytocin and gemeprost;

Prostaglandins such as alprostadil (PGEI), prostacyclin (PG12), dinoprost (prostaglandin F2-alpha) and misoprostol;

Antimicrobials including the cephalospofins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Amnioglycoides such as amikacin, gentamicin, kanamycin, neomycin, netilmicin and tobramycin;

Antifungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyfithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroan-tine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics,* 111, 223-233 (1994)), methotrexate, procarbazine, 6-mercaptopurine and mucophenolic acid;

Anorectic and weight reducing agents including dexfenflurarnine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudoephedrine;

Bronchospasm relaxants such as ephedrine, fenoterol, orciprenaline, rimiterol, salbutamol, sodium cromoglycate, cromoglycic acid and its prodrugs (described, for example, in *International Journal of Pharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramiine, clemastine, cyproheptadine, dexchlorpheniramine, diphenhydramine, diphenylamine, doxylatnine, mebhydrolin, pheniramine, tripolidine, azatadine, diphenylpyraline, methdilazine, terfenadine, astemizole, loratidine and cetirizine;

Local anaesthetics such as bupivacaine, amethocaine, lignocaine, lidocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.,* 106(5), 1096, (1996)];

Neuromuscular blocking agents such as suxamethonium, alcuronium, pancuronium, atracurium, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, and E, vitamin E acetate and vitamin E sorbate;

Allergens for desensitisation such as house, dust or mite allergens;

Nutritional agents and neutraceuticals, such as vitamins, essential amino acids and fats;

acromolecular pharmacologically active agents such as proteins, enzymes, peptides, polysaccharides (such as cellulose, amylose, dextran, chitin), nucleic acids, cells, tissues, and the like; and Keratolytics such as the alpha-hydroxy acids, glycolic acid and salicylic acid.

The protein matrix devices as disclosed herein may also be utilized for DNA delivery, either naked DNA, plasma DNA or any size DNA delivery. Also, the protein matrix may be utilized for delivery of RNA types of senses, or oligonucleotides that may be man-made portions of DNA or RNA. The protein matrix could also be utilized for delivery of compounds, as explained anywhere herein, in ovum or in embryos, as the site for implantation of the protein matrix.

The DNA, RNA or oligonucleotide may be incorporated into the protein matrix utilizing the same process of making the protein matrix device as described above. The only difference would be that the pharmacological active agents utilized would be the DNA, RNA, oligonucleotides and other such materials. In one example, a cohesive body may be produced by making a composition containing one or more biocompatible proteins, one or more biocompatible solvents and an antisense type material. In general the complementary strand of a coding sequence of DNA is the cDNA and the complementary strand of mRNA is the antisense RNA. In various embodiments of the present invention, antisense material delivered by a protein matrix device of the present invention binds with mRNA, thereby preventing it from making the protein.

Two of the advantages of including DNA, RNA or oligonucleotides in a protein matrix device is that such a device includes the benefits of local drug delivery to target cells and to have a controlled time release component so that there is an extended delivery period. An additional advantage to delivery of DNA, RNA or oligonucleotides components is that the DNA, RNA or oligonucleotides components can be released in a systematic and controlled manner over a long period of time. For example, when the antisense components bind with RNA, the body tends to cleave the RNA thereby inhibiting protein production. The biological system responds by making more RNA to make proteins. The protein matrix device provides delivery of additional antisense components in a location for an extended period of time, thereby blocking the production of the undesired protein. Also the biocompatibility of the protein matrix material enhances the binding characteristics of the anitsense components to their proper binding sites. Since the protein matrix material can be fabricated or produced to resemble the host tissue, the host cells are able to better interact with the administered protein matrix device, thereby facilitating the binding of the complimentary antisense components delivered by the protein matrix with the DNA and RNA in the host cells.

Additionally, the use of a protein matrix device in an egg or womb could be very useful for a number of applications. For example, a vaccine may be delivered in ova and then released into the animal, such as mammals, birds or reptiles, even after it's born. Also, the introduction of pharmacologically active agents that could be put in the egg or womb, could be beneficial in that it could inhibit things like bacteria or viral infection of the egg or womb during incubation and promote the healthy development of a mature animal. For example, it would be possible for the protein matrix to provide a drug delivery device for growth factors, neutraceuticals like vitamins or other agents that would help in the growth of the animal after it's hatched, or even during the stage when it is unhatched to facilitate the development of that animal. Another example would be the production of livestock, such as domestic animals like horses, cattle, pigs, sheep, dogs, cats, chickens or turkeys. If domestic animals would get a head start on growth, it may enhance their body weight, which would have a tremendous impact on the overall development of the specimen.

Finally, protein matrices may be produced in particulate forms. These forms comprise vaccine particles of all types, including protein particles containing antigen components that may be made small enough (2-10 µm) to be absorbed by immunogenic cells for enhanced immune response via subcutaneous, intraparetaneal, intravenous, intramuscular, intrathecal, epidural, intraarticular or any other administration delivery means.

The protein matrix device in accordance with the present invention, as mentioned hereinabove, may comprise an amount of a neurotoxin as the pharmacologically active agent. Specifically, inasmuch as some cases of chronic pain are the result of permanent nerve damage, in some instances it may be desirable to locally deliver an amount of a neurotoxin to the injured nerve to destroy that portion of the nerve that is the cause of the persistent, chronic pain. One example of a neurotoxin suitable for use in the present invention is capsaicin, as shown in Examples 4 and 12, hereinbelow. If a neurotoxin is to be incorporated into the protein matrix device of the present invention, it is preferred that it be incorporated in an amount ranging from about 0.001% to about 5%, more preferably, from about 0.05% to about 1% by weight, based upon the weight of the biocompatible protein component.

The protein matrix device of the present invention is particularly advantageous for the encapsulation/incorporation of macromolecular pharmacologically active agents such as proteins, enzymes, peptides, polysaccharides, nucleic acids, cells, tissues, and the like. Immobilization of macromolecular pharmacologically active agents into or onto a protein matrix device can be difficult due to the ease with which some of these macromolecular agents denature when exposed to organic solvents, some constituents present in bodily fluids or to temperatures appreciably higher than room temperature. However, since the method of the present invention, as well as the protein matrix device formed by the method utilizes biocompatible solvents such as water, DMSO or ethanol, and furthermore does not require heating, the risk of the denaturation of these types of materials is reduced. Furthermore, due to the size of these macromolecular pharmacologically active agents, these agents are encapsulated within the protein matrix upon implantation of protein matrix devices in accordance with the present invention, and thereby are protected from constituents of bodily fluids that would otherwise denature them. Thus, the protein matrix devices of the present invention allow these macromolecular agents may exert their therapeutic effects, while yet protecting them from denaturation or other structural degradation.

Examples of cells which can be utilized as the pharmacologically active agent in the protein matrix device of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastold cells, adrenal medulla cells, T-cells combinations of these, and the like. As can be seen from this partial list, cells of all types, including dermal, neural, blood, organ, stem, muscle, glandular, reproductive and immune system cells, as well as cells of all species of origin, can be encapsulated successfully by this method. Examples of proteins which can be incorporated into the protein matrix device of the present invention include, but are not limited to, hemoglobin, vasporessin, oxytocin, adrenocorticocotrophic hormone, epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies; vitamins; cofactors; retroviruses for gene therapy, combinations of these and the like.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR—52 ed (1998)—Medical Economics 1974. In consideration of these parameters, it has been found that a wide range exists in the amount of the pharmacologically active agent(s) capable of being incorporated into, and subsequently released from or alternatively allowed to exert the agent's therapeutic effects from within, the protein matrix device. More specifically, the amount of pharmacologically active agent that may be incorporated into and then either released from or active from within the protein matrix device may range from about 0.001% to about 200%, more preferably, from about 0.05% to about 100%, most preferably from about 0.1% to 70%, based on the weight of the biocompatible protein material.

In addition to the biocompatible protein material(s), the biocompatible solvent(s) and pharmacologically active agent(s), the protein matrix devices of the present invention advantageously may themselves incorporate other drug delivery devices that would otherwise typically migrate away from the desired delivery site and/or are potentially undesirably reactive with surrounding bodily fluids or tissues. Such migration is undesirable in that the therapeutic effect of the pharmacological agents encapsulated therein may occur away from the desired site, thus eliminating the advantage of localized delivery. When a protein matrix device incorporating a migration-vulnerable and/or reactive drug delivery device (hereinafter referred to as a "two-stage protein matrix device") is subsequently implanted, the migration-vulnerable and/or reactive drug delivery device(s) is/are held in place and protected by the two-stage protein matrix device. More particularly, once implanted and/or administered, the pharmacologically active agent is released by the biodegradable material of the migration-vulnerable drug delivery devices as it degrades. Then the pharmacologically active agents diffuse through the protein matrix of the two-stage protein matrix device or is released with the degradation of the protein matrix device of the present invention.

Furthermore, the compressed cohesive body of the protein matrix device reduces, if not prevents, the potential for undesirable reaction with bodily fluids or tissues that may otherwise occur upon implantation of a reactive drug delivery device without the protective protein matrix encapsulation. Examples of such drug delivery devices subject to migration for the delivery site include, but are not limited to, vesicles, e.g., liposomes, lipospheres and microspheres. Vesicles are made up of microparticles or colloidal carriers composed of lipids, carbohydrates or synthetic polymer matrices and are commonly used in liquid drug delivery devices. Vesicles, for example, have been used to deliver anesthetics using formulations with polylactic acid, lecithin, iophendylate and phosphotidyl choline and cholesterol. For a discussion of the characteristics and efficiency of drug delivery from vesicles, see, e.g., Wakiyama et al., *Chem., Pharm. Bull.,* 30, 3719 (1982) and Haynes et al., *Anesthiol,* 74, 105 (1991), the entire disclosures of which are incorporated by reference herein.

Liposomes, the most widely studied type of vesicle, can be formulated to include a wide variety of compositions and structures that are potentially non-toxic, biodegradable and non-immunogenic. Furthermore, studies are in progress to create liposomes that release more drug in response to changes in their environment, including the presence of enzymes or polycations or changes in pH. For a review of the properties and characteristics of liposomes see, e.g., Langer, *Science,* 249, 1527 (1990); and Langer, *Ann. Biomed. Eng.,* 23, 101 (1995), the entire disclosures of which are incorporated by reference herein.

Liposheres are an aqueous microdispersion of water insoluble, spherical microparticles (from about 0.2 to about 100 um in diameter), each consisting of a solid core of hydrophobic triglycerides and drug particles that are embedded with phospholipids on the surface. Liposheres are disclosed in U.S. Pat. No. 5,188,837, issued to Domb, the disclosure of which is incorporated herein by reference.

Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, e.g., U.S. Pat. Nos. 4,652,441; 5,100,669; 4,526,938; WO 93/24150; EPA 0258780 A2—U.S. Pat. Nos. 4,438,253; and 5,330,768, the entire disclosures of which are incorporated by reference herein.

Inasmuch as the migration-vulnerable and/or reactive drug delivery devices will desirably further encapsulate a pharmacologically active agent, the amount of these devices to be utilized in the two-stage protein matrix device may be determined by the dosage of the pharmacologically active agent, as determined and described hereinabove. Inasmuch as such migration-vulnerable and/or reactive drug delivery devices represent solid matter that may change the ability of the coatable composition to be coated, the amount of such devices to be included in a two-stage drug delivery device desirably ranges about 10,000 to about 1 billion, more preferably ranges from about 1 million to about 500 million, and most preferably ranges from about 200 million to about 400 million.

Additionally, the protein matrix devices formed according to the method of the present invention may optionally comprise one or more additives. Such additives may be utilized, for example, to facilitate the processing of the protein matrix devices, to stabilize the pharmacologically active agents, to facilitate the activity of the pharmacologically active agents, or to alter the release characteristics of the protein matrix device. For example, when the pharmacologically active agent is to be an enzyme, such as xanthine oxidase or superoxide dismutase, the protein matrix device may further comprise an amount of an enzyme substrate, such as xanthine, to facilitate the action of the enzyme.

Additionally, hydrophobic substances such as lipids can be incorporated into the protein matrix device to extend the duration of drug release, while hydrophilic, polar additives, such as salts and amino acids, can be added to facilitate, i.e., shorten the duration of, drug release. Exemplary hydrophobic substances include lipids, e.g., tristeafin, ethyl stearate, phosphotidycholine, polyethylene glycol (PEG); fatty acids, e.g., sebacic acid erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4. Exemplary hydrophilic additives useful to shorten the release duration of the pharmacologically active agent include but are not limited to, salts, such as sodium chloride; and amino acids, such as glutamine and glycine. If additives are to be incorporated into the coatable composition, they will preferably be included in an amount so that the desired result of the additive is exhibited. Generally, the amount of additives may vary between from about 0% to about 300%, preferably from about 100% to 200% by weight, based upon the weight of the biocompatible protein material.

Manufacturing protein matrix devices with the method of the present invention imparts many advantageous qualities to the resulting protein matrix devices. First of all, by compressing the cohesive body in such a manner, the resulting protein matrix device is substantially cohesive and durable, i.e., with a solvent content of from about 10% to about 60%, preferably of from about 30% to about 50%. Thus, administration of the protein matrix device is made easy, inasmuch as it may be easily handled to be injected or implanted. Furthermore, once implanted, the biocompatible protein material may absorb water and swell, thereby assisting the protein matrix device to stay substantially in the location where it was implanted or injected. Additionally, since the protein material may be biodegradable and the pharmacologically active agent is distributed substantially homogeneously therein, the release kinetics of the pharmacologically active agent are optimized. Indeed, the components and the amounts thereof to be utilized in the protein matrix device may be selected so as to optimize the rate of delivery of the pharmacologically active agent depending upon the desired therapeutic effect and pharmacokinetics of the chosen pharmacologically active agent.

Finally, since biocompatible solvents are used in the manufacture of the protein matrix devices, the potential for adverse tissue reactions to chemical solvents are reduced, if not substantially precluded. For all of these reasons, protein matrix devices in accordance with the present invention may advantageously be used to effect a local therapeutic result in a patient in need of such treatment. More specifically, the protein matrix devices of the present invention may be injected, implanted, or administered via oral, as well as nasal, pulmonary, subcutaneous, or any other parenteral mode of delivery. The protein matrix device may be delivered to a site within a patient to illicit a therapeutic effect either locally or systemically. Depending on the desired therapeutic effect, the protein matrix devices may be used to regenerate tissue, repair tissue, replace tissue, and deliver local and systemic therapeutic effects such as analgesia or anesthesia, or alternatively, may be used to treat specific conditions, such as coronary artery disease, heart valve failure, cornea trauma, skin wounds and other tissue specific conditions. Protein matrix devices that include pharmacologically active agents may be utilized in instances where long term, sustained, controlled release of pharmacologically active agents is desirable, such as in the treatment of surgical and post-operative pain, cancer pain, or other conditions requiring chronic pain management.

Furthermore, the protein matrix devices of the present invention may incorporate multiple pharmacologically active agents, one or more of which may be agents that are effective to suppress an immune and/or inflammatory response. In this regard, the protein matrix devices will deter, or substantially prevent the encapsulation that typically occurs when a foreign body is introduced into a host. Such encapsulation could potentially have the undesirable effect of limiting the efficacy of the protein matrix device.

Additionally, one or more polymeric materials may be included in the coatable composition to add or enhance the features of the protein matrix device. For example, one or more polymeric materials that degrades slowly may be incorporated into an embodiment of the protein matrix device that degrades in order to provide controllable release of a pharmacologically active agent that is also incorporated into the protein matrix device. That is, while a protein matrix device that includes a relatively fast-degrading protein material without a particular polymeric material will readily degrade thereby releasing drug relatively quickly upon insertion or implantation, a protein matrix device that includes a particular polymeric material, such as polyanhydride, will degrade slowly, as well as release the pharmacologically active agent(s) over a longer period of time. Examples of biodegradable and/or biocompatible polymeric materials suitable for use in the drug delivery device of the present invention include, but are not limited to epoxies, polyesters, acrylics, nylons, silicones, polyanhydride, polyurethane, polycarbonate, poly(tetrafluoroethylene) (PTFE), polycaprolactone, polyethylene oxide, polyethylene glycol, poly(vinyl chloride), polylactic acid, polyglycolic acid, polypropylene oxide, poly(akylene)glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly (amino acids), polycynoacrylates, polyphophazenes, polysulfone, polyamine, poly (amido amines), fibrin, graphite, flexible fluoropolymer, isobutyl-based, isopropyl styrene, vinyl pyrrolidone, cellulose acetate dibutyrate, silicone rubber, copolymers of these, and the like. Other materials that may be incorporated into the matrix that are not considered polymers, but provide enhanced features include, but are not limited to, ceramics, bioceramics, glasses bioglasses, glass-ceramics, resin cement, resin fill; more specifically, glass ionomer, hydroxyapatite, calcium sulfate, $Al_2O_3$, tricalcium phosphate, calcium phosphate salts, alginate and carbon. Additional other materials that may be incorporated into the matrix included alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

Embodiments of the protein matrix device may also be crosslinked by reacting the components of the protein matrix with a suitable and biocompatible crosslinking agent. Crosslinking agents include, but are not limited to glutaraldehyde, p-Azidobenzolyl Hydazide, N-5-Azido-2-nitrobenzoyloxysuccinimide, 4-[p-Azidosalicylamido]butylamine, any other suitable crosslinking agent and any combination thereof. A description and list of various crosslinking agents and a disclosure of methods of performing crosslinking steps with such agents may be found in the Pierce Endogen 2001-2002 Catalog which is hereby incorporated by reference.

Furthermore, it is noted that embodiments of the protein matrix device of the present invention may include crosslinking reagents that may initiated and thereby perform the crosslinking process by UV light activation or other radiation source, such as ultrasound or gamma ray or any other activation means.

The protein matrix may be crosslinked by utilizing methods generally known in the art. For example, a protein matrix may be partially or entirely crosslinked by exposing, contacting and/or incubating the protein matrix device with a gaseous crosslinking reagent, liquid crosslinking reagent, light or combination thereof. In one embodiment of the present invention a tube be crosslinked on the outside surface by exposing the only the outside surface to a crosslinking reagent, such as glutaraldehyde. Such a matrix has the advantages of including an outer exterior that is very pliable and possesses greater mechanical characteristics, but includes an interior surface that retains higher biofunctional features. For example, cell growth may be controlled on portions of the protein matrix by exposing such areas to crosslinking reagents while still having portions of the same protein matrix that are not crosslinked, and thereby producing biofunctional selective features for the entire protein matrix device. For example crosslinking portions of the protein matrix may be used to change, modify and/or inhibit cell attachment. It is also noted that the pharmacologically active agent may also be crosslinked, bonded and/or chemically and/or physically linked to protein matrix either partially or in totality such that the surface of the protein matrix and/or the interior of the protein matrix is linked to the protein matrix material. For example, glutaraldehyde may cross-link heparin to a single surface of a protein matrix device.

Embodiments of the present invention may include the addition of reagents to properly pH the resulting protein matrix device and thereby enhance the biocompatible characteristics of the device with the host tissue of which it is to be administered. When preparing the protein matrix device, the pH steps of the biocompatable material and biocompatable solvent occur prior to the partial drying preparation of the cohesive body. The pH steps can be started with the addition of biocompatable solvent to the protein material or to the mixture of protein material and optional biocompatible materials, or the pH steps can be started after mixing the material(s) and solvent(s) together before the cohesive body is formed. The pH steps can include the addition of drops of 0.05N to 4.0N acid or base to the solvent wetted material until the desired pH is reached as indicated by a pH meter, pH paper or any pH indicator. More preferably, the addition of drops of 0.1N-0.5 N acid or base are used. Although any acid or base may be used, the preferable acids and bases are HCl and NaOH, respectively. If known amounts of biocompatable material are used it may be possible to add acid or base to adjust the pH when the biocompatable material is first wetted, thereby allowing wetting and pH adjustments to occur in one step.

The patient to which the protein matrix device is administered may be any patient in need of a therapeutic treatment. Preferably, the patient is a mammal, reptiles and birds. More preferably, the patient is a human. Furthermore, the protein matrix device can be implanted in any location to which it is desired to effect a local therapeutic response. For example, the protein matrix device may be administered, applied, sutured, clipped, stapled, gas delivered, injected and/or implanted vaginally, in ova, in utero, in uteral, subcutaneously, near heart valves, in periodontal pockets, in the eye, in the intracranial space, next to an injured nerve, next to the spinal cord, etc. The present invention will now be further described with reference to the following non-limiting examples and the following materials and methods were employed. It is noted that any additional features presented in other embodiments described herein may be incorporated into the various embodiments being described.

Drug Delivery Devices

As previously suggested, various embodiments of the protein matrix device of the present invention may be utilized as drug delivery devices. A drug delivery device produced and administered as previously disclosed or suggested includes the biocompatible features of the components of the protein matrix and thereby reduces or prevents the undesirable effects of toxicity and adverse tissue reactions that may be found in many other types of drug delivery devices. Furthermore, the controlled release characteristics of this type of drug delivery device provides for a higher amount of pharmacologically active agent(s) that may be incorporated into the matrix. The controlled release of such a drug delivery device is partially attributed to the homogenous distribution of the pharmacologically active agent(s) throughout the drug delivery device. This homogenous distribution provides for a more systematic, sustainable and consistent release of the pharmacologically active agent(s) by gradual degradation of the matrix or diffusion of the pharmacologically active agent(s) out of the matrix. As a result, the release characteristics of the pharmacologically active agent from the protein matrix material and/or device are enhanced.

Additionally, the systematic, sustainable and consistent release of the drug delivery device may be attributed to the cohesive and interaction features present in the drug delivery device. As previously described, the protein matrix is compressed to eliminate part or all of the bulk water present in the cohesive body. This compression also compels and influences additional attracting forces amongst the protein molecules, solvent molecules and pharmacologically active agent molecules included in the matrix that would not be found if compression was not undertaken. Also other optional biocompatible materials, if included in the matrix, will be compelled and influenced to interact with the pharmacologically active agents to augment their release characteristics. This additional binding characteristic provides for a more systematic and controllable release of the pharmacologically active agents that are either trapped by interacting protein, optional biocompatible material and solvent molecules or that are also interacting with the protein, optional biocompatible material and solvent molecules themselves. Augmentation may include inhibiting or enhancing the release characteristics of the pharmacologically active agent(s). For example, a multi-layered drug delivery device may comprise alternating layers of protein matrix material that have sequential inhibiting and enhancing biocompatible materials included, thereby providing a pulsing release of pharmacologically active agents. A specific example may be utilizing glutamine in a layer as an enhancer and polyanhydride as an inhibitor. The inhibiting layer may include drugs or no drugs.

As previously suggested, embodiments of the drug delivery devices, produced and administered utilizing the methods of the present invention, are capable of the sustainable, controllable local delivery of pharmacologically active agent(s), while also providing the advantage of being capable of being degraded, and preferably safely resorbed and/or remodeled into the surrounding host tissue. The resorbable characteristic of various embodiments of the present invention eliminates the need for the removal of the drug delivery device from the patient once the pharmacologically active agent(s) have been completely delivered from the matrix. Alternatively, the drug delivery device may be produced to remain in the patient and provide a systematic and controllable diffusion of the pharmacololgically active agent(s) as described and suggested previously.

Figure 4:
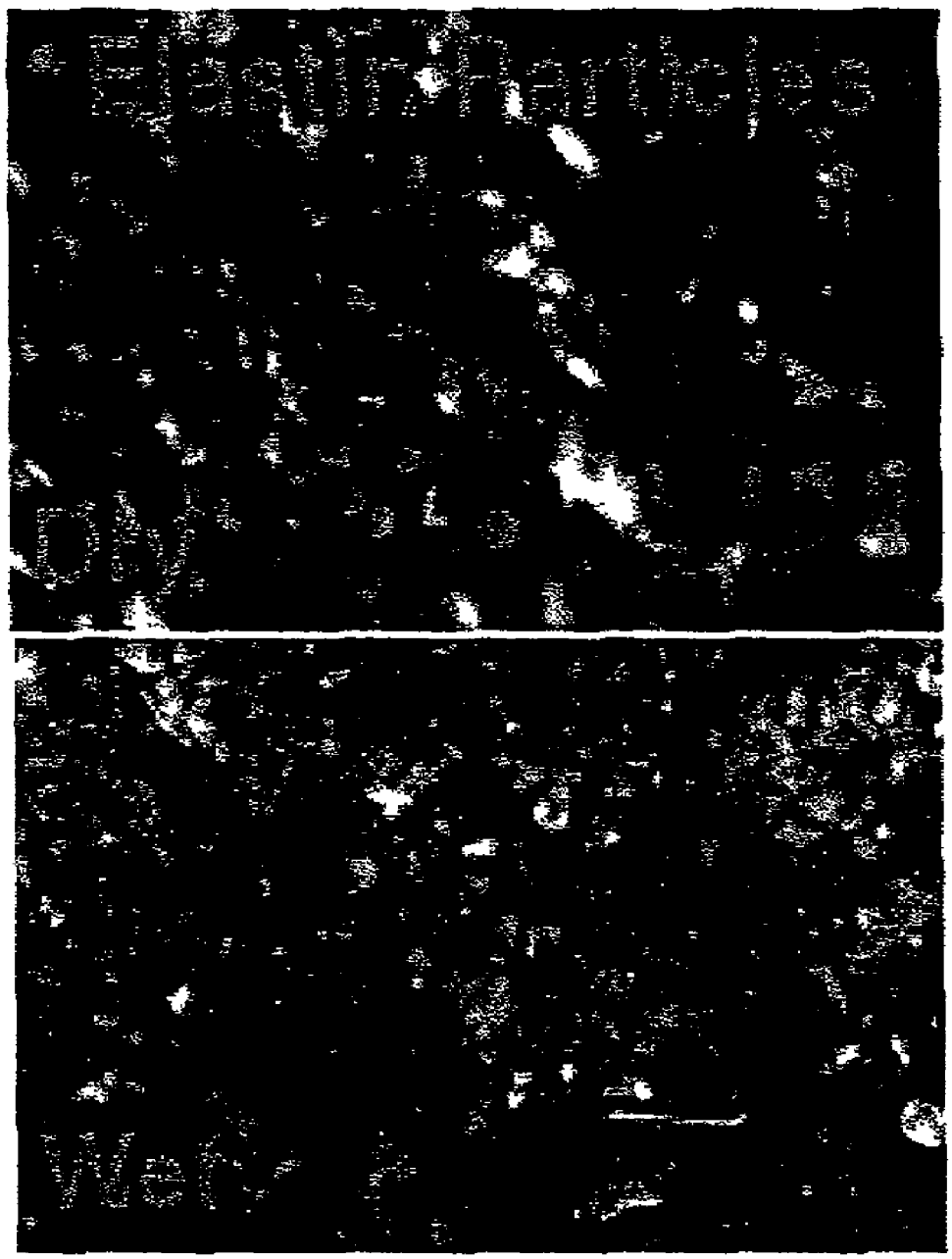
FIG. 4 depicts an embodiment of a drug delivery device of the present invention in particulate form.
Figure 5:
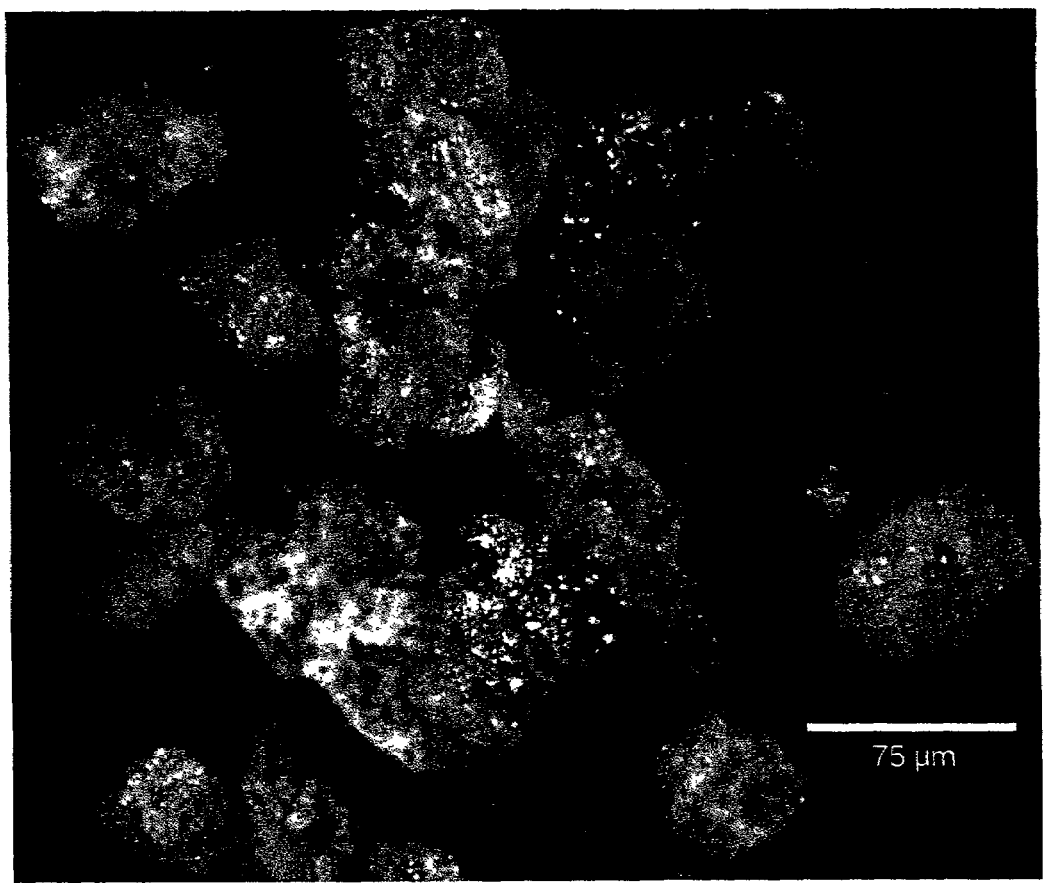
FIG. 5 depicts an embodiment of a drug delivery device of the present invention in particulate form.

The drug delivery device of present invention may be formed into any shape and size, such as a cylinder, a tube, a wafer, particles or any other shape that may optimize the delivery of the incorporated pharmacologically active agent. For example, the drug delivery device may be administered to a patient in the form of particles. FIGS. 4 and 5 depict embodiments of the drug delivery device in particulate form. Particles may be produced by pulverizing the protein matrix following the freezing of the matrix in liquid nitrogen or by utilizing other freeze fracture or particle forming techniques. A characteristic of the protein particles is that they no longer aggregate when in the particulate state. The protein matrix in particulate form may be administered to a patient in many ways, but have the proper characteristics which allow it to be a very good injectible. Furthermore, cells can be attached to particles and/or may be incorporated into the larger matrix. Any types cells such as eukaryotic cells, organ cells, such as live islets of the pancreas (for production of insulin) may be included in a particulate drug delivery device. Furthermore, the particles may include a mixture of drugs incorporated within the protein matrix and may be taken orally or through nasal mucosa, wherein the particles may interact with cellular membranes and/or body fluids.

Also, a release mechanism may be included in the protein matrix drug delivery device for the release of the one or more pharmacologically active agents. The release mechanism may be a material that encapsulates a larger drug delivery device, such as a cylinder or the release mechanism may be within a protein matrix material that includes encapsulated particles of either the drug delivery device or particles of one or more pharmacologically active agents. Additionally, the protein matrix may also encapsulate an drug delivery device larger and/or different than a particle that is covered by the release mechanism material.

Figure 5A:
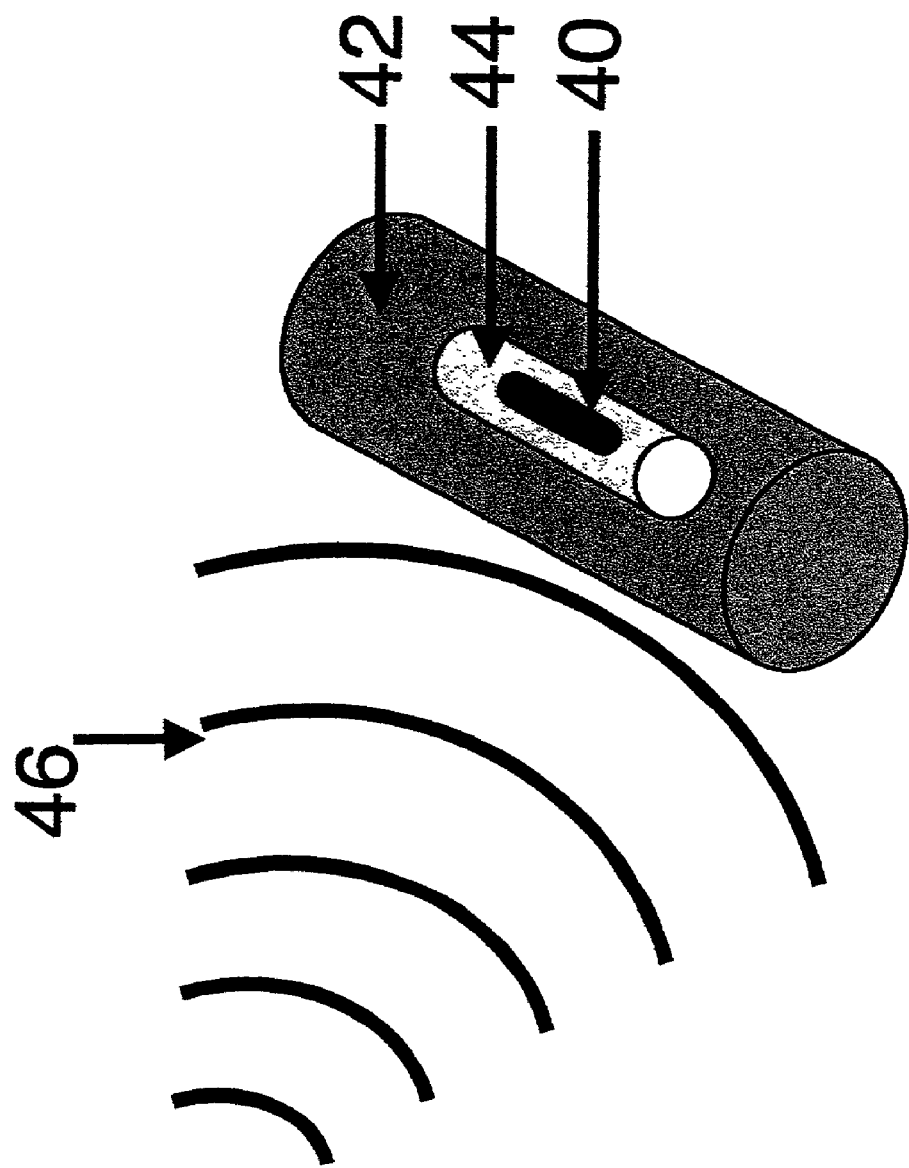

FIG. 5A depicts and embodiment of a protein matrix device that includes a release mechanism. The release mechanism 40 is positioned within a protein matrix material 42. Generally, the mechanism 40 is a material that creates a shell around the pharmacologically active agents 44 and inhibits their release until opened by some outside stimuli 46. Normally, the pharmacologically active agent can be released by a pulse of energy, radiation or a chemical reagent acting upon the encapsulating substance. For example, a drug delivery device comprising a pharmacologically active agent encapsulated in a polyanhydride coating inhibits release of the pharmacologically active agent and/or its interaction with the host tissue. In this example, the pharmacologically active agents can be released when the polyanhydride surface is contacted with an ultrasound pulse. Such an embodiment has many advantages in treating afflictions that may require an extended time period before release of the pharmacologically active agent is necessary.

Treatment of cancer or chronic pain may be examples of afflictions that may benefit from such an embodiment. The retention of chemotherapy drugs localized in an area of the patient that includes cancerous tissue may be beneficial to the long term treatment of the patient. The treatment may include implantation of a drug delivery device that includes a release mechanism in a position of the body wherein cancerous tissues has been previously resected. Upon determination that cancerous cell growth may be ongoing or occurring again, the drug deliver device can be released by some stimuli, such as a ultrasound pulse or chemical reagent. The stimuli opens the release mechanism material and allows the host tissue to interact with the pharmacologically active agents.

Encapsulated or Coated Stent Devices

Other embodiments of the present invention include the utilization of the protein matrix material in encapsulated or coated stent devices. A stent is a tube made of metal or plastic that is inserted into a vessel or passage to keep the lumen open and prevent closure due to a stricture or external compression. Stents are commonly used to keep blood vessels open in the coronary arteries, into the oesophagus for strictures or cancer, the ureter to maintain drainage from the kidneys, or the bile duct for pancreatic cancer or cholangiocarcinoma. Stents are also commonly utilized in other vascular and neural applications to keep blood vessels open and provide structural stability to the vessel. Stents are usually inserted under radiological guidance and can be inserted percutaneously. Stents are commonly made of gold or stainless steel. Gold is considered more biocompatible. However, stents constructed of any suitable material may be utilized with the protein matrix of the present invention.

Encapsulation or coating of a stent with the protein matrix material of the present invention produces a device that is more biocompatible with the host tissue than the stent device alone. Such encapsulation or coating of the stent reduces or prevents adverse immuno-response reactions to the stent device being administered and further enhances acceptance and remodeling of the device by the host tissue. Furthermore, encapsulated or coated stent devices may also include one or more pharmacologically active agents, such as heparin, within or attached to the protein matrix material that may assist in the facilitation of tissue acceptance and remodeling as well as inhibit additional adverse conditions sometimes related to implantation of stents, such as blockage of the vessel from platelet aggregation. In addition to anti-platelet aggregation drugs, anti-inflammatory agents, gene altering agents such as antisense, and other pharmacologically active agents can be administered locally to the host tissue.

Figure 6:
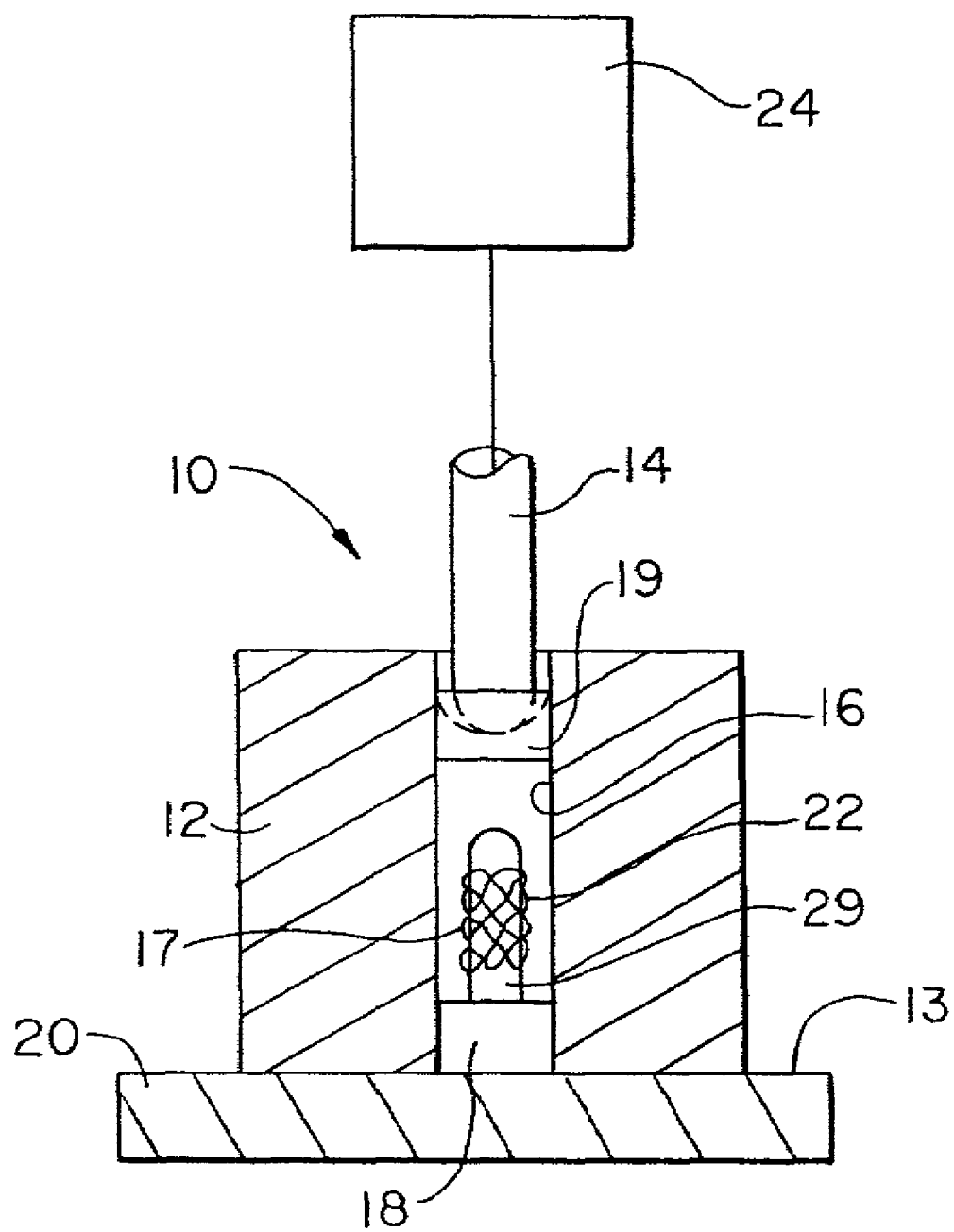
FIG. 6 is a schematic illustration, in partial cross-sectional view, of a compression molding device that may be used in the method of the present invention in wherein the inner insert includes a mandrel that that is engaged with a stent.

The protein matrix material may completely encapsulate or otherwise coat the exterior of the stent. Generally, the encapsulated or coated stent device is made in a similar process as described above. FIG. 6 depicts a compression molding device wherein the inner insert 18 includes a mandrel 29 that extends upward from the insert 18 into the chamber 17. Following preparation of the cohesive body 23, inner insert 18 is inserted into the cavity 16. A stent 32 is positioned over the mandrel 29 and the cohesive body 22 is placed in the cavity and compressed. Encapsulation or coating of the stent 32 is determined by the size of the mandrel 29 utilized in the compression molding device. A stent 32 that fits snuggly over the mandrel 29 will allow for only a coating upon the exterior of the stent 32. A smaller mandrel 29 that does provide a snug fit for the stent 32 will allow protein matrix material to move between the mandrel 29 and the stent 32 thereby creating an encapsulation of the stent 32. The encapsulated or coated stent device is then removed from the compression molding device in a similar way as described above and shown in FIG. 3. The stent device, either encapsulated or coated generally has a wall thickness of approximately 0.05 mm to 2 mm and preferably has a wall thickness of 0.15 to 0.50 mm.

As previously described additional polymeric and other biocompatible materials may be included in the protein matrix material to provide additional structural stability and durability to the encapsulated or coated stent device. Also, other structural materials, such as proteoglycans, can be used in this process to add greater tissue imitation and biocompatibility. The proteoglycans can replace or be mixed with the protein material in the production of the protein matrix material.

Figure 7:
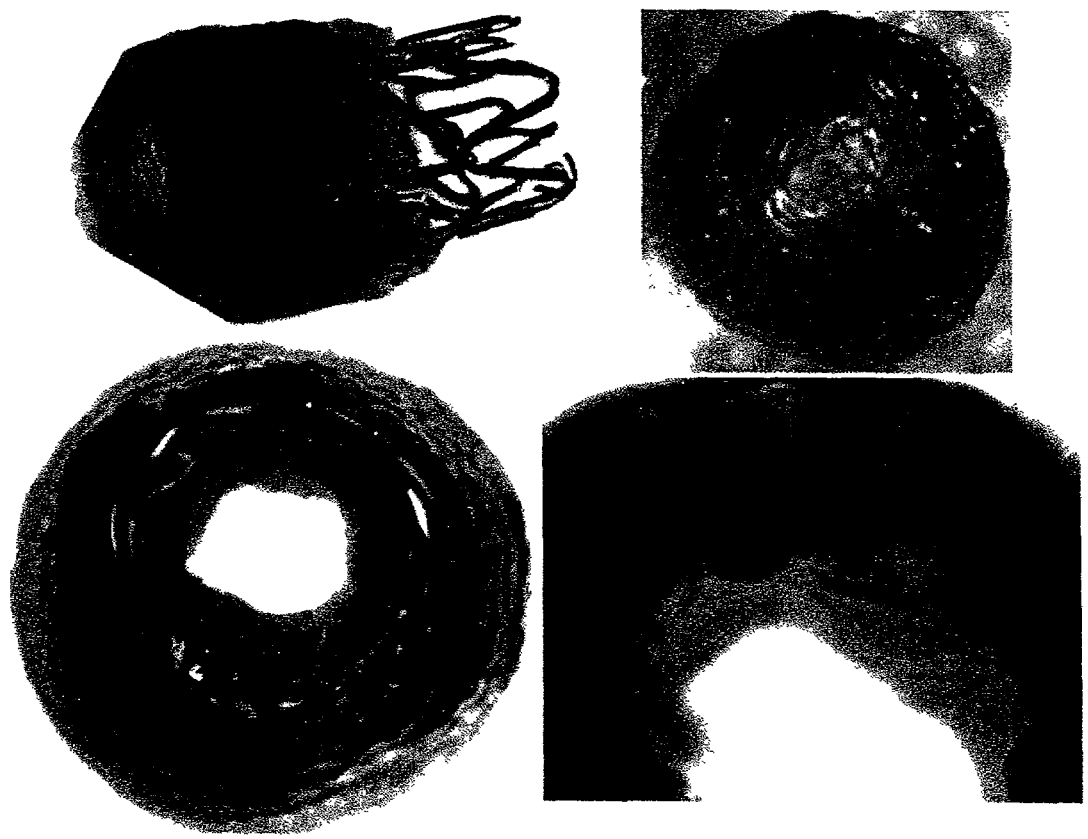
FIG. 7 depicts various views of an embodiment of the present invention formulated as a tubular graft.

Additionally, the protein matrix material included in the encapsulated or coated stent cover may be cross-linked to provide additional desirable features such as the inhibition of cell growth or to provide additional structural durability and stability. For example the protein matrix material of the encapsulated or coated stent device may be crosslinked by contacting the material with a chemical reagent, such as glutaraldehyde, or other type of crosslinking reagent. FIG. 7 depicts various views of a tube made of elastin which has been crosslinked by being exposed to a 1% solution of glutaraldehyde for 5 minutes.

Figure 8:
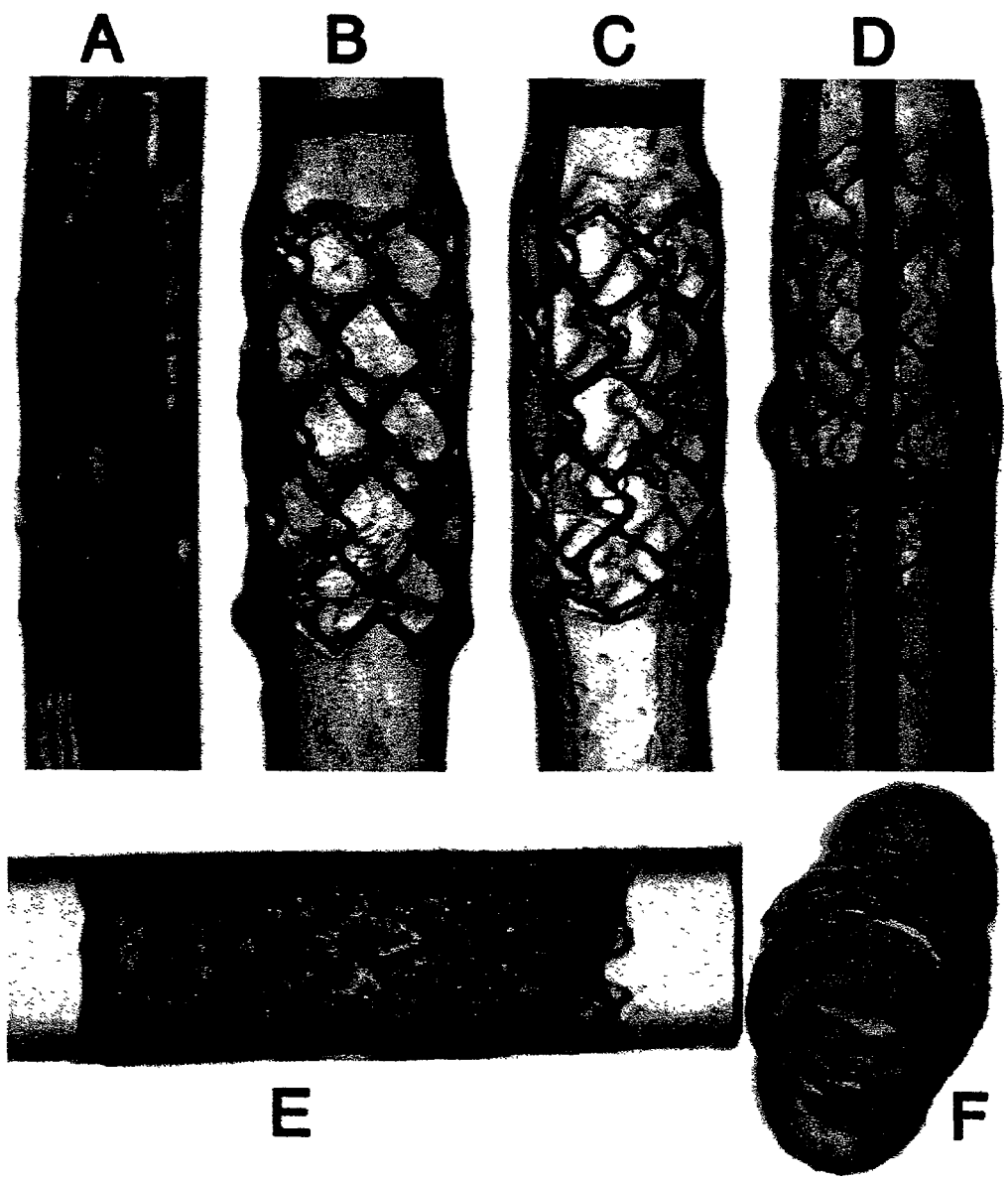
FIG. 8 depicts various embodiments of an encapsulated stent device with a silastic tube and/or angioplasty balloon inserted therein.
Figure 9:
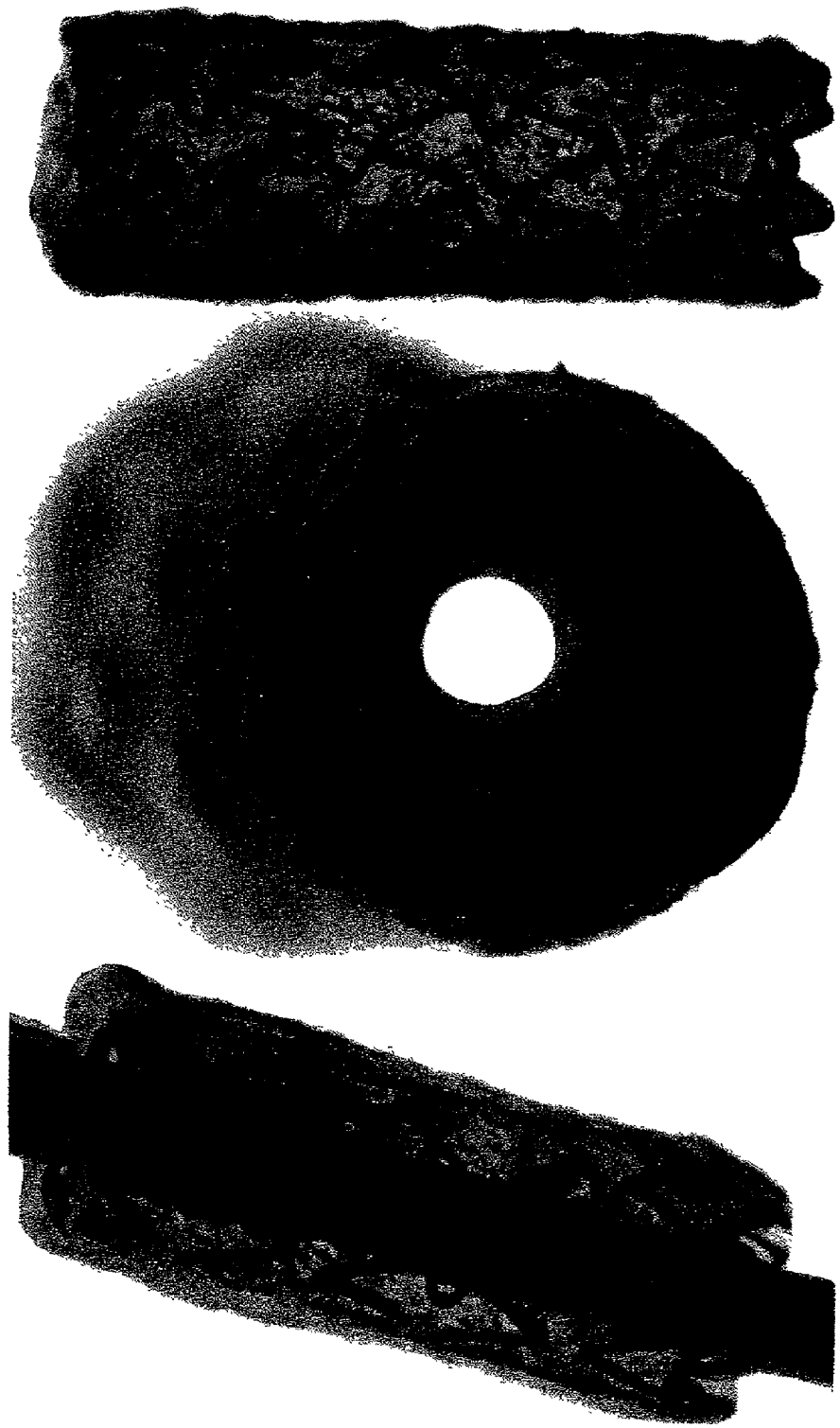
FIG. 9 depicts various embodiments of an encapsulated stent device.

FIGS. 8 and 9 depict additional embodiments of encapsulated and coated stents. FIG. 8 depicts an encapsulated stent device including a protein matrix material comprising a 1:1 ratio of elastin to albumen (bovine serum albumin). FIG. 8 further depicts the encapsulated stent device inserted within a silastic tube. The encapsulated stent device in FIG. 8 is further shown being expanded by insertion and expansion of an angioplasty balloon within the interior of the device. Furthermore, the stent device of FIG. 8 illustrates that the protein matrix material remains engaged to the stent struts and does not separate from the stent after the stent device is opened by the angioplasty balloon.

Other embodiments of the stent device of the present invention may be produced by preparing a stent device that includes a ratio of 2:1:2 collagen to elastin to albumen, 4:1 collagen to elastin, 1:4:15 heparin to elastin to collagen, 1:4:15 condroitin to elastin to collagen. Each embodiment depicted in the Figures illustrates the uniform distribution of the protein matrix material around the stent and also depicts the strength and durability of the stent after expansion by a balloon.

Furthermore, the stent devices can also be used to incorporate peptides and other materials that have the ability to inhibit cell migration. A disadvantage of utilizing stents in a vessel is that the expansion of the vessel upon insertion of stent weakens the vessel and may allow smooth muscle cells to enter into the vessels thereby occluding or restinosing the vessel. Occlusion of the vessel and restinosis can be treated by utilizing the stent device and vessels or tube grafts of the present invention. Vessels and tubular grafts will be explained later in the text of this disclosure. It is important to note that inserting a stent with or without drugs can prevent such breakdown and growth of cells into the diseased or damaged vessel.

Tissue Grafts

Additional embodiments of the present invention include the utilization of the protein matrix material in producing tissue grafts such as vessels; tubular grafts like tracheal tubes, bronchial tubes, catheter functioning tubes, lung, gastrointestinal segments; clear matrix grafts; valves; cartilage; tendons; ligaments skin; pancreatic implant devices; and other types of tissue that relate to the heart, brain, nerve, spinal cord, nasal, liver, muscle, thyroid, adrenal, pancreas, and surrounding tissue such as connective tissue, pericardium and peritoneum. It is noted that a tube does not necessarily have to be cylindrical in shape, but is generally found in that configuration.

Figure 10:
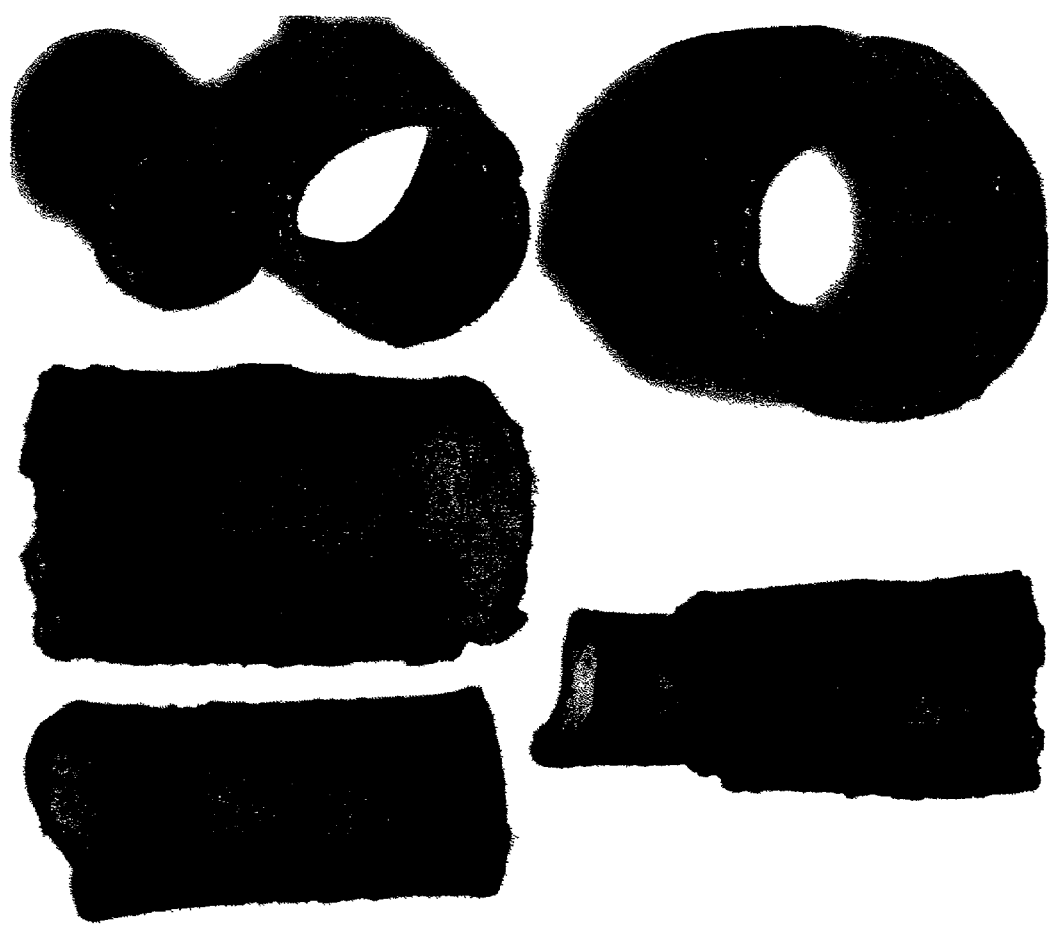
FIG. 10 depicts various views of a multi-layer vessel.

Vessels and tubular grafts may be synthesized utilizing the protein matrix material. Generally, a vessel is a tubular graft made of the protein matrix material that includes the growth of cells on and/or within the matrix. For example, vessels may be produced utilizing the protein matrix material by growing endothelial cells on the inside of the protein matrix tube and smooth muscle cells on the outside of the tube. Alternatively, a multi-layered vessel may be created with two or more separate tubes, wherein a smaller tube with endothelial cells grown on the inside of the tube is inserted into a larger tube with smooth muscle cells grown on the outside of the tube. Both tubes may then be crosslinked on the surface that does not include cell growth to add further durability and stability to the vessel. Additional tubular layers may be included in the vessel that may or may not include the growth of cells on the surfaces or within the protein matrix. FIG. 10 depicts various views of a multi-layer vessel by illustrating the multi-layer vessel the various tubes inserted within each other and also side by side. These layers may also contain pharmacologically active agents and/or more structural components, such as polymeric materials or stents. The layers will generally stay in position through adhesives, fasteners like sutures, cell interaction, pressure fitting, crosslinking, protein matrix intermolecular forces and other layer alignment means and may adhere or may not adhere to each other. It is also noted that layers that include cell growth may also include pharmacologically active agents.

Figure 11A:
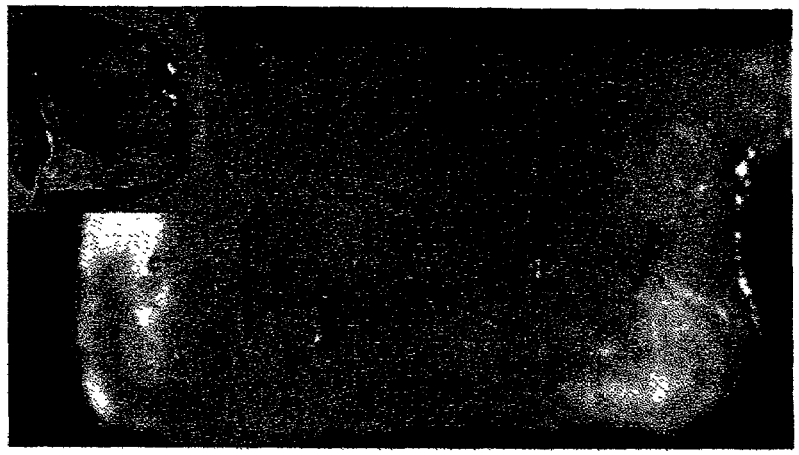
FIG. 11 depicts an embodiment of a tubular graft that illustrates the capability, compliancy and capacity of the protein matrix material to accept sutures and reform to its original shape.
Figure 11B:
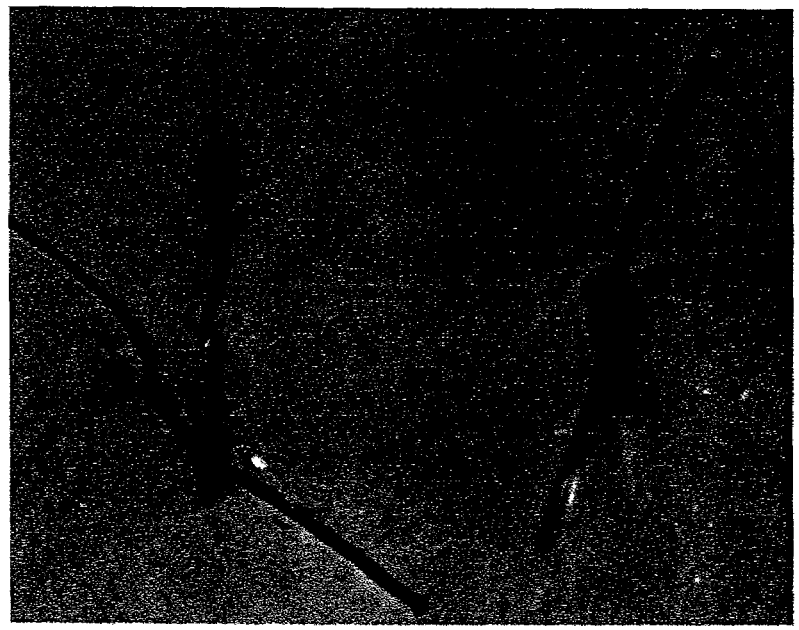

Once prepared the tubular graft or vessel may be administered to the patient as a replacement to a damaged vessel or as a scaffolding device that can be inserted into or mounted around the damaged vessel. Vascular tubes, known as STUNTS (Support Tube Using New Technology Stent) can be used for placement within a blood vessel. (A support tube without a wire stent that can "stunt" the growth of smooth muscle cells into the lumen of the vessel to prevent restenosis.) Embodiments of the tubular grafts have form memory and will reform if cut or severed back to its original form and shape. FIG. 11 depicts an embodiment of the present invention that illustrates the capability, compliancy and capacity of the protein matrix material to accept sutures and reform to its original shape.

A vessel structure of the present invention will meet the mechanical and histological requirements of a blood vessel, while providing the biological and biochemical functions that are necessary for its success. One embodiment that ensures mechanical integrity and biological compatibility is a scaffold comprising collagen and elastin. These proteins are the primary components of a typical arterial wall. This will create the natural environment for the endothelial cells, while providing the structural characteristics of these proteins. Endothelialization of the cylindrical matrices will provide the critical hemocompatibility, while also providing the thrombolytic characteristics. This feature will allow for the creation of small-diameter vascular grafts with a reduction in thrombosis. Embodiments of the tubular structure will have a diameter of approximately 2-4 mm due to the small-diameters of native coronary arteries. Due to the prevalence of coronary disease and the need for effective treatments, the proposed tubular structure would be embraced as a compatible vascular graft.

Additionally, the tubular grafts prepared by using the methods of the present invention can provide the similar function as the previously described encapsulated or coated stent devices. The difference between the tubes and the stent device would be the elimination of the stent. The tubes of the present invention have been shown to provide sufficient strength and durability and may be utilized as a scaffolding in diseased vessels thereby inhibiting the narrowing of vessels in all regions of the patient, such as the cardiovascular and neural regions. The vessels or tubular grafts may also be inserted under radiological guidance and can be inserted percutaneously. Similar to the encapsulated or coated stent devices, the vessels or tubular grafts that include the protein matrix material of the present invention are biocompatible and reduce or prevent immunogenicity with the host tissue. Additionally, since the vessels or tubular grafts of the present invention are produced with a biocompatible protein matrix material and may include the growth of cells from the patient or compatible cells, the vessel or tubular graft administered to the host tissue further enhances acceptance and remodeling of the vessel or tubular graft by the host tissue. It is again noted that remodeling of the protein matrix device of the present invention is the modifying, adapting and/or transforming the device into an interwoven and/or functioning part of the host tissue.

Furthermore, the vessels and/or tubular grafts may also include one or more pharmacologically active agents within or attached to the protein matrix material that may assist in the facilitation of tissue acceptance and remodeling, as well as inhibit additional adverse conditions sometimes related to implantation of vessels, such as platelet aggregation causing blockage of the vessel. In addition to antiplatelet aggregation drugs, anti-inflammatory agent, gene altering agents, enzymes, growth factors and other additional pharmacologically active agents can be included in the vessel and/or tubular graft for localized administration to or near the host tissue.

Figure 12:
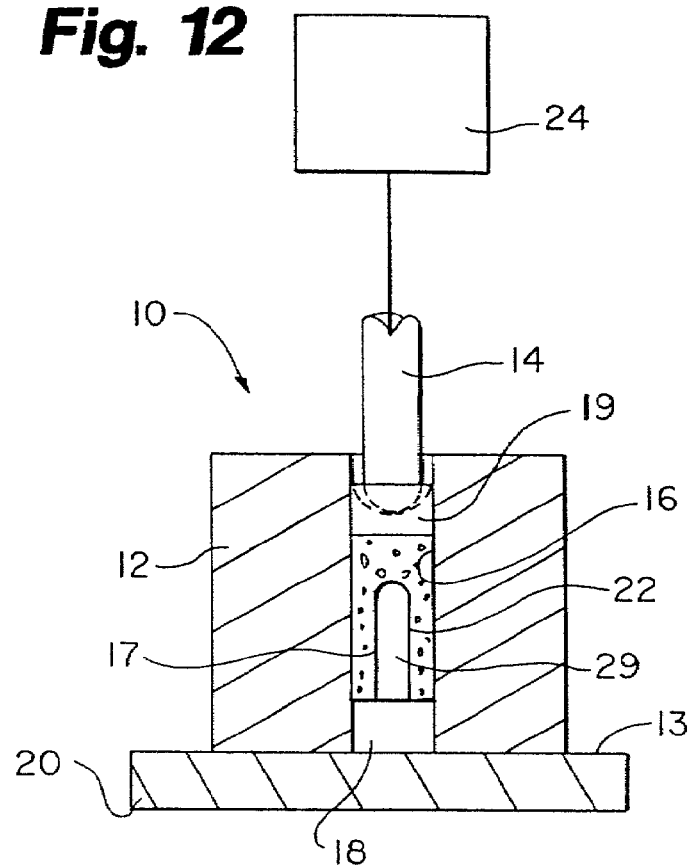
FIG. 12 depicts an embodiment of a compression molding device wherein the inner insert includes a mandrel.
Figure 13:
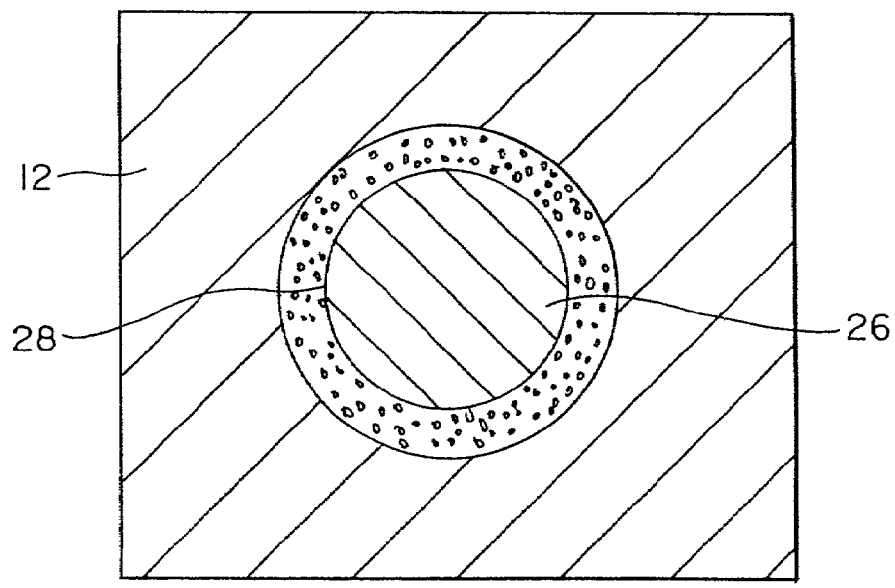
FIG. 13 depicts the top view of an embodiment of the compression molding device without the upper insert or plunger.

Embodiments of the protein matrix vessels and/or tubular grafts may be prepared by methods similar to those described and suggested above. FIGS. 12 and 13 depict a compression molding device wherein the inner insert 18 includes a mandrel 29 that extends upward from the insert 18 into the chamber 17. FIG. 13 depicts a top view of the compression molding device without the upper insert 19 or plunger 14. Following the insertion of a sufficient amount of cohesive body 22 the upper insert 19 and plunger 14 are applied to the cohesive body 22. As with the previous compression molding device embodiments the pressure applied by the plunger 14 and surfaces of the chamber 17 and mandrel 26 to the cohesive body 23 removes the bulk water within the cohesive body 23 thereby resulting in the protein matrix device. The vessel and/or tubular graft is then removed from the compression molding device in a similar way as described above and shown in FIG. 3. The vessel and/or tubular graft generally has a wall thickness of approximately 0.05 mm to 1 cm and preferably has a wall thickness of 0.15 to 0.50 mm.

Furthermore, other tissue grafts may be made by including in the compression molding device a cavity 16 and inserts 18 and 19 that are configured to produce the size and shape of the tissue graft desired. For example valves such as heart valves; bone; cartilage; tendons; ligaments skin; pancreatic implant devices; and other types repairs for tissue that relate to the heart, brain, abdomen, breast, palate, nerve, spinal cord, nasal, liver, muscle, thyroid, adrenal, pancreas, and surrounding tissue such as connective tissue, pericardium and peritoneum may be produced by forming the cavity 16 and inserts 18 and 19 of the molding compression chamber into the corresponding size and shape of the particular tissue part. It is noted, that the above mentioned tissue parts may optionally include one or more pharmacologically active agents or other structural materials, such as metal, polymeric and/or biocompatible materials including wire, ceramic, nylon or polymeric meshes.

As previously described additional polymeric and other biocompatible materials may be included in the protein matrix material of the tissue grafts to provide additional structural stability and durability. Also, other structural materials, such as proteoglycans, can be used in this process. The proteoglycans can be mixed with one or more protein materials in the production of tissue grafts.

Additionally, the protein matrix material included in the tissue grafts may be cross-linked to provide additional desirable features such as to inhibit cell growth, reduce immunogenicity or provide additional structural durability and stability. For example the protein matrix material of the vessels or tubular grafts may be crosslinked by contacting the material with a chemical reagent, such as glutaraldehyde, or other type of crosslinking reagent similar to the procedure performed on the stent device of FIG. 7.

In another embodiment of the present invention, vessels can be used to bring blood to cell-support constructs made of the protein matrix material and bring the blood acted on by these cells back into the body's circulation. The cell support constructs provides the biological environment for the growth and maintenance of various cell types e.g. a protein matrix cell scaffold for hepatocytes or islet cells can be placed in a direct blood link. Such a device will provide the hepatocytes or islet cells with adequate access to the blood supply. For example, the cell support construct can act similar to a functioning pancreas, liver or other viable organ in a biological system. In other words a cell support construct can be produced and incorporated within a biological system as an organ or partial organ replacement.

Another embodiment of the present invention is a protein matrix device that is clear. The procedure for making a clear protein matrix comprises making a mold of collagen and/or elastin as described herein and putting it through a spinning process that aligns the fibers. The clear protein matrix may be utilized in cornea transplants. More, specifically, the procedure includes putting a protein matrix material inside a device that spins upon its axis, similar to a nuclear magnetic resonance or NMR type machine. The spinning device will spin this material at a very high rate around its own axis so that the center of the protein matrix is thrown outward so that the fibers and/or molecules of the protein matrix are aligned.

Since the protein matrix contains water, the protein matrix, at this high rate of spin, starts to act like a fluid and slowly moves the protein matrix molecules into alignment. The greater amounts of water incorporated into the matrix, the easier to align the protein and the other molecules. The process may be enhanced if other molecules, such as proteoglycans like heparin, are incorporated in the matrix to make the protein fibers more slippery. As previously mentioned a clear material, such as this, could be used as a cornea transplant upon growing the requisite cells on the clear matrix.

In preparation of a clear protein matrix material, a sample of protein matrix material, as prepared by the methods described or suggested above, was placed in a probe and inserted into an NMR device. Once inside the NMR machine the protein matrix is spun for 48-72 hours, thereby aligning the fibers and/or molecules and producing the clear matrix.

In another embodiment of making the clear protein matrix material it may be possible to create a device that spins on its axis for this process. The NMR is just spinning the protein matrix around its own axis, so it's possible to create such a device wherein the protein matrix may be placed in the center of the spinning device so that it also would spin on its own axis and create the alignment of the fibers and/or molecules of the protein matrix material.

The protein matrix utilized for making a clear protein matrix could be any shape or size. However, if you're spinning the protein matrix around its own axis, more homogenous force may be applied to all parts of the matrix if it were circular or cylindrical. Furthermore if the circle was made big enough, it could then be cut out into any shape and size, with the idea that all parts of that shape received the same kind of force when produced.

Also, the protein matrix material contains water, typically somewhere between 10-60% water depending upon how it's made. At this high rate of spin, it is possible to get some flow of material and provide forces between the protein molecules that make them correspond to each other in a certain way. Moreover, this water environment gives them a lot of motion and the spinning gets that motion to align so that when you're done, the fibers align. This alignment produces a clear protein material much like the cornea.

Wound Healing Devices

Other embodiments of the present invention include wound healing devices that utilize the protein matrix material. The wound healing devices may be configured in any shape and size to accommodate the wound being treated. Moreover, the wound healing devices of the present invention may be produced in whatever shape and size is necessary to provide optimum treatment to the wound. These devices can be produced in the forms that include, but are not limited to, plugs, meshes, strips, sutures, or any other form able to accommodate and assist in the repair of a wound. The damaged portions of the patient that may be treated with a device made of the protein matrix material include skin, tissue (nerve, brain, spinal cord, heart, lung, etc.) and bone. Moreover, the wound healing device of the present invention may be configured and formed into devices that include, but are not limited to, dental plugs and inserts, skin dressings and bandages, bone inserts, tissue plugs and inserts, vertebrae, vertebral discs, joints (e.g., finger, toe, knee, hip, elbow, wrist,), tissue plugs to close off airway, (e.g., bronchial airway from resected tissue site), other similar devices administered to assist in the treatment repair and remodeling of the damaged tissue and/or bone.

Figure 14:
FIG. 14 depicts an embodiment of a wound healing device shaped in the configuration of an ultra-thin skin graft matrix.

In one embodiment of the wound healing device of the present invention, a protein matrix material may be formed into a dressing or bandage, to be applied to a wound that has penetrated the skin, that utilizes a very thin amount of protein matrix material. FIG. 14 depicts an ultra-thin collagen/elastin matrix that is approximately 0.1 mm in thickness. Thin matrices may be made of one or more suitable biocompatible protein materials, one or more biocompatible solvents and optionally one or more pharmacologically active agents. Furthermore, the protein matrix materials formed into a thin dressing or bandage may be approximately 0.05-5 mm in thickness.

The protein matrix, upon application, adheres to the skin and will remain for days depending upon the conditions. If protected, embodiments of the protein matrix dressing will remain on the skin for a considerable period of time. Moreover, if the protein matrix is acting as a wound dressing and therefore interacting with a wound it will stick very tightly. The protein matrix is also acts as an adhesive when wet and as it dries. It is also noted that the protein matrix of the present invention incorporated into a wound dressing would help facilitate or lessen scarring by helping to close the wound. Furthermore, protein matrix dressings or bandages may be prepared to administer beneficially healing and repairing pharmacologically active agents, as well as, act as a device that may be incorporated and remodeled into the repairing tissue of the wound.

In another embodiment of the present invention, the protein matrix can also be protected with a tape barrier that is put over the matrix and over the wound. A plastic and/or cellophane-like section of material may be used as a tape barrier that does not stick to the protein matrix material but holds it in place and provides more protection from the environment. Tape barriers that are utilized in bandages existing in the art may be used with the dressing of the present invention.

Figure 15:
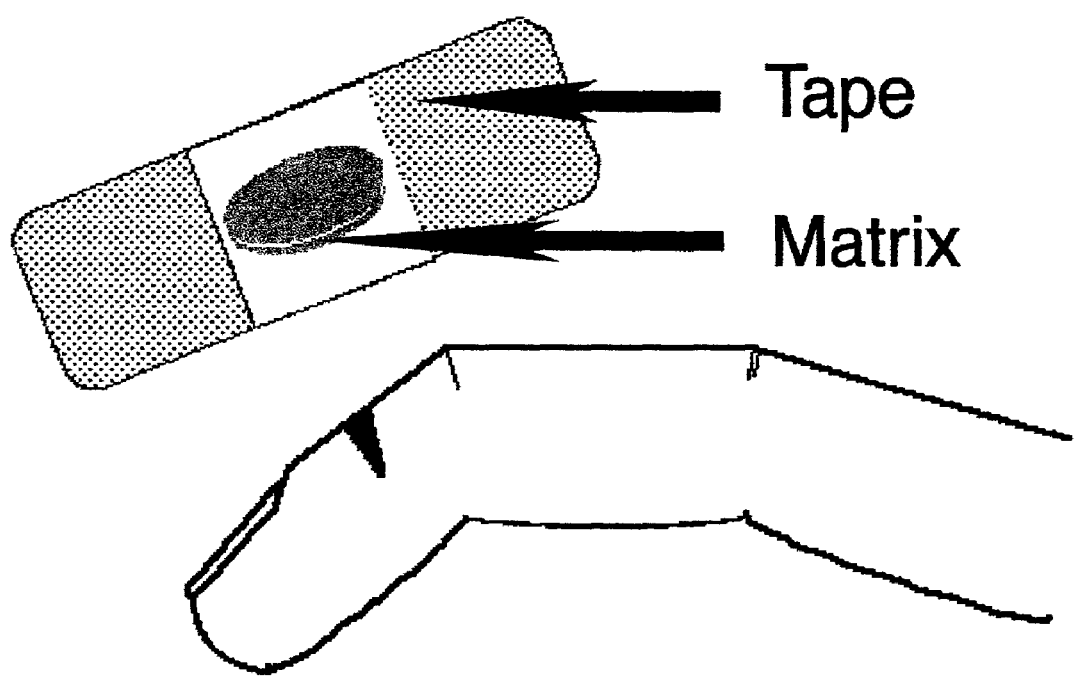
FIG. 15 depicts an embodiment of a wound healing device comprising a protein matrix that is positioned in the center of a non-adhesive strip of material attached to two adhesive ends.

FIG. 15 depicts a wound dressing comprising a protein matrix that is positioned in the center of a non-adhesive strip of material attached to two adhesive ends. The protein matrix can be made from a number of different protein materials including, but not limited to, a collagen/elastin protein mixture (4:1; 4 parts collagen, 1 part elastin). In one embodiment the elastin utilized may be an insoluble elastin made soluble using DMSO. However, a soluble elastin could be used as well. Either type of elastin works well, however, the insoluble is a much cheaper raw material, and it may have some advantages, such as greater potential matrix strength due to it's insoluble characteristics.

Embodiments of the protein matrix wound healing device, also provide a device wherein pharmacologically active agents can be impregnated into it. The matrix or wound dressing may include, but are not limited to, substances that help clotting, such as clotting factors, substances which are helpful for wound healing, such as vitamin E, as well as, anti-bacterial or anti-fungal agents to reduce the chance of infection. Other groups of pharmacologically active agents that may be delivered by the protein matrix wound dressing are analgesics, local anesthetics, other therapeutics to reduce pain, reduce scarring, reduce edema, and/or other type of drugs that would have very specific effects in the periphery and facilitate healing.

The inclusion of such pharmacologically active agents in the protein matrix dressing also facilitates the controlled release of substances, which would assist in healing and/or treat and prevent infection. Furthermore, the protein matrix interacts with the cells that migrate to the wound to facilitate the healing process and that require a matrix and/or blood clotting before they can actually start working to close and remodel the wound area.

The collagen/elastin matrix is made very similar to the cylinders of the protein matrix drug delivery devices explained in the present application, except that only enough material is utilized to produce a thin wafer. Pressure is placed upon this material to flatten it out. Examples of the wound dressings have produced wafers of approximately 0.1 mm in thickness. Because insoluble elastin is present in the production of the protein matrix a solvent is utilized. Examples of solvents utilized in this process are DMSO and ethanol. The insoluble elastin is mixed into the collagen with a judicious amount of solvent to make the protein matrix.

An embodiment of the present invention utilizes DMSO as the solvent. DMSO has some properties, which provide some benefits. However, any solvent, which dissolves or sufficiently wets the insoluble elastin may be used in the present invention. The properties that DMSO has are that it actually was used for some time by athletes to help relax muscle tissue. Athletes utilized DMSO after a long day of working out or playing in competitions; rubbing it on the skin over the muscle tissue that was bothering them would relieve the pain from their muscle tissue. DMSO is inexpensive to make and purchase. Additional advantages of using DMSO in the present invention are that it may assist in the reduction of muscle pain that might occur, depending on the location and type of the wound and it also may allow for the use of proteins that are very insoluble in a water environment, but assists in the production of a strong protein matrix wound dressing.

Another feature of the wound dressing is that only the part of the protein matrix dressing that is needed will integrate with the cells of the wound and be utilized. Generally, over a period of time, a wound will remodel and close utilizing only the amount of the protein matrix material necessary to assist in the process. Any remaining protein matrix not utilized in the mending of the wound will flake away in similar fashion as the way dead skin, surrounding and covering the healed wound, dries and flakes off.

The protein matrix wound dressing could also help people who require more assistance than normal for a wound to actually close. Individuals who have problems with wound healing may find that their wound takes longer to close due to their wound not being able to develop a clot and/or set up a matrix for cells to close the wound. In these situations, such as a person with diabetics or ulcers, the protein matrix may be utilized to assist in healing. The protein matrix provides a material that assists the wound in closing, especially if clotting factors and maybe some other factors that are known in the art and are important to wound care are incorporated into the protein matrix.

Again, the incorporation into the protein matrix of substances, such as biochemicals, that would naturally be incorporated into the wound during healing may be of benefit in the healing process. The protein matrix itself comes in contact with the wound and supplies a scaffold for the cells to interact with and thereby assists in healing the wound. Therefore, the incorporation of the previously mentioned biochemicals, which can be uniformly dispersed and impregnated into the matrix, can further assist in the healing process and increase the prevention of infection, reduction of pain, remodeling of the damaged tissue and all other overall healing results.

The biochemicals, previously referred to, such as factor 14, factor 8 and other similar biochemicals are most crucial to the beginning steps of wound care. The impregnation of such biochemicals into a protein matrix will translate to a faster closing process and hence a faster healing process. These biochemicals are present in our blood at all times and are immediately prepared to function when they come in contact with a wound site. However, sometimes for various reasons a patient's blood does not have enough of these biochemicals or cannot satisfactorily supply a sufficient amount to effectively repair a wound. Therefore, the application of a protein matrix as described herein which is impregnated with such biochemicals can have a beneficial role in stimulating and enhancing the healing process.

It is also possible to extend delivery of chemicals or drugs using this protein matrix as a wound dressing. In one embodiment this can be accomplished by providing a protein matrix wound dressing that includes a patch delivery system adjoined immediately behind the protein matrix dressing. In this example a strip, wrap or patch that includes a larger dosage of the chemical or pharmaceutical active component may be applied behind the protein matrix not in immediate contact with the wound. By administering such a wound healing device, the delivery of chemicals and/or pharmaceuticals could be extended until the wound was healed or the desired amount of chemicals and/or pharmaceuticals were applied. In application, the protein matrix would continue to absorb more chemicals and/or pharmaceuticals from the patch as the initial material impregnated in the matrix was being utilized in the wound. Therefore, the protein matrix would provide a controlled release of the chemical and/or pharmaceutical component and would prevent the administration of too much chemical and/or pharmaceutical component from entering a patient's wound prematurely. Additionally, the protein matrix with adjoining patch may be very beneficial for patients who are compromised in some way from internally supplying the biological substances needed to reduce or prevent them from healing quickly. Examples of such situations where such a protein matrix wound healing device would be beneficial are in cases of diabetes, hemophilia, other clotting problems or any other type affliction that inhibits the adequate healing of a wound. Furthermore, individuals with such conditions may require a great deal more than the clotting agents that can be incorporated into a thin protein matrix. Therefore, the patch may contain more than one additional chemical and/or pharmaceutical components that may benefit from extended contact with the wound in the healing process.

Additionally, embodiments of a moistened protein matrix dressing that includes a patch may be configured to allow a varying controlled release of pharmaceuticals through the matrix by providing a matrix that release molecules at varying rates based on molecule size. This provides a tremendous means for controlling administration of more than one pharmacologically active agent that vary in size. Such controlled release facilitates the administration of pharmaceutical molecules into the wound when they may be needed. For example, the protein matrix dressing may be layered with different types of protein material and biocompatible polymeric material mixtures that control the release of molecules based on size. For example, the protein matrix material may include physical and/or chemical restraints that slow the migration of various size molecules from the patch and through the protein matrix dressing. Furthermore, the larger molecules that are proteins and other macromolecules that need to be in contact with the wound can be impregnated into the protein matrix itself.

Furthermore, the protein matrix dressing may be set up with pores that allow fluid flow through that matrix and also enhances movement of the pharmacologically active agents through the matrix. Pores may be created in the matrix by incorporating a substance in the cohesive body during its preparation that may be removed or dissolved out of the matrix before administration of the device or shortly after administration. Porosity may be produced in a protein matrix device by the utilization of materials such as, but not limited to, salts such as NaCl, amino acids such as glutamine, microorganisms, enzymes, copolymers or other materials, which will be leeched out of the protein matrix to create pores. Other functions of porosity are that the pores create leakage so that cells on outside can receive fluids that include the contents of the matrix and also that cells may enter the matrix to interact and remodel the matrix material to better incorporate and function within the host tissue.

As described herein a protein matrix may be made porous by the utilization of salts or other such materials. However, it is also possible to produce a porous protein matrix by the incorporation of a solution saturated or supersaturated with a gaseous substance, such as carbon dioxide. In one embodiment, carbonated water may be utilized in a sealed and pressurized environment during the production of the protein matrix. The utilization of carbonated water creates bubbles within the protein matrix during the production process. Once the matrix has been shaped into the desired form and removed from the sealed and pressurized environment, the gaseous bubbles escape from the matrix leaving a porous material.

Another embodiment for producing a porous protein matrix makes use of polyvinyl alcohol (PVA or other water soluble polymers). Polyvinyl alcohol (PVA) or other water-soluble polymers can be made into particles that correspond to a specific size. The particles are made by first producing a gel following standard techniques for that polymer. For example, PVA is made into a 4% solution in 100 ml and placed into a vacuum oven at 40° C. for 24 hours. The resulting dried gel is pulverized after freezing with liquid nitrogen. The particles are then separated by a sieve into specific sizes. The water-soluble polymer particles are incorporated into the protein matrix so that they can be dissolved by aqueous solutions to provide a protein matrix that is a three dimensional scaffold for cells to migrate and grow within. The PVA particles will dissolve at rates that are directly proportional to the size and thickness of the protein matrix. The PVA particles can be made with cell enhancing agents or chemicals to act as therapeutics so that residual particles can facilitate cell migration, growth and/or proliferation from the pore structures.

Figure 16:
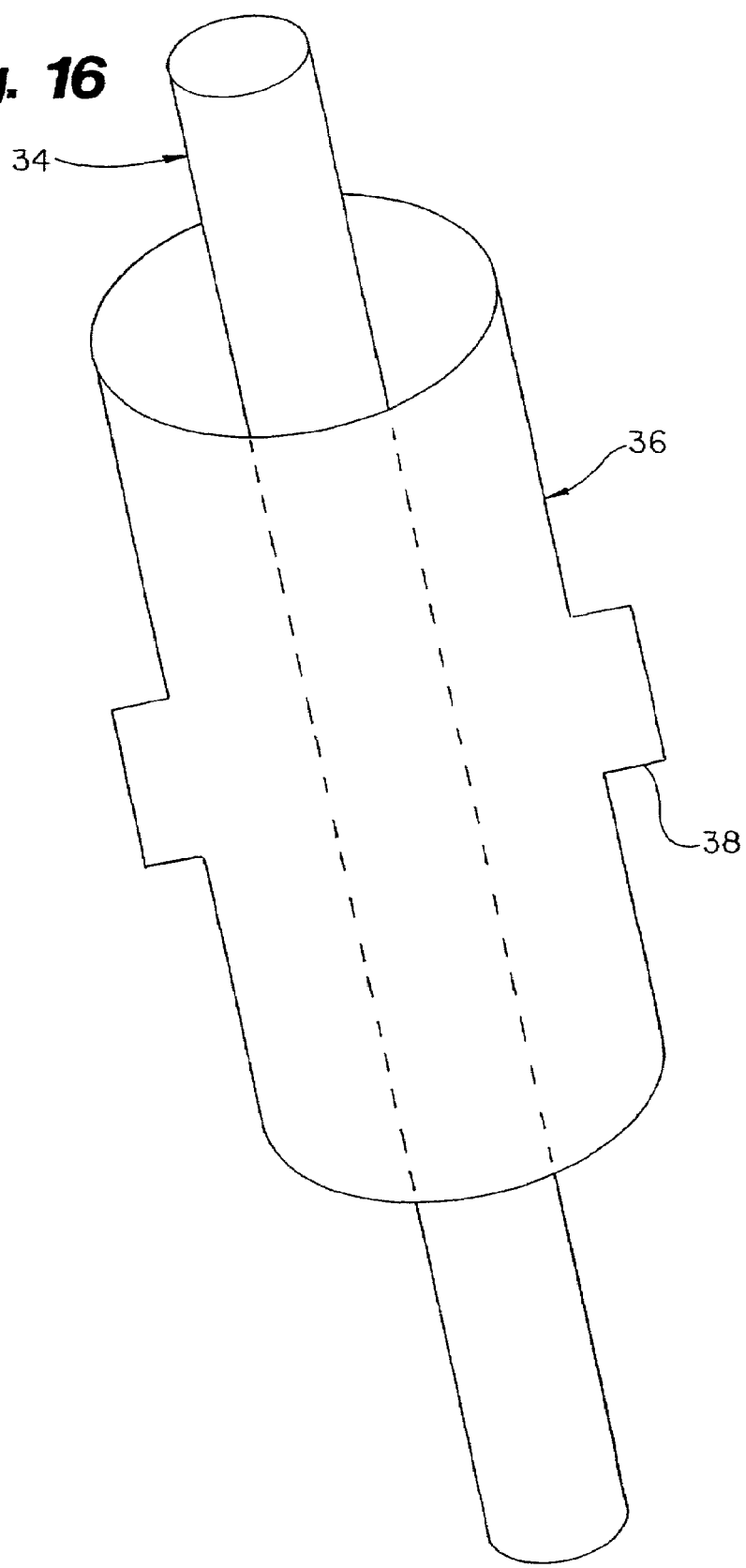
FIG. 16 depicts an embodiment of a protrusion device 34 that includes a port seal.

The protein matrix material of the present invention may also be utilized as port seals for protrusion devices entering and or exiting the patient. FIG. 16 depicts one embodiment of a protrusion device 34 that includes a port seal 36 comprising the protein matrix material of the present invention. The port seal 26 may be included around the point of insertion of a protrusion device, such as an electrical lead or a catheter. Generally, the port seal 36 surrounds the protrusion device 34 and insulates it from the host tissue. One or more tabs 38 may optionally be included on the port seal 36 to assist in the retention of the protrusion device and further seal the opening in the patients skin. The tabs 38 may be inserted under the skin or may remain on the outside of the patient's skin. Also, the biocompatible seal comprising the protein matrix material of the present invention provides stability, reduces the seeping of bodily fluid from around the protrusion and reduces or prevents immunogenicity caused by the protrusion device. Furthermore, the port seal may include pharmacologically active agents that may be produced to deliver anti-bacterial, analgesic, anti-inflammatory and/or other beneficial pharmacologically active agents.

Other embodiments of the present invention include wound-healing devices configured and produced as protein matrix biological fasteners, such as threads, sutures and woven sheets. Threads and sutures comprising various embodiments of the protein matrix material provide a biocompatible fastening and suturing function for temporarily treating and sealing an open wound. Additionally, the biological fasteners may include pharmacologically active agents that may assist in the healing and remodeling of the tissue within and around the wound.

One method of preparing the biocompatible biological fasteners is to manufacture sheets of protein matrix material. Once the sheets of protein matrix material are prepared each sheet may cut into strips, threads or other shapes to form sutures, threads and other biological fasteners (e.g., hemostats). The sheets may be cut using cutting techniques known in the art. Also, the protein matrix threads may be woven into sheets and used as a strengthened protein matrix material that has desired porosity. For example, this woven protein matrix may also be used with cohesive body to form a protein matrix that has a woven protein matrix encapsulated or filled by protein matrix.

Additionally, fibers (large or small, e.g., macro, micro, nano) of a known suturing material, such as nylon, may incorporated in the cohesive body and compressed to make a sheet of protein matrix material. It is noted that the protein matrix forms a cohesive body around the biocompatible thread/fibers during compression to encapsulate the biocompatible fibers into the protein matrix. Once the sheet is prepared it may be cut by methods common to the art to produce a thread/suture that has biocompatible and durable characteristics.

Additional embodiments of wound healing devices that include the protein matrix material of the present invention include but are not limited to dental inserts, dental plugs, dental implants, dental adhesives, and other devices utilized for dental applications. Wounds and dental complications, such as dry socket, present within the interior of the mouth are generally slow to heal, are painful and/or are susceptible to bacterial and other forms of infection. The dental inserts or implants of the present invention may be utilized to remedy such problems since they are biocompatible with the surrounding host tissue and may be manufactured to release appropriate pharmacologically active agents that may assist in healing, relieve pain and/or reduce bacterial attack of the damaged region. Furthermore, the dental plugs, inserts or implants of the present invention include one or more biocompatible protein material and one or more biocompatible solvent that may be incorporated into and remodeled by the surrounding tissue, thereby hastening the healing of the damaged region and/or returning the damaged region to its original state. For example, dental plugs or implants may be administered to open wounds within the mouth region of the patient following tooth extraction, oral surgery or any other type of injury to the interior of the mouth to assist in the healing and regeneration of the damaged region.

In general, the dental plugs, implants or inserts may be administered to the damaged area by any method known in the art. For example a dental plug may be administered to the socket of a tooth after removal by placing a properly sized and shaped dental plug that includes the protein matrix of the present invention into the socket. The dental plug may optionally be fastened to the surrounding tissue of the socket by any means known in the art such as adhesives or sutures. However, it may not be necessary to use any fastening means since the cells of the host tissue may be found to readily interact with the plug and begin to incorporate the plug into the host tissue. As previously suggested, such a dental plug may also include analgesic antibacterial, and other pharmacologically active agents to reduce or prevent pain and infection and to promote the reconstruction of the damaged region.

Other Protein Matrix Devices

The protein matrix material of the present invention may also be utilized in other medical devices to enhance their biocompatibility, provide medical functionality and/or deliver pharmacologically active agents. One example, of other devices that utilized the protein matrix material of the present invention may be as an intrauterine device (IUD). An IUD is a contraceptive device that is placed within the uterus for the purpose of inhibiting conception. Generally, the protein matrix may be produced into any IUD like configuration known in the art and inserted into the uterus. The protein matrix mesh may be prepared by utilizing methods previously described or suggested in the application. Upon insertion of protein matrix mesh and/or particles of any shape into the uterus, the mesh and/or particles interact with the uterine wall cells to create a natural fibrotic meshwork that closes the uterus by fusing the uterine walls together to thereby inhibit the endometrial lining from forming inhibiting menstruation and conception. The IUD protein matrix device may also include pharmacologically active agents that aid in the production of the fibrotic meshwork and/or locally treat the surrounding tissue.

Additionally other protein matrix device embodiments include a protein matrix that has incorporated into it a marker system that allows the matrix to be located and imaged using ultrasound, MRI, X-Ray, PET or other imaging techniques. The image marker can be made with air bubbles or density materials that allow easy visualization of the protein matrix by ultrasound. The incorporated materials can be metallic, gaseous or liquid in nature. Specific materials that may be utilized as image markers incorporated into the protein matrix material include, but are not limited to, Gd-DPTA. It may be possible to cause the material to react to an imaging technique, i.e., ultrasound to make bubbles or through the addition of another chemical or substance to the system (e.g., peroxide addition to a protein matrix that contains peroxidase as an intrauterine marker that can be monitored by ultrasound). Also, the addition of a harmless unique salt solution, or enzyme, may promote gas production by the protein matrix as an ultrasound maker.

The protein matrix can contain agents that can be seen by ultrasound, MRI, PET, x-ray or any imaging device that is either known, in development or developed in the future.

Other embodiments of the present invention are protein matrices, which can include imprints that provide for specific site location for attachment of substances, such as chemicals, cells or enzymes, or for preventing or reducing attachment of such substances. Examples of materials that may be targeted for specific attachment sites on the protein matrix may be cell adhesion molecules or electro-conductive molecules.

The protein matrix can be of any size, shape or form and can be imprinted with any pattern desired depending upon the application. For example, an embodiment of the imprinted protein matrix may take the form of a blood vessel. The exterior of the blood vessel may be imprinted with a pattern that limits the attachment of cellular material that facilitates capillary growth to the exterior. This promotion of angiogenesis provides a number of benefits including the reduction of inflammation to the vessel surroundings and the further promotion of the surrounding tissue's acceptance and incorporation of the vessel.

Another embodiment includes the protein matrix in the form of a sphere. Such a matrix may be imprinted in areas with a substance that inhibits the binding of biological tissue upon implantation in only these predetermined areas. More specifically, a protein matrix may be impregnated with an adhesive substance, which would facilitate binding to tissue. Therefore, the portions of the protein matrix imprinted with the nonbonding substance are thereby prevented from adjoining the surrounding tissue. However, the regions not imprinted would adhere to the tissue and perform the intended functions.

Methods of imprinting the protein matrix with a desired pattern can be performed by any means known in the art. For example, the utilization of UV light can produce a crosslinking pattern upon the protein matrix. Many difference crosslinking agents can be used but crosslinking agents that are only active upon UV activation can selectively attach chemical substances to the protein matrix. This crosslinking can occur either on the surface or within the protein matrix. One function of such a crosslinking pattern would be to inhibit the attachment of cells. Alternately, it is also possible to attached molecules that will allow attachment of cells. Chemicals, enzymes, short peptides or large peptide segments can be crosslinked to selected areas of the protein matrix. Such substances can be utilized to attract and enhance the attachment and/or growth of various cells.

Another embodiment of the present invention relating to an imprinting method is the use of masking systems to create the imprinted pattern. The pattern on a protein matrix may be produced by covering the protein matrix with a mask that has the desired pattern and exposing the covered matrix to a chemical substance, such as glutaraldehyde or any crosslinking agent (e.g., UV-activated chemical). The chemical substance contacts the portions of the protein matrix not covered by the mask and crosslinking occurs. Alternatively, when utilizing UV-activated chemicals, the mask blocks the light thereby inhibiting crosslinking so that crosslinking only occurs at unmasked sites. The mask is then removed thereby providing a protein matrix with both crosslinked and non-crosslinked portions. The non-crosslinked areas can provide locations for the attachment or access to chemicals, cells, enzymes, oligonucleotides, other proteins, etc. Furthermore, these site-specific attachment areas of the protein matrix may be utilized for diagnostic reasons, the growth of cells or as access points for other chemicals or enzymes.

Finally the imprinted protein matrix has applications in the protein chip technology described above. The imprinting of patterns upon the protein matrix chip may produce chips, which provide a number of similar characteristics as a silicon chip or silicon coated substance. As previously suggested, such an embodiment may be beneficial in various diagnostic applications.

EXAMPLES

The drug delivery devices of the present invention will now be further described with reference to the following non-limiting examples and the following materials and methods that were employed.

Xanthine oxidase, superoxide dismutase, capsaicin and dexamethasone were obtained from (Sigma Chemical Company, St. Louis Mo.). The silklike, elastinlike polymer SELP7 was obtained from Protein Polymer Technologies, San Diego, Calif.

Test Method 1. Thermal Sensitivity Test

The thermal sensitivity tests referred to herein below were conducted as follows. Thermal sensitivity was measured by the time required for each rat to withdraw its hind paw from a 56° C. hot plate (commercially available under the trade designation 35-D from IITC Life Science Instruments, Woodland Hills Calif.). Specifically the rats were positioned to stand with one hind paw on a hot plate and the other on a room temperature board. Latency to withdraw each hind paw from the hot plate was recorded by alternating paws and allowing at least 15 seconds of recovery between each measurement. If no withdrawal occurred from the hot plate within 15 seconds, the trial was terminated to prevent injury and the termination time was recorded. Testing ended after three measurements per side and the mean was calculated for each side.

Test Method 2. Motor Capacity Test

The motor capacity tests referred to herein below were conducted as follows. The rat is held in the same manner as during the thermal sensitivity testing so that it is positioned to stand on one leg against an electronic balance. The resistance of the rat's leg is measured as the force against the balance in grams. Previous results from control experiments show that a 200-275 gram rat exerts about 150-225 grams of force with a normal leg. However, if the leg is showing a lack of motor capacity from local anesthetic action, then forces of only from about 30 to about 70 grams are expected. Thus, a lack of motor capacity resulting in the rat exerting only from about 30 to about 70 grams of force against the balance shows that the administered drug delivery device has delivered enough of a pharmacologically active agent to produce local anesthetic action.

Example 1

Preparation of a Drug Delivery Device Comprising a Biodegradable Protein and an Enzyme The enzyme xanthine oxidase was dissolved in deionized water to 0.28 units/100 μl. This xanthine oxidase solution was mixed in with 50 mg protein (SELP7) to form a coatable composition. The composition was then coated on a glass surface to form a film with a thickness of from about 0.1 to about 0.3 mm. The coated film was allowed to dry at room temperature until dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 5 mm long, utilizing the compression molding device discussed hereinabove. The resulting cylinder had a solvent content of approximately 30% to about 60%. This cylinder was cut into four equal pieces so that each piece contained approximately 0.07 xanthine oxidase units/piece. These pieces were frozen at −80° C. until used within 4 weeks.

Example 2

Preparation of a Drug Delivery Device Comprising a Biodegradable Protein and an Enzyme The enzyme superoxide dismutase (SOD) was dissolved in deionized water to 30.0 units/100 µl. This SOD solution was mixed with 50 mg (SELP7) to form a coatable composition. The composition was then coated on a glass surface to form a film with a thickness of from about 0.1 mm to about 0.3 mm. The coated film was allowed to dry at room temperature until dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 5 mm long, utilizing the compression molding device discussed hereinabove. The resulting cylinder had a solvent content of from about 30% to about 60%. This cylinder was cut into four equal pieces so that each piece contained approximately 7.5 units of SOD per/piece. These pieces were frozen at −80° C. until used within 4 weeks.

Example 3

Preparation of a Drug Delivery Device Comprising a Biodegradable Protein and Liposheres Liposheres with 3.6% of the local anesthetic bupivacaine were made as described in U.S. Pat. No. 5,188,837. From about 200 million to about 400 million of these liposheres were then suspended in 150 µl deionized water. This suspension was then mixed with 30 mg SELP7 to form a coatable composition. The composition was then coated onto a glass surface to form a film with a thickness of from about 0.1 to about 0.3 mm. The coated film was allowed to dry at room temperature until the film was dry enough so as to be cohesive, i.e., to a solvent content of from about 50% to about 70%. The resulting film was rolled up, placed in a 3.5 mm diameter mold and compressed at 1750 psi for 2 minutes to form a 3.5 mm diameter cylinder, approximately 4 mm long, utilizing the compression molding device discussed hereinabove. The resulting cylinder had a solvent content of from about 30% to about 50%. Four cylinders were made according to this procedure. These cylinders were refrigerated at 4° C. until used within 4 weeks.

Example 4

Preparation of a Drug Delivery Device Comprising a Biodegradable Protein and Two Pharmacologically Active Agents Drug delivery devices were prepared with differing concentrations of the two pharmacologically active agents capsaicin and dexamethasone as follows. Specifically, first drug delivery devices were prepared comprising 6 mg of capsaicin and 6 mg dexamethasone by dissolving these amounts in 100 µl ethanol. This solution was then added to a solution of 128 mg SELP7 dissolved in 150 µl water to form a coatable composition. This composition was then coated onto a glass surface to form a film with a thickness of from about 0.1 mm to about 0.3 mm film. The coated film was allowed to dry at room temperature until dry enough so as to be cohesive, i.e., to a solvent content of from about 50% to about 70%. The resulting film was rolled up, placed in a 3.5 mm diameter mold and compressed at 7600 psi overnight to form a 3.5 mm diameter cylinder, approximately 5 mm long, utilizing the compression molding device discussed. The cylinder was dried to a solvent content of from about 30% to about 50% in a vacuum and then cut into three equal pieces. From initially added quantities, each pellet was calculated to contain approximately 2 mg capsaicin and 2 mg dexamethasone, weighing approximately 35 mg each.

Second drug delivery devices were prepared comprising 6 mg of capsaicin and 1.2 mg dexamethasone by dissolving these amounts of these agents in 25 µl ethanol. This solution was then added to a solution of 120 mg SELP7 dissolved in 200 µl deionized water to form a coatable composition. This composition was then coated onto two glass surfaces to form two films with thicknesses of from about 0.1 mm to about 0.3 mm. The films were allowed to dry at room temperature until dry enough so as to be cohesive, i.e., to a solvent content of from about 50% to about 70%. The resulting films were rolled up, each placed in a 3.5 mm diameter mold and compressed at 7600 psi overnight to form two 3.5 mm diameter cylinders, approximately 5 mm long, utilizing the compression molding device discussed. The resulting cylinders had a solvent content of from about 30% to about 60%. These cylinders were cut into 5 equal pellets. From initially added quantities, each pellet was calculated to contain approximately 2.4 mg capsaicin and 0.24 mg dexamethasone, weighing approximately 30 mg each.

Example 5

Preparation of an Injectable Drug Delivery Device Comprising a Biodegradable Protein, an Additive and an Opioid Analgesic Injectable drug delivery devices comprising a biodegradable protein, an additive and an analgesic were made as follows. The opioid analgesic, sufentanil citrate (obtained from National Institute on Drug Abuse) was desalted by adding ammonium hydroxide and extracted with n-hexane, collection of solvent and evaporation. The desalted sufentanil was reconstituted in 20 µl of 90% ethanol containing approximately 4,500,000 cpm of tritiated sufentanil (obtained from Jannsen Pharmaceutica, Belgium) to 2.0 mg/20 µl. The biodegradable protein SELP7 was dissolved in deionized water to 20 mg SELP7/30 µl and spread into a thin layer approximately 5 cm by 5 cm in area. Immediately thereafter, 10 mg of finely pulverized powder of an additive, fatty acid dimer: sabacic acid (FAD:SA in 1:4 ratio), was added to the center of the protein solution area. Immediately thereafter, the sufentanil dissolved in the ethanol was added very slowly to the mound of FAD:SA over a time period of a few minutes, i.e., from about 1 to about 5 minutes. After the sufentanil solution had soaked into the FAD:SA powder, the components were thoroughly mixed to form a coatable composition. The composition was then coated onto a glass surface to form a film with a thickness of approximately 0.1-0.2 mm. The film was allowed to dry at room temperature until capable of forming a cohesive body, i.e., to a solvent content of from about 50% to about 70%. The resultant was rolled up and cut into many small pieces. Each piece was placed in a 0.63 mm diameter mold and compressed at 3,000 psi for 2 minutes to form 0.63 mm diameter cylinders, approximately 1.5 mm long and weighing about 0.85 mg to 1.05 mg, utilizing the compression molding device discussed hereinabove. The drug delivery devices were then exposed to gamma irradiation (60-90 KRads) for sterilization and stored in a refrigerator (4° C.) until used within 8 weeks.

Example 6

Preparation of an Implantable Drug Delivery Device Comprising a Biodegradable Protein, an Additive and an Opioid Analgesic Implantable drug delivery devices comprising a biodegradable protein, an additive and an analgesic were made as follows. The opioid analgesic sufentanil citrate (obtained from National Institute on Drug Abuse), was desalted by adding ammonium hydroxide, extracted with n-hexane, collection of solvent and evaporation. The desalted sufentanil was reconstituted in 20 μl of 90% ethanol containing approximately 4,500,000 cpm of tritiated sufentanil (obtained from Jannsen Pharmaceutica, Belgium) to 2.0 mg/20 μl. The biodegradable protein SELP7 was dissolved in deionized water to 42.3 mg (SELP7)/200 μl and spread into a thin layer approximately 6 cm by 6 cm in area. Immediately thereafter, 22.5 mg of finely pulverized powder of an additive, the fatty acid dimer:sabacic acid (FAD:SA in 1:4 ratio) was added to the center of the protein solution area. Immediately thereafter, the sufentanil dissolved in the ethanol was added very slowly to the mound of FAD:SA over a period of a few minutes, i.e., from about 1 minute to about 5 minutes. After the sufentanil solution had soaked into the FAD:SA powder, the components were thoroughly mixed to form a coatable composition. The composition was then coated onto a glass surface to form a film with a thickness of approximately 0.1-0.2 mm. The film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form a 3.5 mm diameter cylinder, approximately 4 mm long and weighing 54.1 mg, utilizing the compression molding device discussed hereinabove. This device was then exposed to gamma irradiation (60-90 KRads) for sterilization and stored in a refrigerator (4° C.) until used within 8 weeks.

Example 7

Preparation of an Implantable Drug Delivery Device Comprising, Biodegradable Protein, an Additive and an Opioid Analgesic Implantable drug delivery devices comprising a biodegradable protein, an additive and an opioid analgesic were made as follows. The opioid analgesic sufentanil citrate (obtained from National Institute on Drug Abuse) was desalted by adding ammonium hydroxide, extracted with n-hexane, collection of solvent and evaporation. The desalted sufentanil was reconstituted in 20 μl of 90% ethanol containing approximately 3,500,000 cpm of tritiated sufentanil (obtained from Jannsen Pharmaceutica, Belgium) to 2.0 mg/20 μl. The biodegradable protein SELP7 was dissolved in deionized water to 15 mg (SELP7)/200 μl and spread into a thin layer approximately 6 cm by 6 cm in area. Immediately thereafter, 35.0 mg of finely pulverized powder of the additive glutamine, was added to the center of the protein solution area. Immediately thereafter, the sufentanil dissolved in the ethanol was added very slowly to the mound of glutamine over a time period of a few minutes. After the sufentanil solution had soaked into the glutamine powder, the components were thoroughly mixed to form a coatable composition. The composition was then coated onto a glass surface to form a film with a thickness of approximately 0.1-0.2 mm. The cast film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form 3.5 mm diameter cylinders, approximately 2 mm long and weighing 39.1 mg, utilizing the compression molding device discussed hereinabove. This device was then exposed to gamma irradiation (60-90 KRads) for sterilization and stored in a refrigerator (4° C.) until used within 8 weeks.

Example 8

Preparation of an Implantable Drug Delivery Device Comprising a Biodegradable Protein, an Additive and an Opioid Analgesic Implantable drug delivery devices comprising a biodegradable protein, an additive and an analgesic were made as follows. The opioid analgesic sufentanil citrate (obtained from National Institute on Drug Abuse), was desalted by adding ammonium hydroxide, extracted with n-hexane, collection of solvent and evaporation. The desalted sufentanil was reconstituted in 20 μl of 90% ethanol containing approximately 4,500,000 cpm of tritiated sufentanil (obtained from Jannsen Pharmaceutica, Belgium) to 2.0 mg/20 μl. The biodegradable protein SELP7 was dissolved in deionized water to 42.3 mg (SELP7)/200 μl and spread into a thin layer approximately 6 cm by 6 cm in area. Immediately thereafter, 22.5 mg of finely pulverized powder of an additive, the fatty acid dimmer: sabacic acid (FAD:SA in 1:4 ratio) was added to the center of the protein solution area. Immediately thereafter, the sufentanil dissolved in the ethanol was added very slowly to the mound of FAD:SA over a period of a few minutes, i.e., from about 1 minute to about 5 minutes. After the sufentanil solution had soaked into the FAD:SA powder, the components were thoroughly mixed to form a coatable composition. The composition was then coated onto a glass surface to form a film with a thickness of approximately 0.1-0.2 mm. The film was allowed to dry at room temperature until capable of forming a cohesive body, i.e., to a solvent content of from about 50% to 70%. The resultant cohesive body was rolled up and placed in a 3.5 mm diameter mold and compressed at 8500 psi for 2 minutes to form 3.5 mm diameter cylinders, approximately 4 mm long and weighing 54.1 mg, utilizing the compression molding device discussed hereinabove. This device was then exposed to gamma irradiation (60-90 KRads) for sterilization and stored in a refrigerator (4° C.) until used within 8 weeks.

Example 9

In vitro Experiment with a Drug Delivery Device Comprising a Biodegradable Protein and an Enzyme A single cylinder piece, prepared as described above in Example 1, was added to a reaction chamber in a spectrophotometer containing xanthine, cytochrome C and other reactants according to previously described superoxide dismutase protocol (Sigma Quality Control Test Procedure EC 1.15.1.1

"Enzymatic Assay of Superoxide Dismutase") enzyme activity of the enzyme xanthine oxidase in the piece was calculated at 0.0005 delta absorbance min (absorbance measured at 550 mm where no enzyme activity produces 0.00000 change in absorbance). In comparison to a 0.01 unit solution of xanthine oxidase, which produced 0.0250 delta absorbance/min, the activity of the xanthine oxidase in the piece equaled 1% of the control solution in a time period of only 3 minutes. Thus, this result indicates that the diffusional barrier provided by the biodegradable polymeric matrix of the drug delivery device allows the enzyme to remain active from within the drug delivery device.

Example 10

In Vitro Experiment with a Drug Delivery Device Comprising a Biodegradable Protein and an Enzyme In this assay system, xanthine oxidase, xanthine, cytochrome C and other reactants were added together to produce a delta absorbance of 0.0250/min. (Sigma Quality Control Test Procedure EC 1.15.1.1 "Enzymatic Assay of Superoxide Dismutase"). SOD activity is measured as the inhibition of the rate of reduction of ferricytochrome C by superoxide, observed at 550 nm, as described by J. McCord, I. J. *Biol Chem.*, 244, 6049 (1969). The addition of a SOD containing piece, produced as described in Example 2 hereinabove, reduced the reaction to 0.0233 delta absorbance/min. Since 1 unit SOD will inhibit the reaction of cytochrome C by 50% in a coupled system using xanthine oxidase, it can be determined that the activity of the SOD pellet equaled 0.14 units of SOD. This activity represents about 2% of the SOD loaded into the biodegradable protein matrix of the drug delivery device. Thus, this result indicates that the diffusional barrier provided by the biodegradable polymeric matrix of the drug delivery device allows the enzyme to remain active from within the drug delivery device.

Example 11

In Vivo Experiment with a Drug Delivery Device Comprising a Biodegradable Protein and Liposheres The drug delivery devices comprising a biodegradable protein and liposheres produced according to Example 3 hereinabove were surgically implanted next to the sciatic nerve of one young adult male Sprague Dawley rat (200-250 g) as described previously by Masters in D. B. Masters et al., *Anesthesiol.*, 79, 340 (1993). Briefly, the rat was anesthetized with 50-75 mg/kg pentobarbital to allow faster recovery for behavioral measurements. Bilateral posterolateral incisions were made in the upper thighs and the sciatic nerves were visualized with care to avoid direct trauma. Drug delivery devices prepared as described in Example 3 were injected around the nerve on one leg, while no drug delivery device was inserted in the contralateral leg to serve as a control. The fascia and muscle surrounding the administration site was closed over to partially restrict egress of the drug delivery device and the entire wound area was lavaged with 0.5 cc of an antibiotic solution (5000 units/ml penicillin G sodium and 5000 μl/ml streptomycin sulfate). The experimenter performing subsequent thermal sensitivity testing and motor capacity tests was unaware of which side received the drug delivery device and which side received nothing.

After having the drug delivery device implanted, the rat was subjected to periodic thermal sensitivity and motor capacity testing according to the protocol described above. As shown in Table 1, the drug delivery devices so implanted produced at least 4 days of local anesthetic block, i.e., a reduction in thermal sensitivity with a concurrent reduction in motor capacity tests compared to the control leg.

TABLE 1

In vivo local anesthetic block produced by a drug delivery device comprising liposheres (they themselves break down within the matrix)

| Time (hr) | Thermal Sensitivity Tests | Motor capacity (weight bearing) |
|---|---|---|
| 0 | 100% ± 5% | 100% ± 2% |
| 2 | 427% | 41% |
| 4 | 560% | 44% |
| 20 | 196% | 56% |
| 26 | 216% | 62% |
| 42 | 195% | 79% |
| 48 | 180% | 77% |
| 96 | 126% | 75% |
| 120 | 105% | 76% |

Example 12

In Vivo Experiment with a Drug Delivery Device Comprising a Biodegradable Protein and two Pharmacologically Active Agents Three "first drug delivery devices" prepared according to Example 4, i.e. comprising 6 mg of capsaicin and 6 mg dexamethasone were implanted next to the sciatic nerve of one young adult male Sprague Dawley rat using the procedures described above in Example 7. The rat was monitored for a period of 624 hours. The results of this experiment are shown in Table 2, below. The first drug delivery devices produced strong thermal sensitivity, but no reduced motor capacity, for 6 days. Because the rat showed some weight loss, the devices were removed on day 6. The rat continued to show a strong reduction in thermal sensitivity for the next 14 days before returning to baseline response levels. In comparison to the contralateral control leg, no reduced motor capacity was detected. Therefore, a very strong sensory neural blockade (analgesia) was obtained by placement of these matrices without associated motor deficits.

TABLE 2

In vivo local anesthetic block produced by a drug delivery device incorporating 6 mg Capsaicin and 6 mg Dexamethasone

| Time (hr) | Thermal Sensitivity Tests (experimental/control) | Motor capacity (weight bearing) |
|---|---|---|
| −48 | 0.98 | nd |
| −24 | 0.98 | 0.99 |
| −1 | 1.02 | 1.01 |
| 2 | 2.47 | nd |
| 4 | 2.04 | 0.97 |
| 24 | 1.80 | 0.95 |
| 48 | 2.72 | 1.01 |
| 96 | 1.94 | 0.86 |
| 144 | 2.86 | 0.91 |
| 168 | 2.34 | 0.97 |
| 192 | 2.19 | 0.99 |
| 216 | 3.04 | 1.00 |
| 264 | 2.59 | 1.00 |
| 288 | 1.76 | 1.05 |
| 312 | 1.58 | 0.99 |
| 318 | 2.55 | 0.99 |

TABLE 2-continued

In vivo local anesthetic block produced by a
drug delivery device incorporating 6 mg
Capsaicin and 6 mg Dexamethasone

| Time (hr) | Thermal Sensitivity Tests (experimental/control) | Motor capacity (weight bearing) |
|---|---|---|
| 336 | 2.06 | 1.01 |
| 360 | 1.65 | 0.98 |
| 384 | 1.65 | 0.99 |
| 432 | 2.16 | 0.99 |
| 456 | 1.35 | 1.01 |
| 480 | 0.92 | 0.99 |
| 504 | 1.10 | 1.01 |
| 528 | 0.98 | 1.02 |
| 552 | 1.38 | 1.00 |
| 624 | 1.07 | 1.01 |

Five "second drug delivery devices," i.e., comprising 6 mg if capsaicin and 1.2 mg dexamethasone, prepared as described above in Example 4 were implanted next to the sciatic nerve of individual rats, where they produced a strong reduction in thermal sensitivity with no concurrent reduction in motor capacity for several days to weeks. All 5 rats showed some weight loss, but far less that that observed with implantation of the first devices.

The results of this experiment are shown in Table 3, below. As shown, a very strong reduction in thermal sensitivity was obtained by implantation of these devices without a concurrent reduction in motor capacity. As is shown, all rats showed similar effects with various durations, i.e., no rats showed motor deficits. Lower doses of capsaicin and dexamethasone showed similar results.

TABLE 3

In vivo local anesthetic block produced by a
drug delivery device incorporating 6 mg
Capsaicin and 1.2 mg Dexamethasone

| Time (hr) | Thermal Sensitivity Tests | Motor capacity (weight bearing) |
|---|---|---|
| −48 | 1.13 | 1.00 |
| −24 | 0.96 | 0.99 |
| −1 | 1.02 | 1.02 |
| 2 | 2.72 | 1.02 |
| 4 | 3.77 | 1.00 |
| 24 | 2.50 | 1.17 |
| 48 | 2.86 | 1.00 |
| 96 | 2.72 | 0.96 |
| 120 | 1.78 | 1.01 |
| 144 | 3.05 | 1.01 |
| 168 | 2.06 | 0.98 |
| 192 | 1.82 | 1.00 |
| 216 | 1.74 | 1.03 |
| 288 | 3.14 | 1.00 |
| 312 | 2.88 | 1.00 |
| 336 | 2.17 | 1.01 |
| 360 | 1.83 | 0.99 |
| 456 | 1.33 | |
| 480 | 1.22 | 0.99 |
| 504 | 1.85 | 1.01 |
| 528 | 1.72 | 0.99 |
| 552 | 1.92 | 1.01 |
| 624 | 2.42 | 0.99 |
| 672 | 2.13 | 0.97 |
| 792 | 1.50 | 1.01 |
| 840 | 1.24 | 0.99 |
| 888 | 1.49 | 1.01 |
| 984 | 1.36 | |

Example 13

In Vitro Experiment with an Injectable Drug Delivery Device Comprising a Biodegradable Protein, an Additive and an Opioid Analgesic Four pellets, prepared as described in Example 5, were each added to separate glass vials treated with a silicone coating (commercially available under the trade designation "Sigmacote" from Sigma Chemical Company, St. Louis, Mo.) to prevent loss of tritiated sufentanil. The pellets were added to the glass vials filled with 15 ml of 0.1 M phosphate buffered saline (pH 7.4), and then were incubated at 37° C. with agitation. At specific time intervals, 20 μl samples were taken in triplicate from each glass vial and measured for radioactive sufentanil using a scintillation counter. As shown in FIG. 8, each of the four matrices produced at least 9 days of sufentanil release following a first order release rate.

Example 14

In Vitro Experiment with an Implantable Drug Delivery Device Comprising a Biodegradable Protein, an Additive and an Opioid Analgesic A single pellet, prepared as described in Example 6 was added to a glass vial treated with a silicone coating (commercially available under the trade designation "Sigmacote" from Sigma Chemical Company, St. Louis, Mo.) to prevent loss of tritiated sufentanil. The glass vial was filled with 15 ml of 0.1 M phosphate buffered saline (pH 7.4), and incubated at 37° C. with agitation. At specific time intervals, 20 μl samples were taken in triplicate and measured for radioactive sufentanil using a scintillation counter. As shown in Table 4, this 3.5 mm diameter cylinder matrix produced at least 75 days of sufentanil release following near zero-order release rate kinetics.

TABLE 4

In Vitro Release Study of
Implantable Drug Delivery Device Comprising a
Biodegradable Protein, an Additive and an Opioid Analgesic

| Time (hr) | Scintillation Counts (cpm) | Cumulative Release (%)* |
|---|---|---|
| 1 | 59050 | 1.48 |
| 4 | 26883 | 3.17 |
| 10 | 228667 | 5.72 |
| 28 | 263650 | 6.59 |
| 49 | 415150 | 10.38 |
| 73 | 455000 | 11.38 |
| 120 | 561517 | 14.04 |
| 200 | 583333 | 14.58 |
| 251 | 619283 | 15.48 |
| 299 | 653517 | 16.34 |
| 428 | 751517 | 18.79 |
| 603 | 901483 | 22.54 |
| 793 | 1281183 | 32.03 |
| 1030 | 1645650 | 41.14 |
| 1199 | 1810450 | 45.26 |
| 1368 | 2093083 | 52.33 |
| 1536 | 2532467 | 63.31 |
| 1704 | 3205867 | 80.15 |
| 1899 | 3446133 | 86.15 |
| 2003 | 3528650 | 88.22 |
| 2239 | 3689717 | 92.24 |

*Based on total expected counts = 4,500,000

Example 15

In Vitro Experiment With An Implantable Drug Delivery Device Comprising a Biodegradable Protein, an Additive and an Opioid Analgesic A single pellet, prepared as described in Example 7 was added to a glass vial treated with a silicone coating (to prevent loss of tritiated sufentanil commercially available under the trade designation "Sigmacote," from Sigma Chemical Company, St. Louis, Mo.). The glass vial was filled with 15 ml of 0.1 M phosphate buffered saline (pH 7.4), and incubated at 37° C. with agitation. At specific time intervals, 20 µl samples were taken in triplicate and measured for radioactive sufentanil using a scintillation counter. As shown in Table 5, this 3.5 mm diameter cylinder matrix produced approximately 2 days of sufentanil release. The addition of glutamine facilitated the release of sufentanil out of the matrix.

TABLE 5

In Vitro Release Study of Implantable Drug Delivery Device Comprising a Biodegradable Protein, an Additive and an Opioid Analgesic

| Time (hr) | Scintillation Counts (cpm) | Cumulative Release |
|---|---|---|
| 1 | 59050 | 1.48 |
| 2 | 671133 | 19.29 |
| 4 | 1495667 | 43.00 |
| 10 | 2230283 | 64.11 |
| 28 | 2908267 | 83.61 |
| 49 | 3346450 | 96.20 |
| 73 | 3422867 | 98.40 |
| 120 | 3439183 | 98.87 |
| 200 | 3430783 | 98.63 |
| leftover cpm | 47792 | |
| in pellet | | |
| *total cpm | 3478575 | |

Example 16

In Vivo Experiment with Drug Delivery Devices Comprising a Biodegradable Protein, an Additive and an Opioid Analgesic The drug delivery devices comprising a protein (SELP7), an additive (FAD:SA), and an opioid analgesic (sufentanil), produced according to Example 5 hereinabove, were injected into the left side of the epidural space adjacent to spinal cord at the fifth lumbar vertebrae in 2 young adult male Sprague Dawley rats. All rats underwent pre-testing for thermal sensitivity tests and motor capacity tests as described hereinabove. The rats were anesthetized with halothane (4% induction, 2% maintenance) and prepared for spinal injection by creating a sterile surgical field over the dorsal aspect of the lower lumbar vertebral column. The placement of the drug delivery devices was in close proximity to the left dorsal root ganglion and nerve root at lumbar level 5, which is associated with nerve input from the left hind paw via the sciatic nerve. After needle insertion validation, drug delivery devices were loaded into an 18 gauge Tuohy epidural needle for injection, most commonly used by anesthesiologists for spinal administration of drug solutions. Before injection of the implants into the epidural space, validation of the space was carried out by x-ray techniques to locate the tip of the needle using an opaque catheter and small x-ray machine. Aspiration of the space occupied by the catheter was also used to validate that it was in the dry epidural space and not the subdural space which is filled with cerebrospinal fluid. The dosage delivered from the drug delivery devices was adjusted by administering more than one implant into the epidural space. To test for a dose response effect, rat F043 received two drug delivery devices containing sufentanil and rat F045 received 6 drug delivery devices containing sufentanil. In this experiment a third rat, F046, was used as a control and received two control devices via the same epidural administration technique. The control devices were made by the same coatable composition technique using the same quantities of biodegradable protein (SELP7), additive FAD:SA, deionized water and ethanol without the presence of sufentanil. The results of this experiment are shown in Table 6, below, where time is in hours relative to epidural administration of the drug delivery devices. Rats F043 and F045 showed prolonged opioid analgesia for approximately 9-12 days in thermal sensitivity tests, performed as described hereinabove, i.e., increased latency (seconds) to remove their paws from a heated surface. Epidural injections of sufentanil citrate at highest possible doses without becoming toxic (5-7 µg/kg), only produced 2 hours of measurable effects to thermal sensitivity testing in three control rats.

TABLE 6

In Vivo Thermal Sensitivity Latency Tests for Drug Delivery Devices Comprising a Protein, and a Polyanhydride Copolymer With and Without an Opioid

| Time (hr) | F043 (2 devices) | | F045 (6 devices) | | F046 (2 control devices) | |
|---|---|---|---|---|---|---|
| | Left Paw | Right Paw | Left Paw | Right Paw | Left Paw | Right Paw |
| −48 | 2 | 1.8 | 1.9 | 2 | 2.5 | 2.4 |
| −24 | 2.4 | 2.1 | 2 | 2 | 2.7 | 2.3 |
| −1 | 1.8 | 1.9 | 1.9 | 2.1 | 2.2 | 2.2 |
| 1 | 2.8 | 2.4 | 12 | 3.7 | 3.5 | 3.2 |
| 4 | 3 | 2 | 5.6 | 2.7 | 2.9 | 2.7 |
| 22 | 2.8 | 2.1 | 5.7 | 2.9 | 2.3 | 2.2 |
| 46 | 3.4 | 2.1 | 8.4 | 3 | 2.3 | 2.4 |
| 74 | 2.9 | 2.1 | 7.1 | 2.5 | nd | nd |
| 119 | 2.8 | 1.8 | 6.8 | 2.4 | 2.5 | 2.4 |
| 144 | nd | nd | 9.7 | 2 | 2.4 | 2.3 |
| 166 | nd | nd | 7.5 | 2.2 | 2.5 | 2.4 |
| 189 | 2.7 | 1.9 | 10.1 | 2.1 | nd | nd |
| 211 | 3.1 | 2.1 | 5.6 | 2.5 | nd | nd |
| 289 | 2.9 | 2.3 | 2.6 | 1.8 | nd | nd |
| 314 | 2.8 | 2 | 2.3 | 1.9 | nd | nd |
| 337 | 2.5 | 1.8 | 1.9 | 1.9 | nd | nd |
| 391 | 3 | 2.1 | 1.8 | 1.9 | nd | nd |
| 435 | 2 | 2.1 | 1.8 | 1.7 | nd | nd |
| 457 | 2.1 | 1.8 | 1.8 | 1.9 | nd | nd |
| 482 | nd | nd | 2 | 2 | nd | nd |

*nd = not determined; Testing was stopped after rat returned to pre-device response level.

Example 17

Figure 18A:
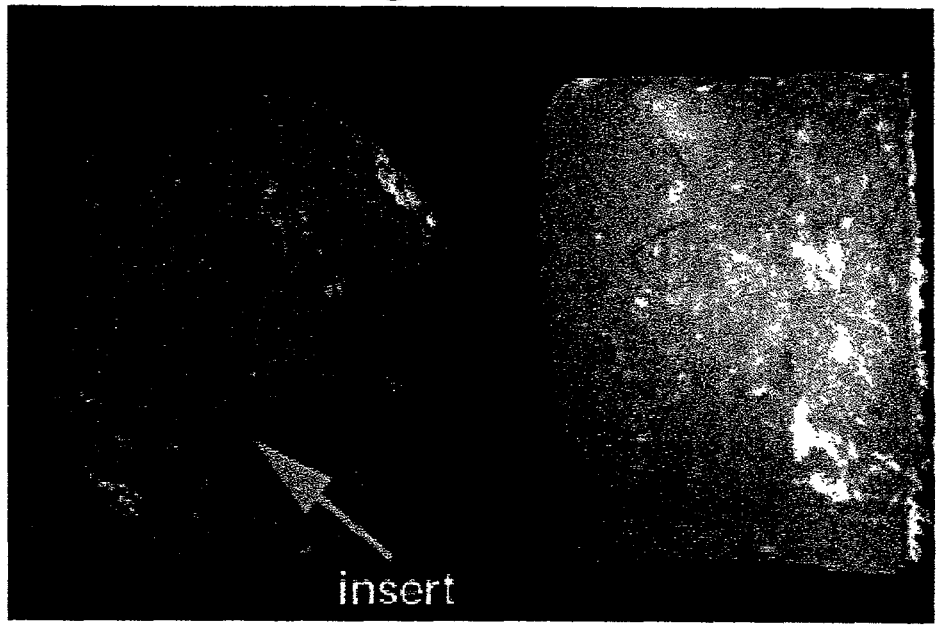
FIG. 18 is a before and after depiction of an embodiment of a protein matrix device that includes a release mechanism.
Figure 18B:

Experiment with Drug Delivery Devices Comprising a Biodegradable Protein Matrix That Includes a Controlled Release Mechanism Two types of drug delivery devices were prepared by compressing crystals of Blue dextran or Gadolinium gadopentetate dimeglumine (Gd-DPTA) (Magnevist) in a polyanhydride copolymer of a 5:1 fatty acid dimer of erucic acid to sebacic acid and then coated by the same copolymer to produce an insert. Following production of the insert, the insert was encapsulated by compression molding in a protein matrix of collagen. The blue dextran or Gd-DPTA & MRI was utilized to verify that the ultrasound triggered device was releasing its drug agents. Each drug delivery device had a diameter of 6 mm and a length of 7 mm. The drug delivery device including blue dextran was submerged in water and held in place with monofilament. Once positioned in water, the drug deliver device was triggered by a focused ultrasound pulse of 50 watts for 5 seconds and was visually observed. FIG. 18 is a before and after depiction of the drug delivery device that includes a release mechanism. The top panel of FIG. 18 is an end and side view of the drug delivery device before ultrasound triggering of the blue dextran polymer insert. The bottom panel is a view of the drug delivery device after ultrasound triggering.

Figure 19:
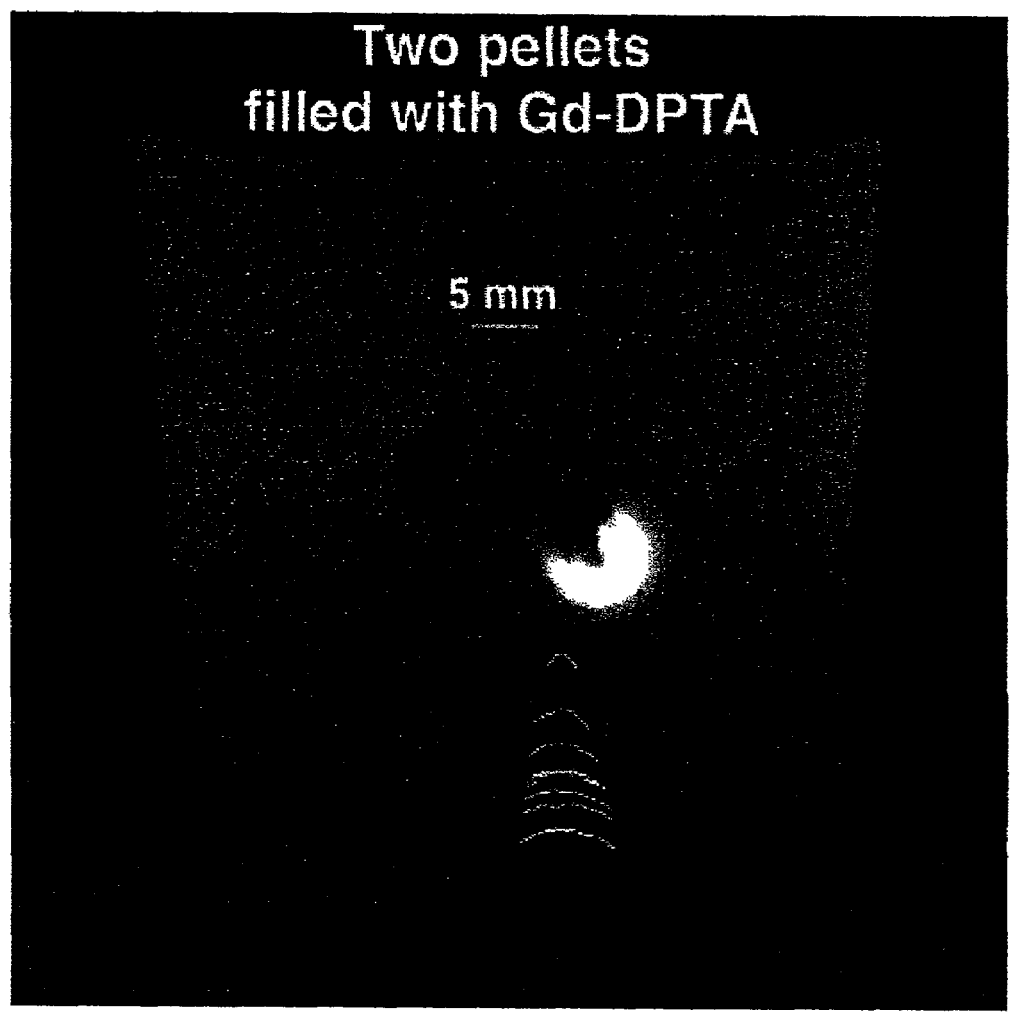
FIG. 19 depicts two protein matrix devices that include release mechanisms contained in an agar gel.
Figure 20:
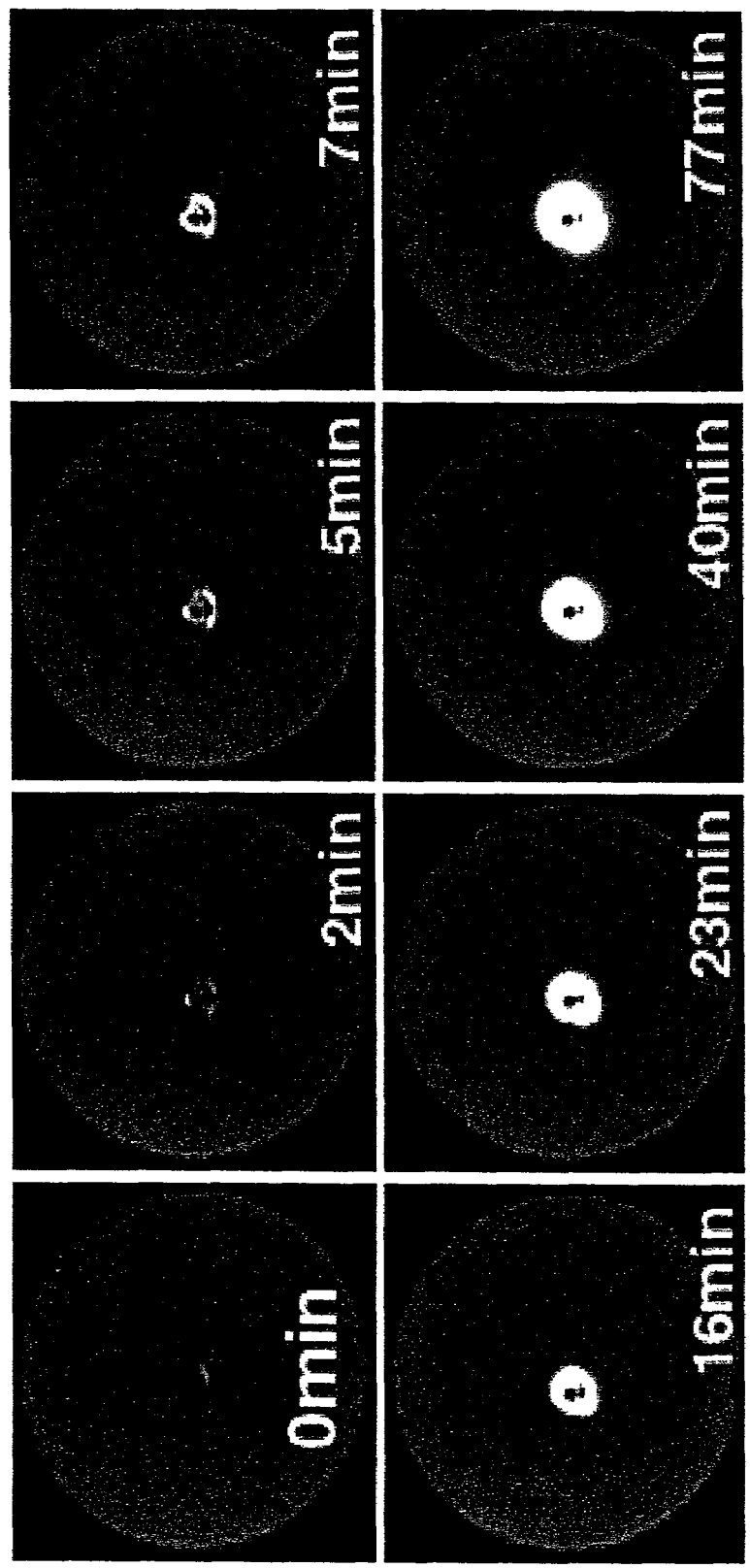
FIG. 20 depicts a time progression illustration of a protein matrix device that includes a protein matrix device following release of the mechanism.

FIGS. 19 and 20 depict the ultrasound triggering of a drug delivery device including a Gd-DPTA copolymer insert. FIG. 19 is an illustration of two Gd-DPTA drug delivery devices contained in an agar gel positioned 5 mm apart. The figure depicts the triggering of the targeted drug delivery device with a focused ultrasound pulse of 50 watts for 5 seconds. The Gd-DPTA was observed by Magnetic Resonance Imaging. The Gadolinium is shown to release from the drug delivery device in greater amounts over time.

FIG. 20 illustrates a time progression depiction of a drug delivery device including a Gd-DPTA copolymer insert that has been triggered by a focused ultrasound pulse of 50 watts for 5 seconds. The first frame at 0 min is taken immediately before the ultrasound pulse. The following frames sequentially illustrate the release progression of the Gd-DPTA into the agar gel.

Example #18

Preparation of Collagen:Elastin (4:1 Ratio) Tubular Grafts

In the preparation of the vascular tubes, Collagen:Elastin was used in a 4:1 ratio and mixed with sterilized saline in amount equal to 600% the weight of the combined collagen and elastin (e.g., 80 mg collagen+20 mg elastin in 600 microliters of water). The material was mixed together and immediately thereafter, the pH was adjusted with drops of 0.1N and 0.5N NaOH until pH indicator strips read 7.4 pH. The material was then partially dried at room temperature until it was to a state where it was cohesive unto itself and was then subsequently formed into a cohesive body. The cohesive body was loaded into the mold were a mandrel insert would receive the cohesive body as mechanically applied pressure forced the cohesive body over the mandrel with a final pressure equal to 5,000 psi for a period of 10 minutes. The result was the formation of a tube around the mandrel where the tube wall thickness was 0.2 mm and the length of the tube was 1 cm. While the protein matrix tube was still on the mandrel insert, it was submersed in 1% glutaraldyhde solution for 2 minutes, resulting in partial cross linking of the outside of the tube. After 2 minutes, the tube-mandrel insert was submersed in saline for 1 minute then it was subjected to a 15 minute submersion in a 0.1 M phosphate buffered saline solution containing 1% glutamine and 1% glycine. The tube was then slipped off the mandrel, where the mandrel was made with a slope of 0.001 inches over the 1 cm length to ease the removal of the protein matrix tube. Also, before the mandril was placed in the mold it was coated with a slippery substance (e.g., glycol or Triton-X100). Finished tubes were stored in saline and sterilized with 10-20 KRADS of gamma irradiation from a cesium source.

The following table includes vascular tubes with various compositions prepared by following the procedure described above.

| | Composition | Ratio | Solvent | pH | Pressure | Len./Dia.*/Wall | Cross-Linking |
|---|---|---|---|---|---|---|---|
| A) | collagen:elastin | (4:1) | saline | 7.4 | 15000 psi | 1 cm/2 mm/0.2 mm | outside surface |
| B) | collagen:elastin | (4:1) | saline | 7.4 | 15000 psi | 1 cm/2 mm/0.2 mm | none |
| C) | collagen:elastin | (4:1) | saline | 7.4 | 15000 psi | 1 cm/2.4 mm/0.2 mm | inside tube |
| D) | collagen:elastin | (4:1) | 9% NaCl | 7.4 | 15000 psi | 1 cm/2 mm/0.2 mm | outside surface |
| E) | collagen:elastin:heparin | (4:1:1) | saline | 7.4 | 15000 psi | 1 cm/2 mm/0.2 mm | outside surface |
| F) | collagen:elastin | (1:1) | saline | 7.4 | 15000 psi | 1 cm/2 mm/0.2 mm | outside surface |
| G) | heparin:elastin:collagen | (1:4:15) | saline | 7.4 | 15000 psi | 1 cm/2 mm/0.2 mm | outside surface |
| H) | elastin:albumin:collagen | (4:1:1) | saline | 7.4 | 15000 psi | 1 cm/2 mm/0.2 mm | outside surface |
| I) | collagen | (1) | saline | 5 | 15000 psi | 1 cm/2 mm/0.2 mm | outside surface |
| J) | chondroitin:elastin:collagen: | (1:4:15) | saline | 7.4 | 15000 psi | 1 cm/2 mm/0.2 mm | outside surface |
| K) | collagen:albumin:elastin | (2:2:1) | saline | 7.4 | 15000 psi | 1 cm/2 mm/0.2 mm | outside surface |
| L) | collagen:albumin:elastin | (2:1:2) | saline | 7.4 | 15000 psi | 1 cm/2.4 mm/0.2 mm | inside surface |
| M) | collagen:albumin:elastin:glutamine | (2:2:1) | saline | 5 | 15000 psi | 1 cm/2 mm/0.2 mm | outside surface |
| N) | elastin:albumin | (1:3) | saline | 7.4 | 15000 psi | 1 cm/2 mm/0.2 mm | outside surface |

*diameter of interior of tube

Example #19

Endothelial Cell Seeding of Tubular Vessels

For this experiment, the protein tubes were produced by the method described in method #18. The endothelial used in the culture are human umbilical vein endothelial cells (HUVEC). The tubes were seeded with these cells in order to obtain a confluent endothelial monolayer within the lumen of the protein tubes. To obtain a high-density culture, the tubes were first cultured with these cells using standard culturing techniques that are known in the discipline. The cells were cultured on a plastic dish that is two times lager than the surface area of the protein tube's lumen. Next, the cells were detached from the culture dish using a trypsin/EDTA solution obtained from ICN Pharmaceuticals, Inc. The cells are then seeded into the lumen of the protein tube. Four hours after seeding, the nonattached cells were be removed. Tubes were then incubated at 37° C. under 5% CO2 and 95% air atmosphere in a standard solution of DMEM. The medium was replaced at least every other day for 4-7 days. Cells have been found to adhere and grow to a confluent monolayer on tubes made of collagen and elastin (4:1 ratio), 100% collagen, and heparin:elastin:collagen (1:4:15).

Example #20

Preparation of Wound Healing Device(Tissue Graft; Wafer)

Figure 21:
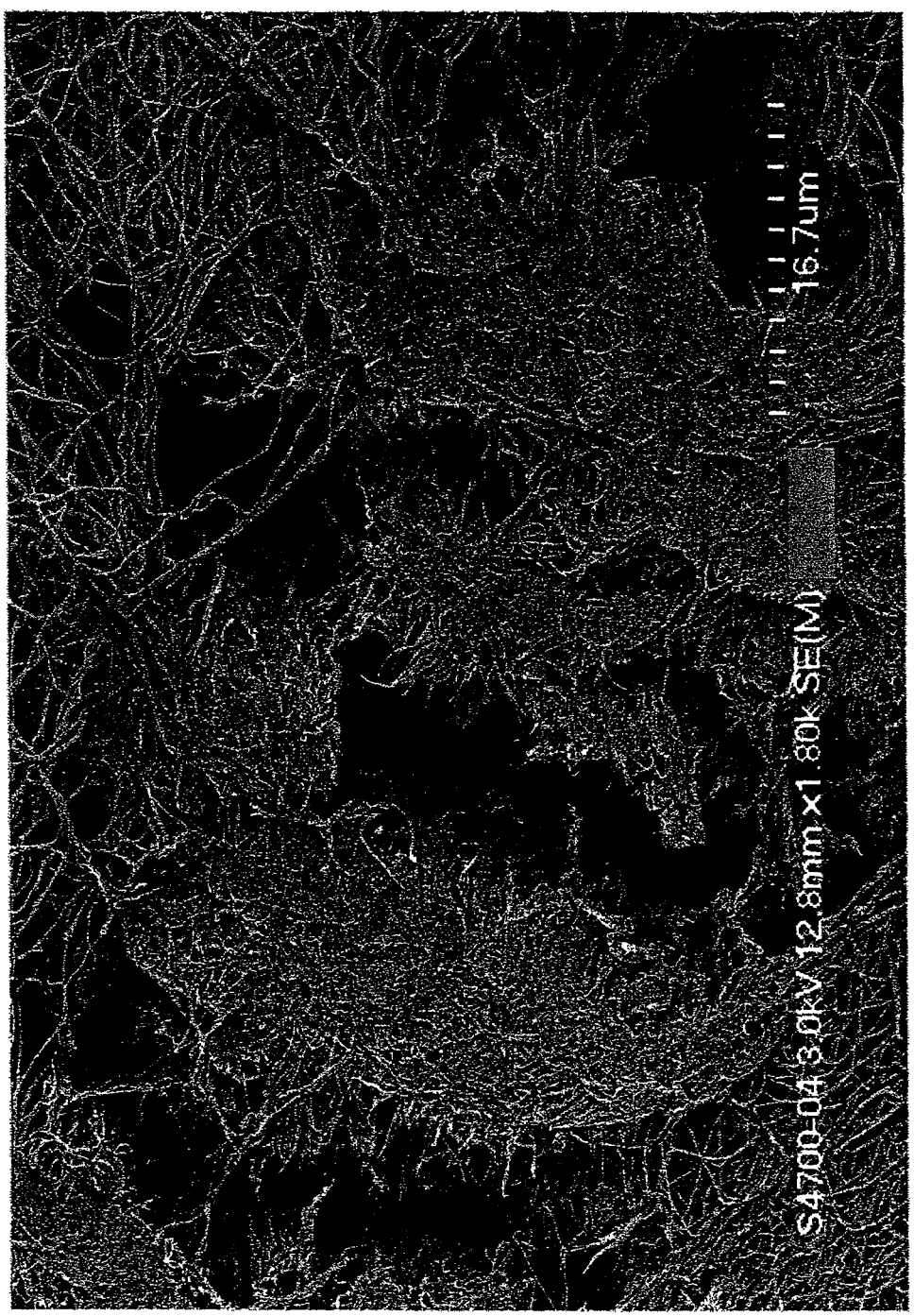
FIG. 21 is a magnified view of an embodiment of a non-crosslinked wafer.
Figure 22:
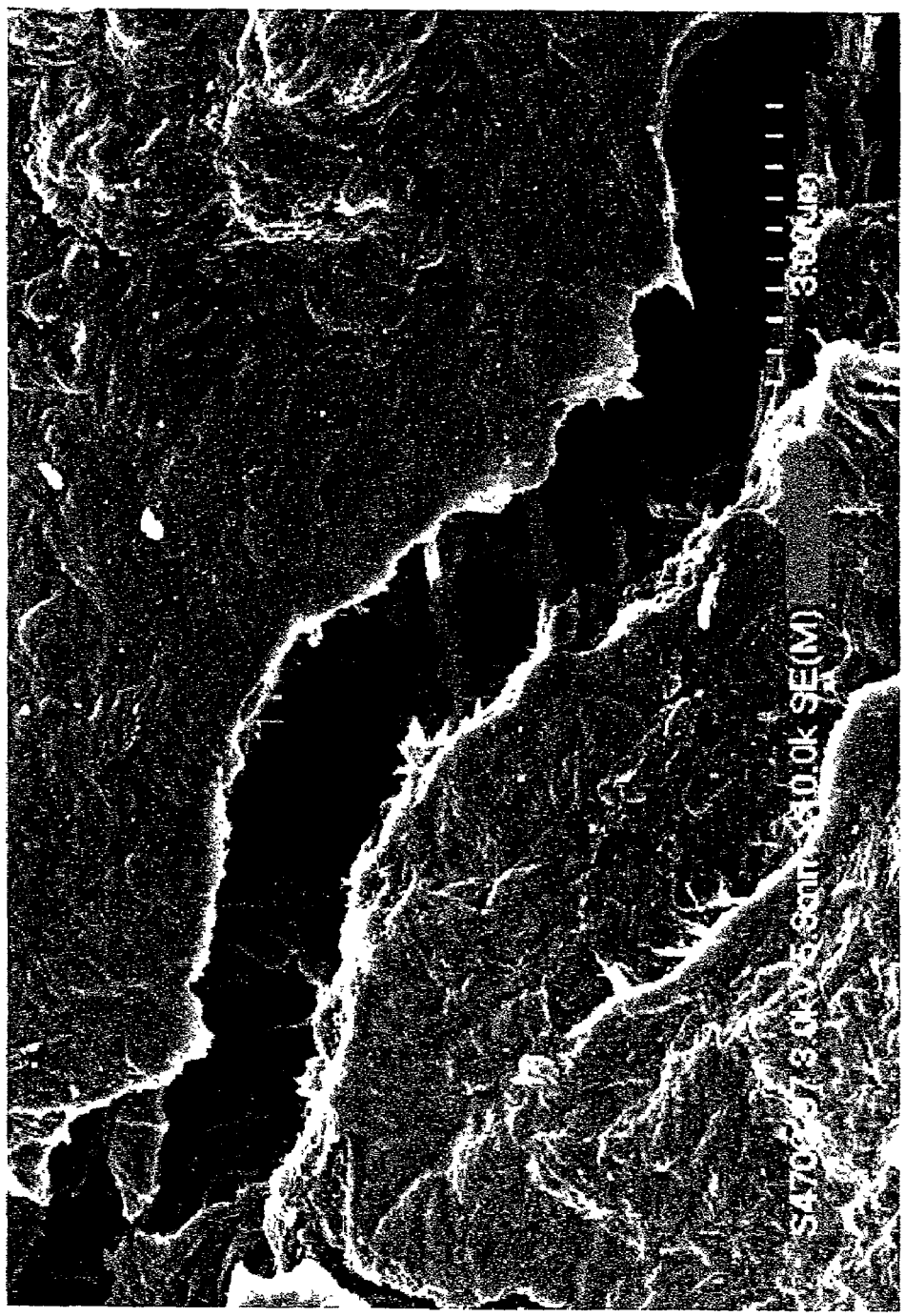
FIG. 22 is a magnified view of an embodiment of a crosslinked wafer.

Dried bovine type I collagen (ICN Biomedicals, Aurora, Ohio) was solubilized using vitrogen and distilled water added in a dropwise manner. Vitrogen was continually added to ensure that the collagen did not dry out before all of the collagen had solubilized. Once the collagen had dissolved, the mixture was allowed to dry until it attained a cohesive state. The collagen was then rolled into a cylinder and placed in a brass mold between two stainless steel inserts. The collagen cylinder was then compressed at 5700 psi for 10 minutes using a pneumatic press. The cylinder was removed and divided into wafers using a razor blade. Wafers were approximately 0.5 mm thick and were 6 mm in diameter unless otherwise stated. Wafers were then recompressed using the pneumatic press for 10 minutes at either 5740 or 28700 psi (henceforth referred to as low and high pressure, respectively). Some wafers were then removed from the brass mold and stored at 4° C. until they were crosslinked. After crosslinking and prior to use in cell culture experiments, all wafers were sterilized using a Cesium irradiator. FIG. 21 is a magnified view of a noncrosslinked wafer after it has been incubating overnight in phosphate buffered saline. FIG. 22 is a magnified view of a crosslinked wafer after it has been incubating overnight in phosphate buffered saline.

Example #21

Glutaraldehyde Crosslinking Wound Healing Device(Tissue Graft; Wafer)

A 1% glutaraldehyde solution (Sigma, St. Louis, Mo.) was used for crosslinking wafers. A single wafer was incubated for 1, 3, 5, 15, or 30 minutes in 1 ml of 1% glutaraldehyde solution in 1X PBS. Samples were then washed in 1 ml of 1 PBS for 10 minutes. This washing procedure was repeated two more times. A revised washing protocol was developed in light of evidence that the cells were dying due to cytotoxic effects of glutaraldehyde. In this new process, glutaraldehyde was removed from the samples and then wafers were transferred to a clean plastic tube. They were then washed in 5 ml of 1X PBS for 4 hours. The PBS was removed and 5 ml of fresh 1X PBS was added for a second washing for 8 hours (overnight). The PBS was again removed and the wafers were washed for 2 hours prior to cell seeding in a modified 1X PBS solution, which consisted of 1 mM glycine, and 1:100 dilution of vitrogen. This last wash was intended to bind up any residual glutaraldehyde and thereby eliminate the cytotoxic effects of free glutaraldehyde. Collagen wafers that did no undergo crosslinking were washed in the same buffers and used as controls.

Example #22

Mechanical Testing System (MTS) of Protein Matrix Material

MTS Testing

Six wafers from each experimental group were tested to determine structural and mechanical properties. Sample thickness was measured using a Fowler micrometer (accurate to 0.1 mm). Cross-sectional areas were calculated by assuming a rectangular cross-section. The UTS and modulus (slope of the stress-strain curve) were determined from the stress-strain curves of the collagen wafers. Stress was calculated by dividing the force by initial cross-sectional area. Stress-strain curves for wafers were determined an MTS Microbionix biomechanical tester controlled by TestStar/TestWare software. Wafers were tested using a gauge length of 0.5 mm and a strain rate of 0.8 mm/s after rehydration for 10 minutes in phosphate buffered saline. The instrument was operated in a dynamic mode at room temperature. The wafers were removed from the solution immediately before testing and mounted onto the screw clamps. A wafer was mounted using two parallel screw clamps such that each clamp secured a segment of the wafer with a gauge length of 0.5 mm. The clamps were connected to the actuator and a 5-Newton force transducer of the MTS Microbionix testing system allowing continuous measurement of the stress response to a constant strain rate in the radial direction in extension by separating the screw clamps at a constant speed. Stress was calculated by dividing the force generated during extension by the initial wafer cross-sectional area (approximated by multiplying wafer thickness by the wafer diameter). Strain was calculated as the natural log of the ratio of the extended distance over the gauge length. The Young's modulus was determined by measuring the slope of the stress/strain curve between strains of 0.2 and 0.8. Ultimate Tensile Strength (UTS) represents that largest stress value sustained by the wafer during testing.

Figure 23:
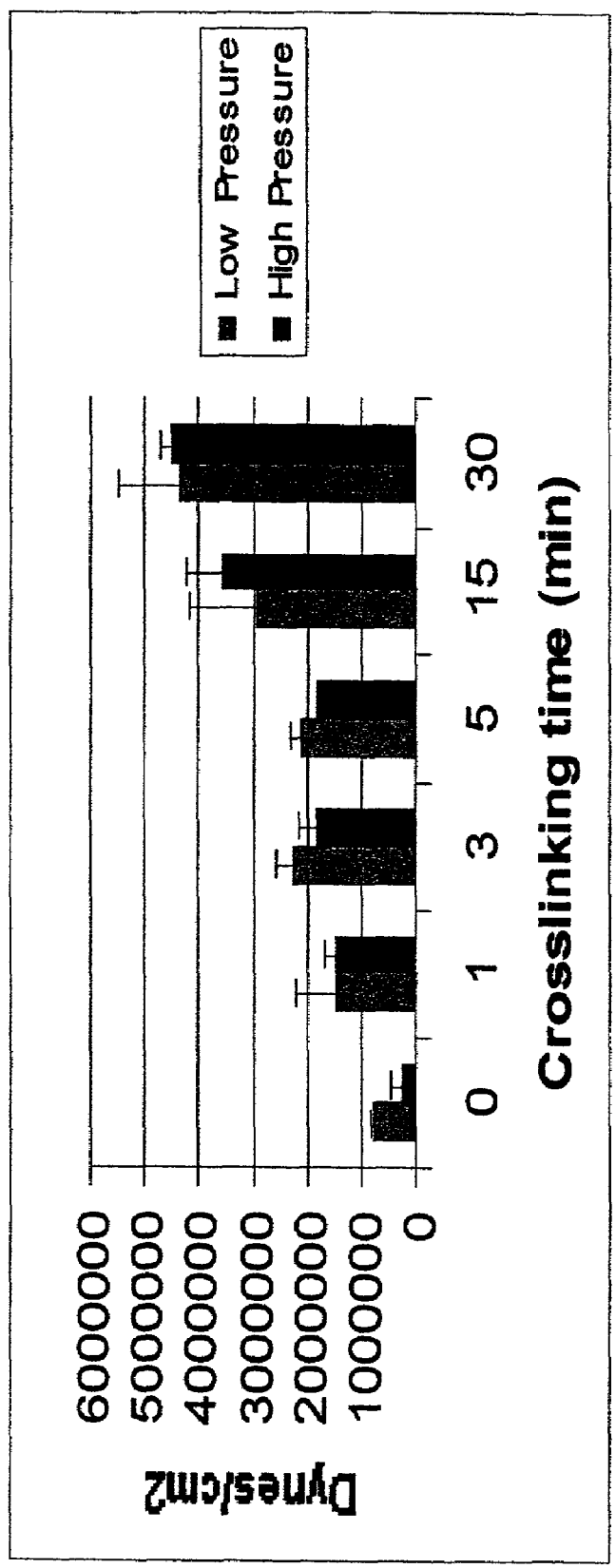
FIG. 23 is a chart of the effect of GA crosslinking and molding pressure on the Young's modulus of collagen wafers.

Crosslinking and Pressure Effects on the Mechanical Properties of Collagen Devices Young's modulus and UTS were assessed used to characterize the mechanical properties of the collagen DDS. An increase in Young's modulus was seen as the duration of glutaraldehyde crosslinking increased for both low (5700 psi) and high (28,700 psi) psi compressive loads (FIG. 23). For the low psi wafers the increase was significant between 0 and 3, 0 and 15, and 0 and 30, 1 and 15, 1 and 30, 3 and 30, 5 and 30 minutes, and 15 and 30 minutes based on ANOVA analysis. For the high psi wafers, the increase was significant between all paired time points except 1 and 3, 1 and 5, and 3 and 5 minutes. In addition, there was no significant difference between the high and low psi systems at any of the crosslinking times based on ANOVA analysis.

Figure 24:
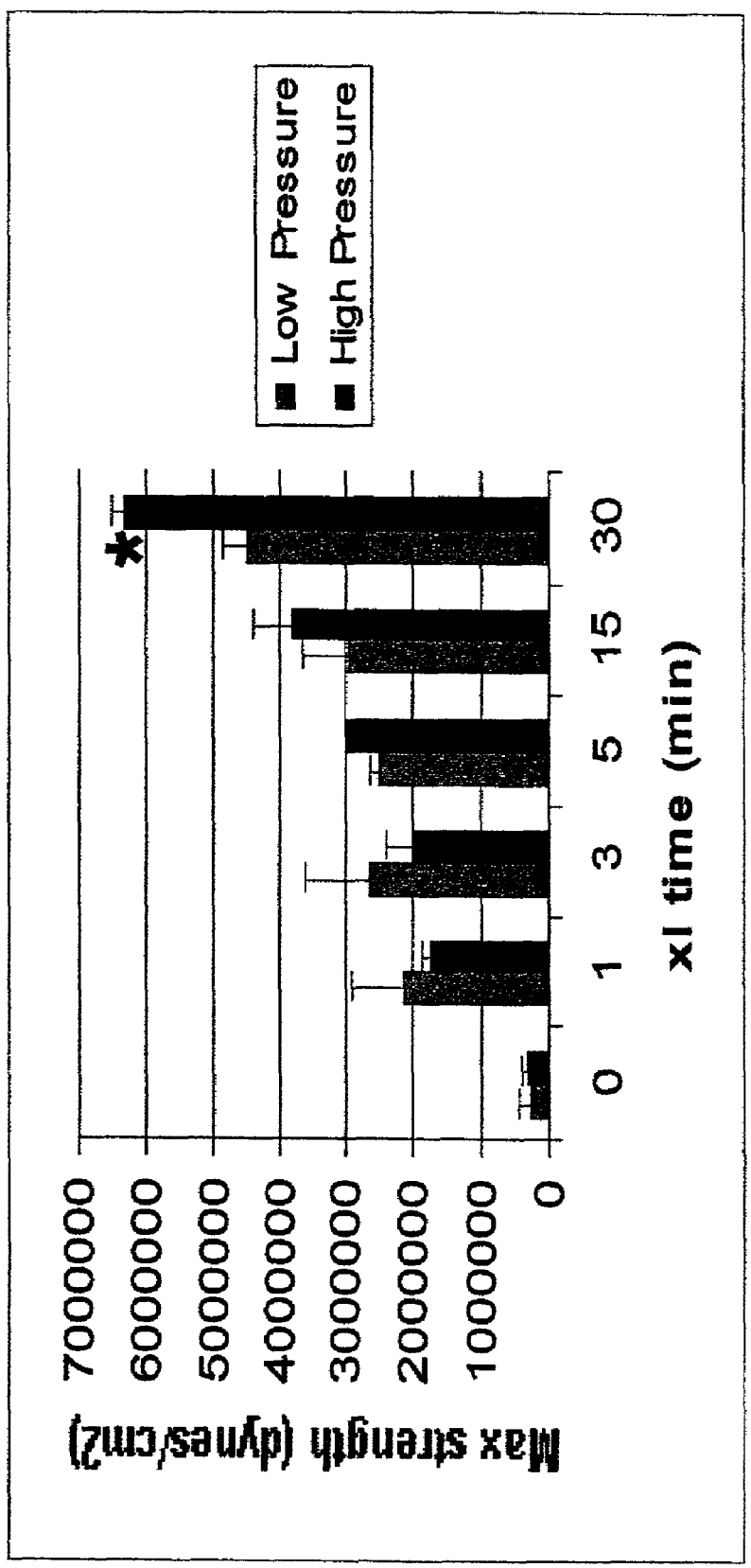
FIG. 24 is a chart of the effect of GA crosslinking and molding pressure on the UTS of collagen wafers.
Figure 25:
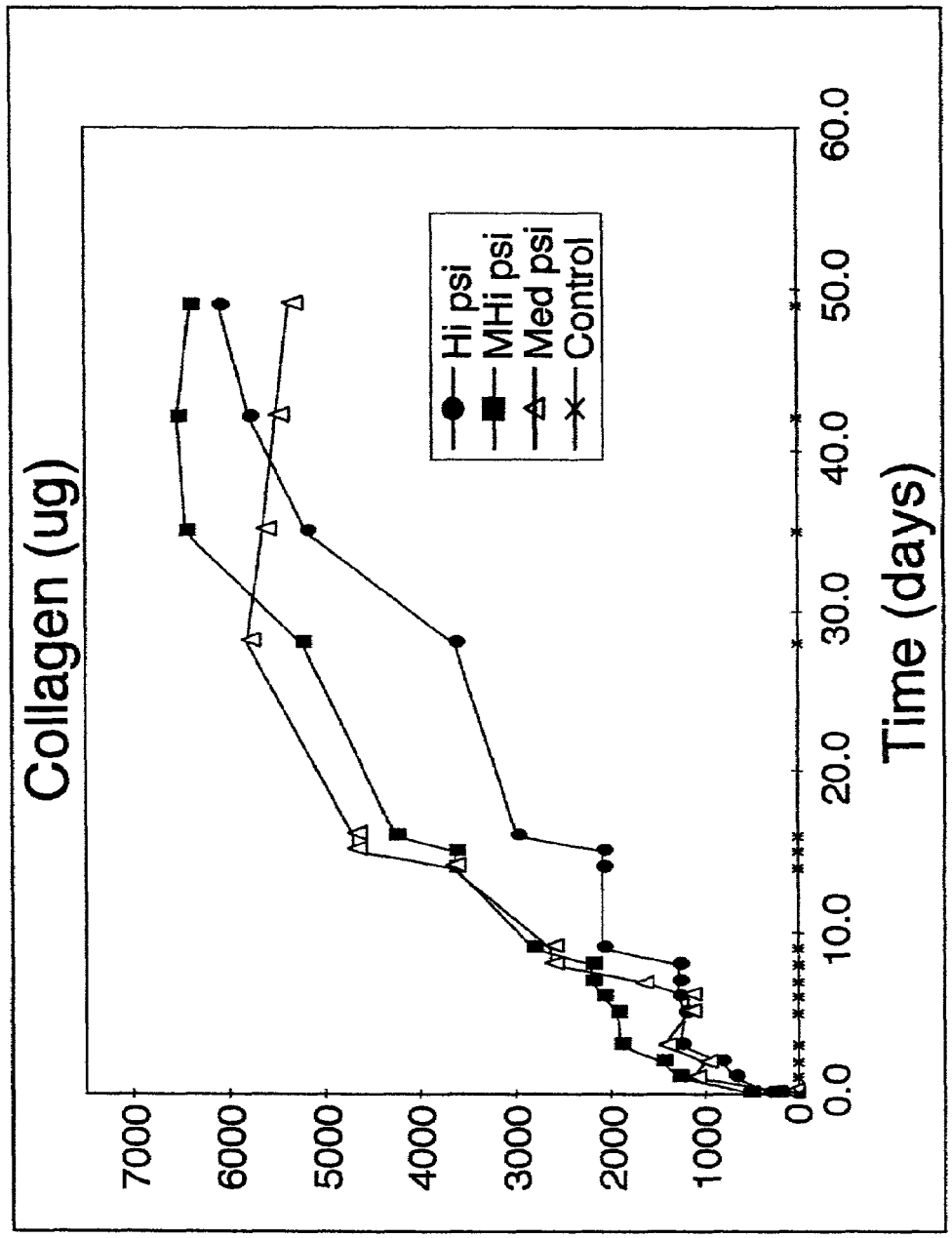
FIG. 25 is a chart regarding the amount of collagen released into PBS involving noncrosslinked embodiments of the present invention.
Figure 26:
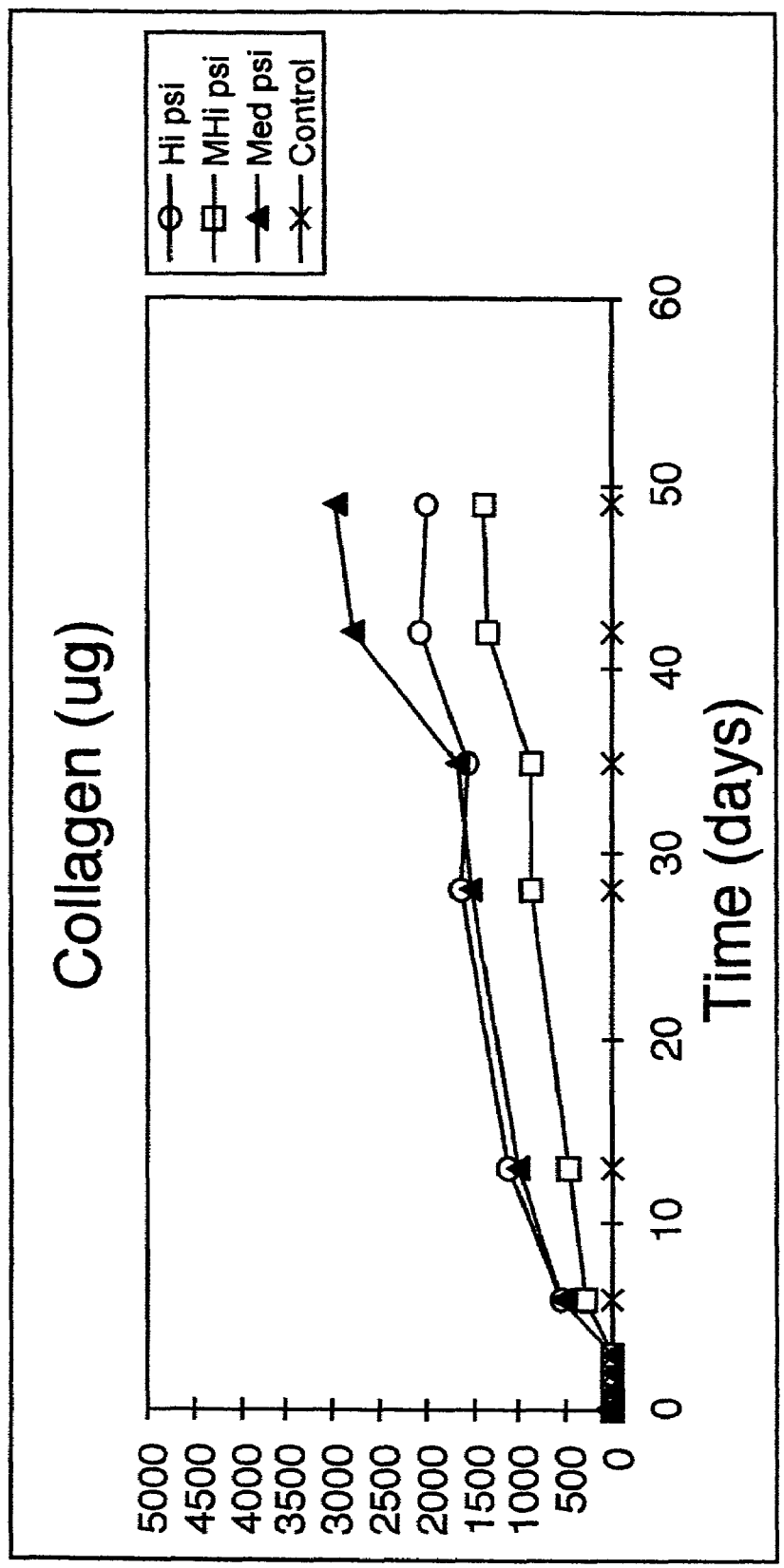
FIG. 26 is a chart regarding the amount of collagen released into PBS involving various embodiments of the present invention crosslinked by contacting with 1% glutaraldehyde for 1 minute.
Figure 27:
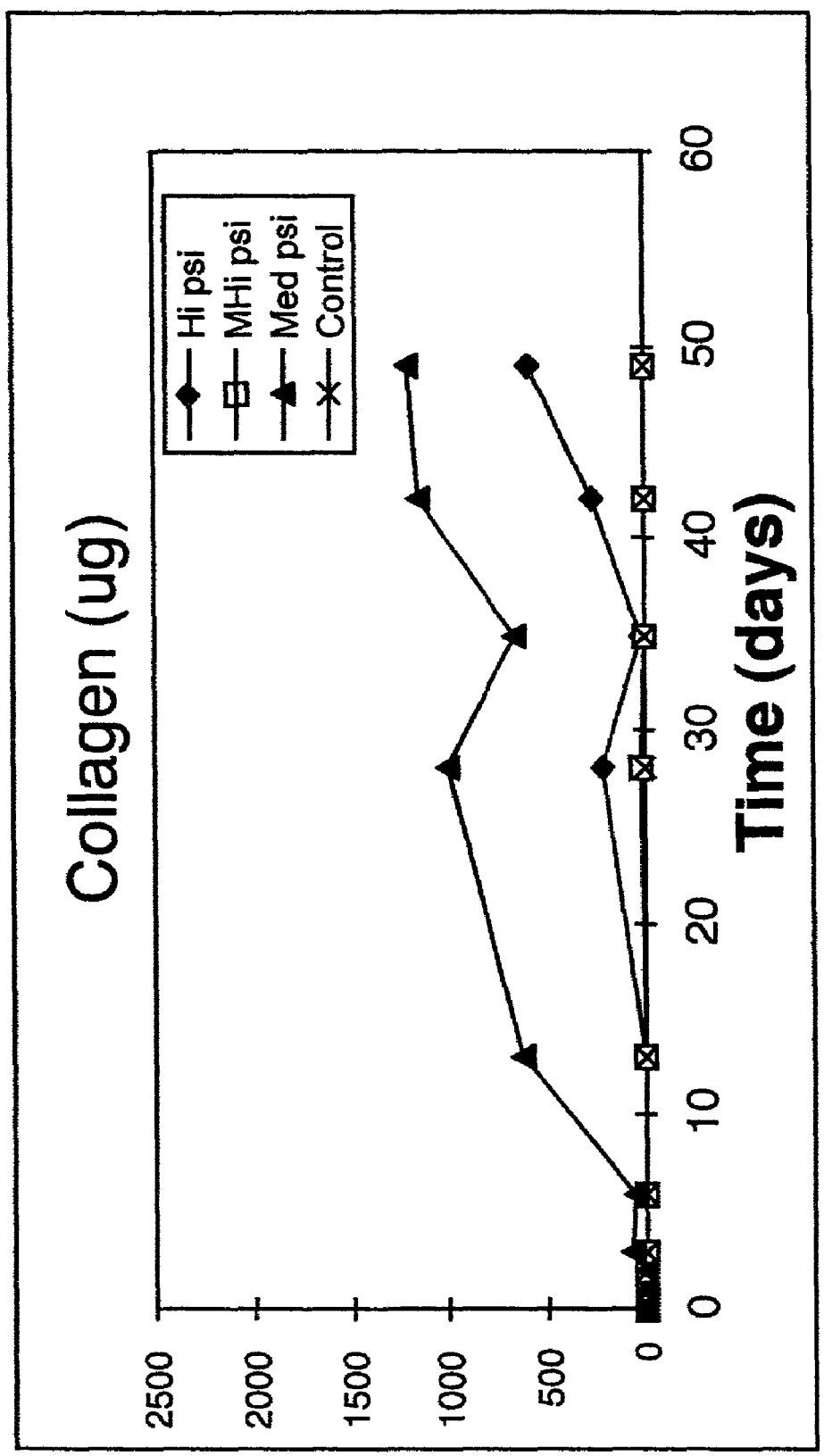
FIG. 27 is a chart regarding the amount of collagen released into PBS involving various embodiments of the present invention crosslinked by contacting with 1% glutaraldehyde for 10 minutes.
Figure 28:
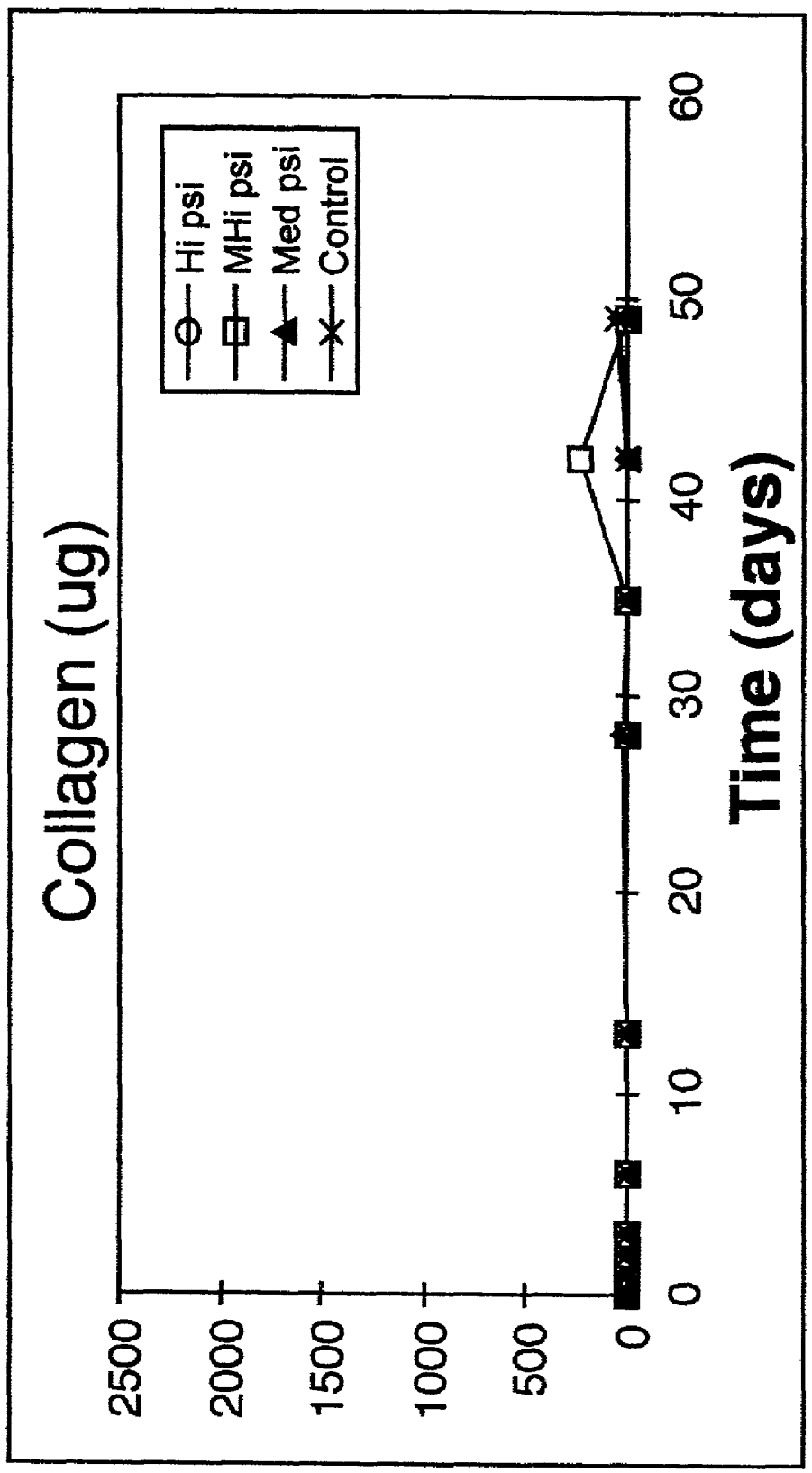
FIG. 28 is a chart regarding the amount of collagen released into PBS involving various embodiments of the present invention crosslinked by contacting with 1% glutaraldehyde for 30 minutes.

The UTS of the collagen systems also increased as the length of crosslinking time increased for both the low psi and high psi load levels (FIG. 24). For the low psi wafers this difference was significant between all pairs of time points except 1 and 3, 1 and 5, 1 and 15, 3 and 5, and 3 and 15 minutes. For the high psi wafers, the increase was significant between all pairs of time points except 1 and 3 minutes based on ANOVA analysis. There was no significant difference between the low psi and high psi system at any of the crosslinking times.

Example #23

Dissolution of Collagen Protein from Collagen Wafers

FIGS. 25-28 depict the results of tests performed regarding dissolution of collagen from collagen wafers made with medium (12,000 psi), high (20,000 psi) and high (28,000 psi) pressures in a compression chamber and with various amounts of crosslinking. The wafers were crosslinked with 1% glutaraldehyde for 0, 1, 10, and 30 minutes corresponding to FIGS. 25-28, respectively. The collagen wafers were analyzed by placing them in phosphate buffered saline in a 15 ml conical Falcon tube (pH 7.4, 37° C.). The Falcon tube was then place in a shaking incubator at 37° C. and set to slow agitation. At various time points samples of the solution were tested by BCA protein assay (Pierce Company) for protein content and recorded.

Example #24

Mechanical Testing System (MTS) of Protein Matrix Material (Vascular Tubes)

MTS Testing

A vascular tube was tested to determine structural and mechanical properties. Sample thickness was measured using a Fowler micrometer (accurate to 0.1 mm). Stress-strain curves for tubes were determined an MTS Microbionix biomechanical tester controlled by TestStar/TestWare software. The tube was wet with a phosphate buffered saline. The instrument was operated in a dynamic mode at room temperature. The tube was mounted onto prongs made to fit the inside diameter of the tube. The prongs were mounted to the actuator and a 5-Newton force transducer of the MTS Microbionix testing system allowing continuous measurement of the stress response to a constant strain rate in the radial direction in extension by separating the prongs at a constant speed. Stress was calculated by dividing the force generated during spreading of the tube walls (approximated by multiplying wall thickness by the tube wall diameter). Strain was calculated as the natural log of the ratio of the extended distance over the gauge length. Ultimate Tensile Strength (UTS) represents that largest stress value sustained by the wafer during testing. The UTS that resulted was equal to 192.6 mmHg.

Example #25

Mechanical and Hydraulic Testing System (MTS) of Protein Matrix Material (Tubular Grafts)

Figure 29:
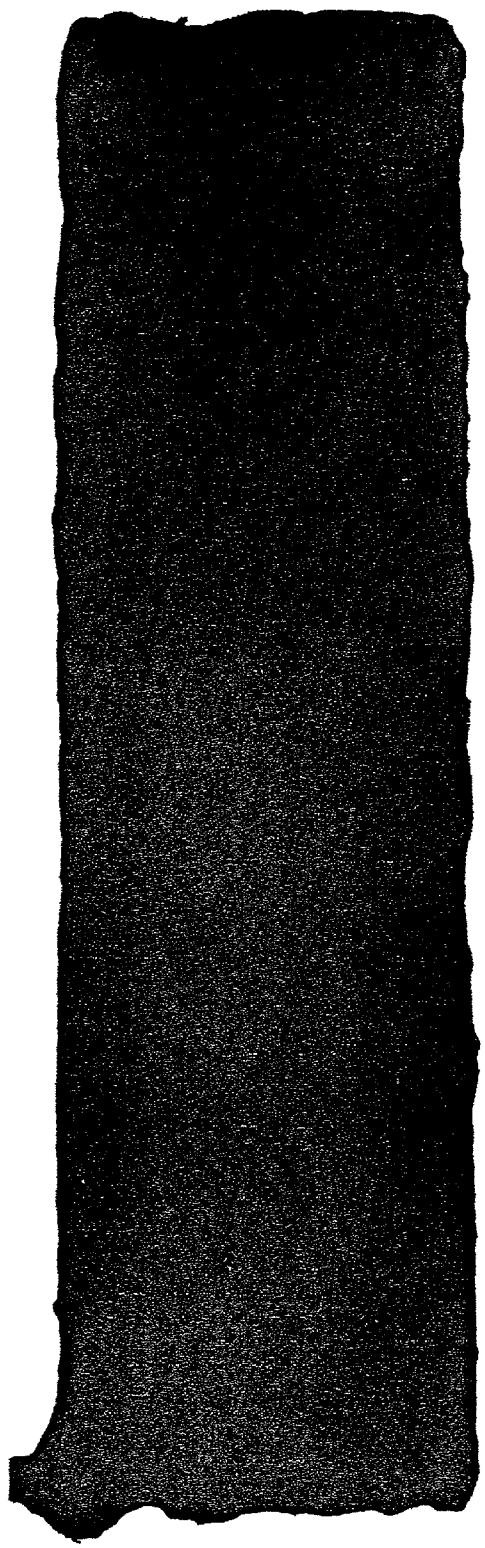
FIG. 29 depicts an embodiment of a vascular tube.
Figure 30:
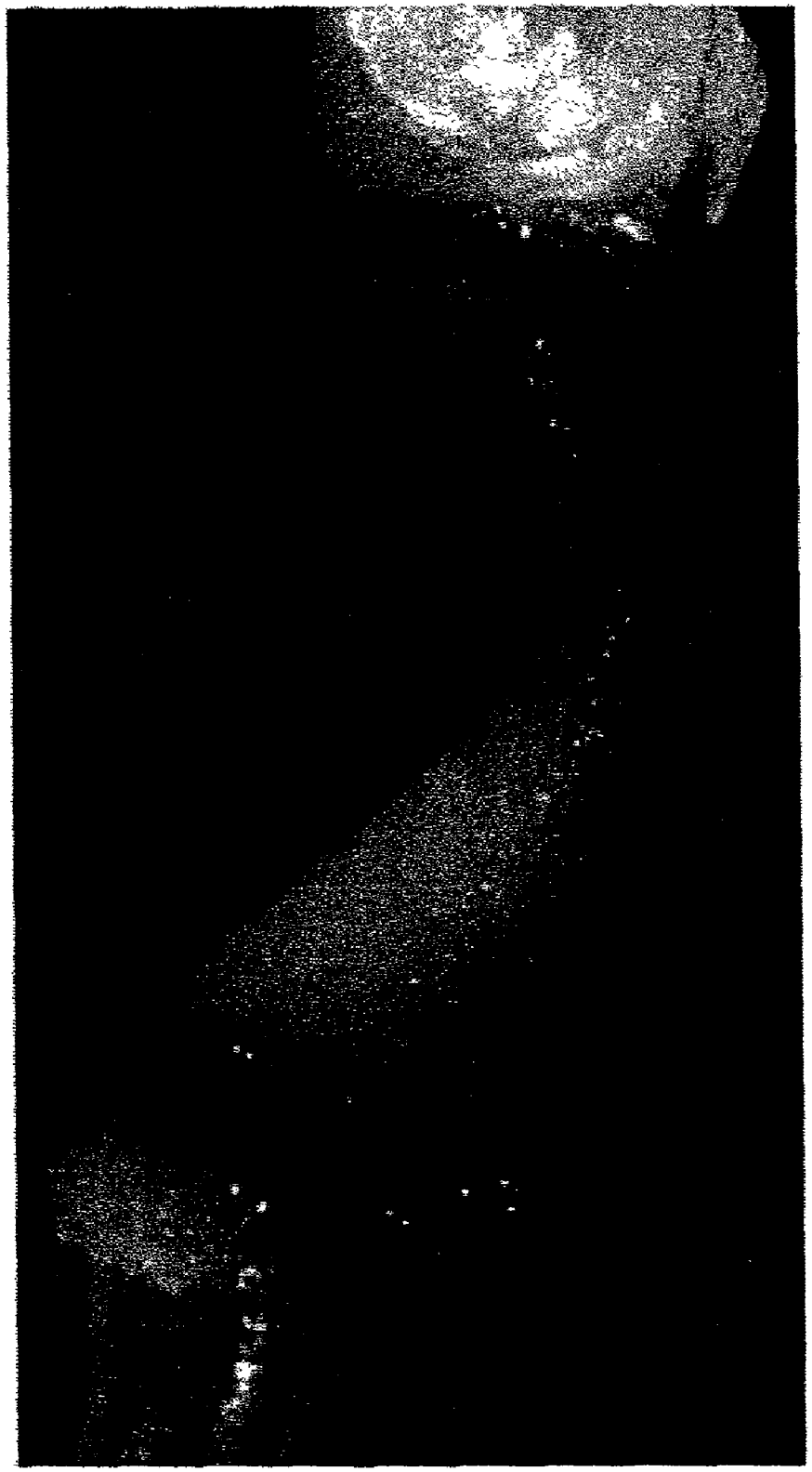
FIG. 30 depicts an embodiment of a vascular tube tested for durability and compliance.
Figure 31:
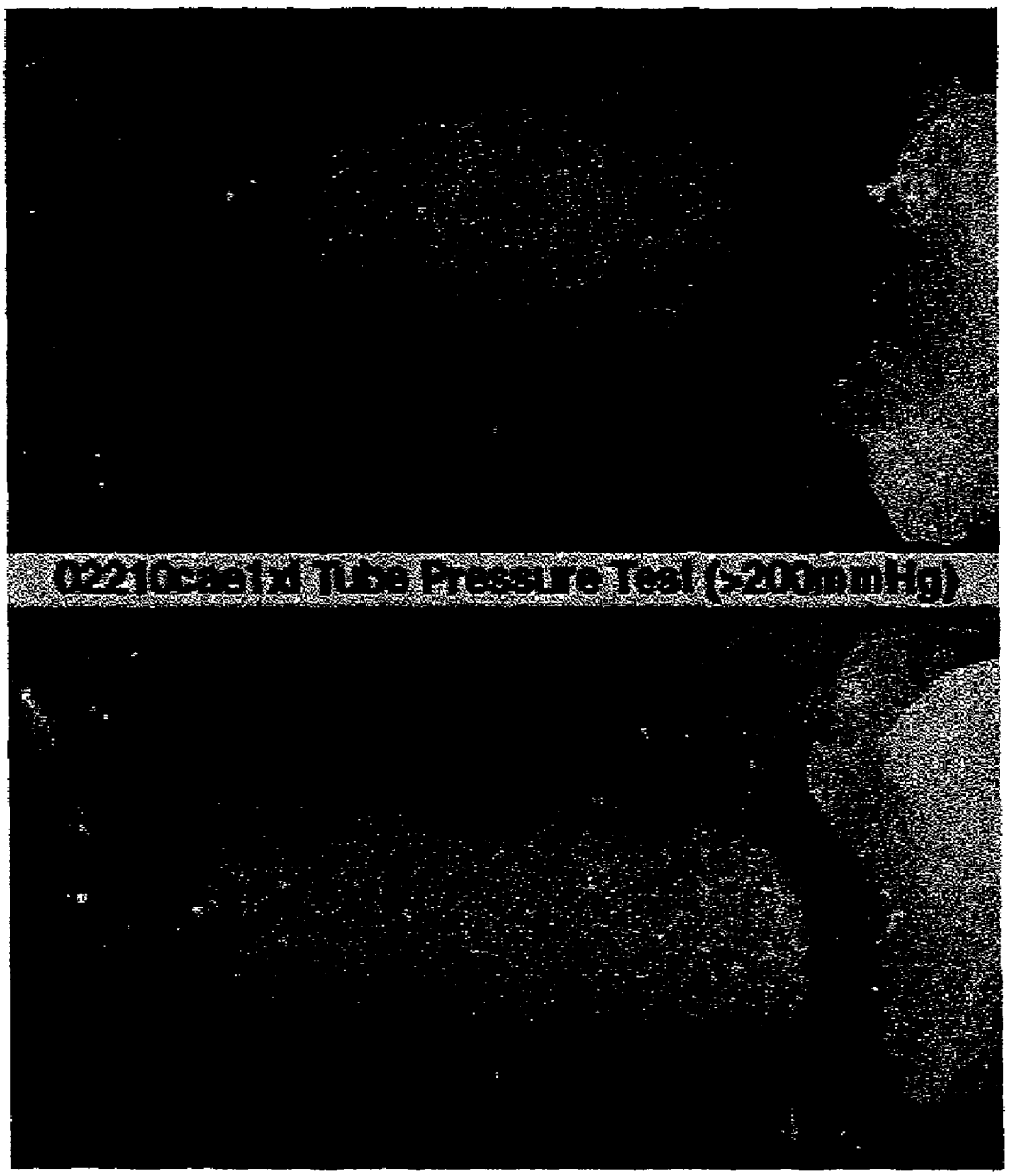
FIG. 31 depicts views of both sides of an embodiment of a vascular tube tested for hydraulic pressure.
Figure 32:
FIG. 32 depicts, at the arrows, an embodiment of a bulging vascular tube tested for pressure strength and durability.

A vascular tube was prepared as described above using a mixture of collagen:albumin:elastin (ratio 2:2:1) (pH 7.4; 2 mm inner diameter). FIG. 29 depicts an embodiment of the vascular tube. The tube was placed over polyethylene hose, tied with silk suture material and cemented with adhesive. The tube was then visually tested for durability and compliance by twisting. FIG. 30 depicts the vascular tube tested for durability and compliance. FIG. 31 depicts both sides of a vascular tube tested for hydraulic pressure. The polyethylene hose was attached to a Tygon S-50-HL class V1 hose that was attached to a peristaltic pump that circulated phosphate buffered saline (PBS) through the hose and tube at 3.5 ml/min. It was found that back pressure of over 200 mm Hg could be generated several times without damaging the vascular tube. FIG. 32 depicts, at the arrows, the vascular tube bulging in response to over 200 mm Hg back pressure. FIG. 32 also illustrates that the back pressure could have been greater, but for leakage occurring at the vascular tube and polyethylene hose junction. In similar replicate tubes, it was found that no leaking occurred after 72 hours of constant circulation of PBS fluid.

Example #26

Preparation of Poly(vinyl-alcohol)(PVA) Particles in Protein Matrix Wafers

In this study PVA super hydrolyzed (99.3% M.W. 106,000-110,000, viscosity of 4% aqueous solution 55-65 cps at 20° C.) and recombinant human epidermal growth factor (hEGF) (R&D System) were used. A 4% solution of PVA (J. T. Baker) in distilled water was dissolved 1 hour at 85° C. and added to a hEGF solution, which was dissolved into the distilled water (50 µg/ml) and dried at 40° C. at vacuum oven over night. The film was pulverized and then sieved to separate EGF-PVA particles into various groups by size. The size of final particles was 250-500 µm in diameter.

Formulation of Protein Matrix Containing Collagen

Collagen (80 mg) (Type I, calf skin) (ICN Biomedicals Inc.) was dissolved in 700 µl vitrogen and 200 µl distilled water and spread and dried entirely on glass plate until spread protein became cohesive. Once cohesive body was formed the EGF-PVA particles (6 mg) were added to the cohesive body and rolled into a cylinder and made into a protein matrix wafer form by compression molding at 2000 psi. The wafers were cross-linked for 0, 3, 15, 30, or 60 minute in a 1% glutaraldehyde solution and subsequently rinsed 3 times in a 5 ml buffer solution (PBS) for three minute each time. Then EGF-PVA particles and cross-linked and non-cross-linked matrices were sterilized 30 minute by Cesium-137 irradiation (>10K RADS).

Release Study

EGF-PVA particles, cross-linked wafers and non-cross-linked wafers were incubated on the thermal rocker at 37° C. in 1 ml of PBS or William's E medium solution. One ml samples were collected and replaced with fresh medium solution from each tube at 1, 4, 8, 24, 48, 72, 96, 120, 144, 192, 240 hour time intervals. The EGF release was monitored in vitro using a specific enzyme linked immunosorbent assay (ELISA) for both particle and matrices.

ELISA Assay

The release of hEGF was measured using ELISA. The cytokine antibody pairs were used for construction of ELISAs. The captured antibody was monoclonal anti-human EGF antibody (MAB 636)(500 µg) (R&D System) and detection antibody was biotinylated anti-human EGF antibody (BAF236) (50 µg))(R&D System). The wells of a 96-well titertek plate (Polysorb,Nunc Plasticware) were coated with monoclonal anti-human EGF antibody in PBS solution.

Figure 33:
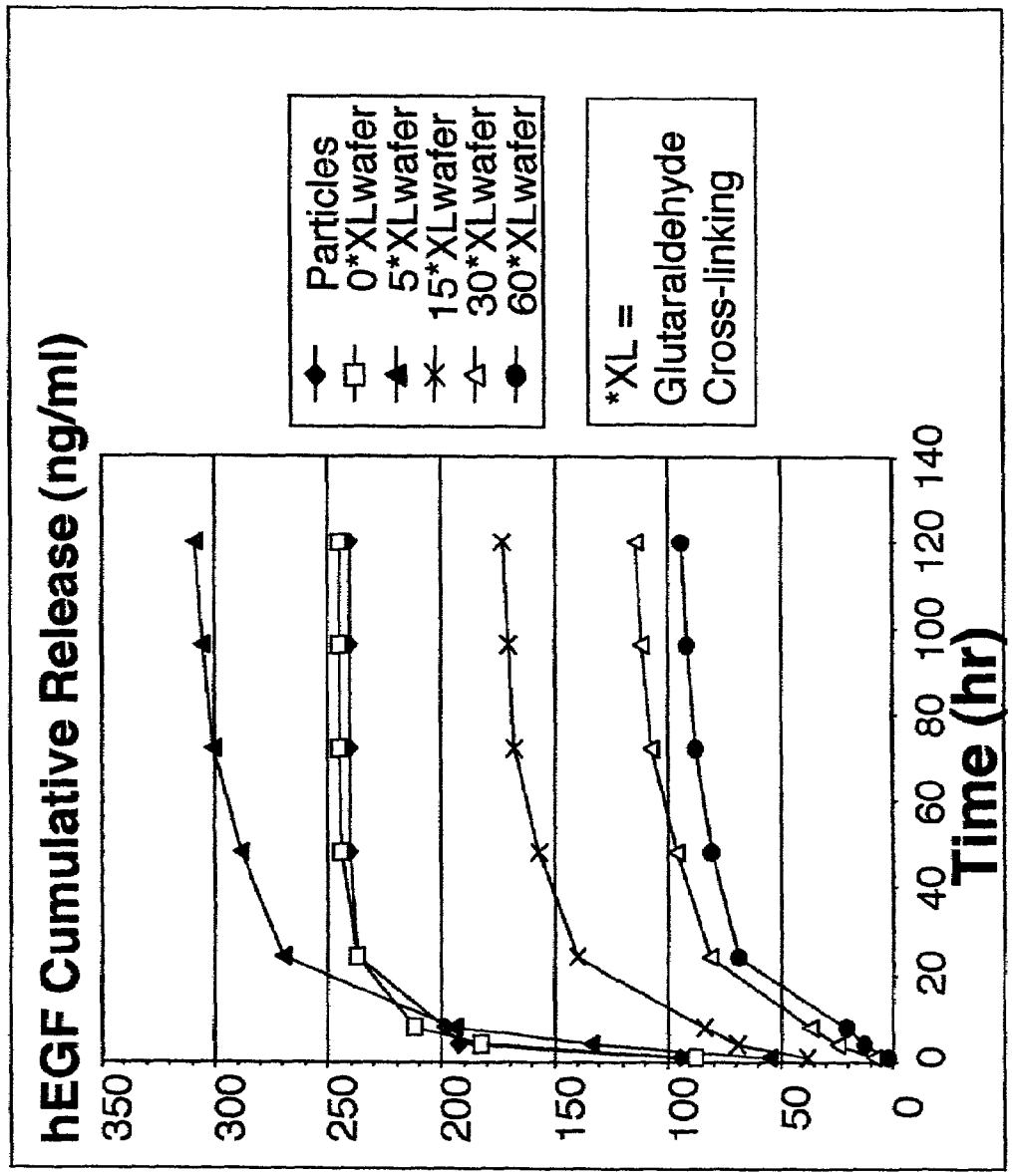
FIG. 33 depicts the results of the hEGF release study from embodiments of PVA particles used in the protein matrix wafers of the present invention.

Sample or standards were added in an appropriate diluent per well. The biotinylated detection antibody was diluted in the appropriate diluent (0.1% BSA, 0.05% Tween 20 in Tris-buffered Saline pH 7.3 (20 mM Trizma base, 150 mM NaCl), and added to each well. The plate was covered with an adhesive strip and incubated 2 hours at room temperature. Streptavidin HRP(Zymed)1/2500 of a 1.25 mg/ml solution or equivalent) was then added to each well followed by a substrate solution ($H_2O_2$) and developer ABTS (2,2'Azino-di[3-ethylbenzthiazoline-6-sulfonate]) (Boehringer-Mannheim). The assay was incubated for 20-30 minutes at 37° C. The optical density was determined for each well in the plate within 30 minutes, using microplate reader 450 nm. FIG. 33 depicts the results of the hEGF release study from the PVA particles used in the protein matrix wafers. The results of this study show that crosslinking the protein matrix decreases the release of hEGF. It was also determined from subsequent studies that the hEGF released has biological activity in in-vitro cell culture studies using hepatocytes.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

What is claimed is:

1. A solvated compressed protein matrix material, comprising one or more biocompatible protein materials, combined with one or more biocompatible solvents and optionally one or more pharmacologically active agents, wherein the protein material(s), biocompatible solvent(s) and optional pharmacologically active agent(s) are formed into a cohesive solid body having a solvent content of about 20% to 80% and not having the characteristics of cracking, shattering, breaking or being crosslinked so as to inhibit the cohesive solid body from remaining cohesive unto itself when being formed and the cohesive solid body is compressed at a pressure of about 100 psi to 100,000 psi to remove bulk biocompatible solvent and generate additional intermolecular and Intramolecular forces between one or more of the protein material(s), solvent(s) and/or pharmacologically active agent(s) to form the solvated compressed protein matrix material having a solvent content of about 10% to 60%.

2. The protein matrix material of claim 1 wherein the biocompatible proteins are selected from the group consisting of elastin, collagen, albumin, keratin, fibronectin, silk, silk fibroin, actin, myosin, fibrinogen, thrombin, aprotinin, antithrombin III, genetically engineered proteins including blocks of peptide sequences comprising groups of amino acids, collagen-heparin and collagen-chondroiten.

3. The protein matrix material of claim 1 wherein the biocompatible solvent is selected from the group consisting of water, dimethyl sulfoxide (DMSO), biocompatible alcohols, biocompatible acids, oils and biocompatible glycols.

4. The protein matrix material of claim 1 wherein the protein matrix material includes the one or more pharmacologically active agents, cells or a combination thereof.

5. The protein matrix material of claim 4 wherein the one or more pharmacologically active agents are selected from the group consisting of analgesics, anesthetics, antipsychotic agents, steroids, antisteroids, corticosteroids, antiglacoma agents, antialcohol agents, anti-coagulants agents, genetic material, antitbrombolytic agents, anticancer agents, anti-Parkinson agents, antiepileptic agents, anti-inflammatory agents, anticonception agents, enzymes agents, growth factors, antiviral agents, antibacterial agents, antifungal agents, hypoglycemic agents, antihistamine agents, chemoattractants, neutraceuticals, antiobesity, smoking cessation agents, obstetric agents, antimicrobial agents, glycosaminoglycans, cancer agents, and antiasmatic agents.

6. The protein matrix material of claim 4, wherein the pharmacologically active agent comprises a second, migration-vulnerable drug delivery device.

7. The protein matrix material of claim 4 wherein the one or more pharmacologically active agents are included in the amount of 0.001% to 200% based upon the weight of the biocomipatible protein material.

8. The protein matrix material of claim 1 further comprising one or more biocompatible polymeric materials.

9. The protein matrix material of claim 8 wherein the one or more biocompatible polymeric materials are selected from the group consisting of epoxies, polyesters, acrylics, nylons, silicones, polyanhydride, polyurethane, polycarbonate, poly (tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid polymers, polyvinyl alcohol, 2-hydroxyethyl methacrylate polymers, polymethyl methacrylate, 1,3-bis(carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl-based polymers, isopropyl styrene polymers, vinyl pyrrolidone polymers, cellulose acetate dibutyrate polymers, silicone rubber, and copolymers and combinations of these.

10. The protein matrix material of claim 1 wherein all or a portion of the protein matrix material is crosslinked with one or more crosslinking agents.

11. The protein matrix material of claim 10 wherein the one or more crosslinking reagents are selected from the group consisting of glutaraldehyde, p-Azidobenzolyl Hydazide, N-5-Azido 2-nitrobenzoyloxysuccinimide, N-Succinimidyl 6-[4'azido-2'-nitro-phenylamino]hexanoate and 4-[p-Azidosalicylamido] butylamine.

12. The protein matrix material of claim 10, wherein the matrix material is imprinted by crosslinking in a predetermined pattern utilizing crosslinking reagents and masking or strategically positioned UV light activated reagents.

13. The protein matrix material of claim 1 wherein the protein matrix material is produced in a form selected from the group consisting of cylinders, threads, strips, tubes, particles, sheets and wafers.

14. The protein matrix material of claim 1 wherein the biocompatible protein materials are collagen and elastin.

15. The protein matrix material of claim 1 wherein the protein matrix material inculdes one or more additives in the amount of 0% to 300% based upon the weight of the biocotlipatible protein material.

16. A method of making a protein matrix material, comprising the steps of:

(a) preparing a coatable composition comprising one or more biocompatible protein materials and one or more biocompatible solvents;

(b) coating the composition to form a film;

(c) partially drying the coated film until the coated film can be formed into a cohesive solid body;

(d) forming said cohesive solid body having a solvent content of about 20% to 80% and not having the characteristics of cracking, shattering, breaking or being crosslinked so as to inhibit the cohesive solid body from remaining cohesive unto itself when being formed; and (e) compressing the cohesive solid body at a pressure of about 100 psi to 100,000 psi to remove bulk biocompatible solvent to form a solvated protein matrix material having a solvent content of about 10% to 60%.

17. The method of making a protein matrix material of claim 16 wherein the biocompatible proteins are selected from the group consisting of elastin, collagen, albumin, keratin, fibronectin, silk, silk fibroin, actin, myosin, fibrinogen, thrombin, aprotinin, antithrombin III, genetically engineered proteins including blocks of peptide sequences comprising groups of amino acids, collagen-heparin and collagen-chondroiten.

18. The method of making a protein matrix material of claim 16 wherein the biocompatible solvent is selected from the group consisting of water, dimethyl sulfoxide (DMSO), biocompatible alcohols, biocompatible acids, oils and biocompatible glycols.

19. The method of making a protein matrix material of claim 16, wherein the protein matrix material further includes one or more pharmacologically active agents, cells or a combination thereof.

20. The method of making a protein matrix material of claim 19 wherein the one or more pharmacologically active agents are selected from the group consisting of analgesics, anesthetics, antipsychotic agents, steroids, antisteroids, corticosteroids, antiglacoma agents, antialcohol agents, anti-coagulants agents, genetic material, antithrombolytic agents, anticancer agents, anti Parkinson agents, antiepileptic agents, anti-inflammatory agents, anticonception agents, enzymes agents, growth factors, antiviral agents, antibacterial agents, antifungal agents, hypoglycemic agents, antihistamine agents, chemoattractants, neutraceuticals, antiobesity, smoking cessation agents, obstetric agents, antimicrobial agents, glycosaminoglycans, cancer agents, and antiasmatic agents.

21. The method of making a protein matrix material of claim 19, wherein the pharmacologically active agent comprises a second, migration-vulnerable drug delivery device.

22. The method of making a protein matrix material of claim 16 further comprising one or more biocompatible polymeric materials.

23. The method of making a protein matrix material of claim 16 wherein the one or more biocompatible polymeric materials are selected from the group consisting of epoxies, polyesters, acrylics, nylons, silicones, polyanhydride, polyurethane, polycarbonate, poly(tetrafluoroethylene), polycaprolactone, polyethylene oxide, polyethylene glycol, poly (vinyl chloride), polylactic acid, polyglycolic acid, polypropylene oxide, poly(akylene)glycol, polyoxyethylene, sebacic acid polymers, polyvinyl alcohol, 2 hydroxyethyl methacrylate polymers, polymethyl methacrylate, 1,3 bis (carboxyphenoxy)propane polymers, lipids, phosphatidyicholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl based polymers, isopropyl styrene polymers, vinyl pyrrolidone polymers, cellulose acetate dibutyrate polymers, silicone rubber, and copolymers and combinations of these.

24. The method of making a protein matrix material of claim 16 further comprising the step of crosslinking all or a portion of the protein matrix material with one or more suitable crosslinking agents.

25. The method of making a protein matrix material of claim 16 further comprising the step of processing the protein matrix material into a particulate form.

26. The method of making a protein matrix material of claim 16 further comprising the step of adjoining two or more protein matrix materials to form a multi-layer protein matrix material.

27. A method of making a wound healing device, comprising the steps of:
(a) preparing a coatable composition comprising one or more biocompatible protein materials and one or more biocompatible solvents;
(b) coating the composition to form a film;
(c) partially drying the coated film until the coated film can be formed into a cohesive solid body having a surface area less than that of the film;
(d) forming said cohesive solid body having a solvent content of about 20% to 80% and not having the characteristics of cracking, shattering, breaking or being crosslinked so as to inhibit the cohesive solid body from remaining cohesive unto itself when being formed; and
(e) compressing the cohesive solid body at a pressure of about 100 psi to 100,000 psi to remove bulk biocompatible solvent to form a solvated wound healing device having a solvent content of about 10% to 60%.

28. The method of making a wound healing device of claim 27 wherein the biocompatible proteins are selected from the group consisting of elastin, collagen, albumin, keratin, fibronectin, silk, silk fibroin, actin, myosin, fibrinogen, thrombin, aprotinin, antithrombin III, genetically engineered proteins including blocks of peptide sequences comprising groups of amino acids, collagen-heparin and collagen-chondroiten.

29. The method of making a wound healing device of claim 27 wherein the biocompatible solvent is selected from the group consisting of water, dimethyl sulfoxide (DMSO), biocompatible alcohols, biocompatible acids, oils and biocompatible glycols.

30. The method of making a wound healing device of claim 27, wherein the wound dealing device further includes one or more pharmacologically active agents, cells or a combination thereof.

31. The method of making a wound healing device of claim 30 wherein the one or more pharmacologically active agents are selected from the group consisting of analgesics, anesthetics, antipsychotic agents, steroids, antisteroids, corticosteroids, antiglacoma agents, antialcohol agents, anti-coagulants agents, genetic material, antithrombolytic agents, anticancer agents, anti Parkinson agents, antiepileptic agents, anti-inflammatory agents, anticonception agent , enzymes agents, growth factors, antiviral agents, antibacterial agents, antifungal agents, hypoglycemic agents, antihistamine agents, chemoattractants, neutraceuticals, antiobesity, smoking cessation agents, obstetric agents, antimicrobial agents, glycosaminoglycans, cancer agents, and antiasmatic agents.

32. The method of making a wound healing device of claim 30, wherein the pharmacologically active agent comprises a second, migration-vulnerable drug delivery device.

33. The method of making a wound healing device of claim 27 further comprising one or m re biocompatible polymeric materials.

34. The method of making a wound healing device of claim 33 wherein the one or more biocompatible polymeric materials are selected from the group consisting of epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid polymers, polyvinyl alcohol, 2 hydroxyethyl methacrylate polymers, polymethyl methacrylate, 1,3 bis (carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl based polymers, isopropyl styrene polymers, vinyl pyrrolidone polymers, cellulose acetate dibutyrate polymers, silicone rubber, and copolymers and combinations of these.

35. The method of making a wound healing device of claim 27 further comprising the step of crosslinking all or a portion of the wound healing device with one or more suitable crosslinking agents.

36. The method of making a wound healing device of claim 27 further comprising the step of processing the wound healing device into particles.

37. The method of making a wound healing device of claim 27 further comprising the step of adjoining two or more wound healing devices to form a multi-layer wound healing device.

38. A method of delivery of one or more pharmacologically active agents, cells or a combination thereof comprising:
providing a drug delivery device comprising one or more biocompatible protein materials, combined with one or more biocompatible solvents and one or more pharmacologically active agents, cells or combinations thereof, wherein the protein material(s), biocompatible solvent(s) and pharmacologically active agent(s), cells or combinations thereof are formed into a cohesive solid body having a solvent content of about 20% to 80% and not having the characteristics of cracking, shattering, breaking or being crosslinked so as to inhibit the cohesive solid body from remaining cohesive unto itself when being formed and the cohesive solid body is compressed at a pressure of about 100 psi to 100,000 psi to remove bulk biocompatible solvent and generate additional intermolecular and intramolecular forces between one or more of the protein material(s), solvent(s) and/or pharmacologically active agent(s) to form the drug delivery device having a solvent content of about 10% to 60%; and
administering the drug delivery device to a patient.

39. The method of delivery of one or more pharmacologically active agents of claim 38 wherein the biocompatible proteins are selected from the group consisting of elastin, collagen, albumin, keratin, fibronectin, silk, silk fibroin, actin, myosin, fibrinogen, thrombin, aprotin in, antithrombin III, genetically engineered proteins including blocks of peptide sequences comprising groups of amino acids, collagen-heparin and collagen-chondroiten.

40. The method of delivery of one or more pharmacologically active agents of claim 38 wherein the biocompatible solvent is selected from the group consisting of water, dimethyl sulfoxide (DMSO), biocompatible alcohols, biocompatible acids, oils and biocompatible glycols.

41. The method of delivery of one or more pharmacologically active agents of claim 38 wherein the one or more pharmacologically active agents are selected from the group consisting of analgesics, anesthetics, antipsychotic agents, steroids, antisteroids, corticosteroids, antiglacoma agents, antialcohol agents, anti-coagulants agents, genetic material, antithrombolytic agents, anticancer agents, anti-Parkinson agents, antiepileptic agents, anti-inflammatory agents, anticonception agents, enzymes agents, growth factors, antiviral agents, antibacterial agents, antifungal agents, hypoglycemic agents, antihistamine agents, chemoattractants, neutraceuticals, antiobesity, smoking cessation agents, obstetric agents, antimicrobial agents, glycosaminoglycans, cancer agents, and antiasmatic agents.

42. The method of delivery of one or more pharmacologically active agents of claim 38 wherein the pharmacologically active agent comprises a second, migration-vulnerable drug delivery device.

43. The method of delivery of one or more pharmacologically active agents of claim 38 further comprising one or more biocompatible polymeric materials.

44. The method of delivery of one or more pharmacologically active agents of claim 43 wherein the one or more biocompatible polymeric materials are selected from the group consisting of epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid polymers, polyvinyl alcohol, 2 hydroxyethyl methacrylate polymers, polymethyl methacrylate, 1,3 bis(carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl based polymers, isopropyl styrene polymers, vinyl pyrrolidone polymers, cellulose accetate dibutyrate polymers, silicone rubber, and copolymers and combinations of these.

45. The method of delivery of one or more pharmacologically active agents of claim 38 wherein all or a portion of the drug delivery device is crosslinked with one or more crosslinking agents.

46. The method of delivery of one or more pharmacologically active agents of claim 45 wherein the one or more cross linking reagents are selected from the group consisting of glutaraldehyde, p-Azidobenzolyl Hydazide, N-5-Azido 2-nitrobenzoyloxysuccinimide, N-Succinimidyl 6-[4'azido-2'nitro-phenylamino]hexanoate and 4-[p-Azidosalicylamido]butylamine.

47. The method of delivery of one or more pharmacologically active agents of claim 38 wherein the drug delivery device is produced in a form selected from the group consisting of cylinders, tubes, particles, sheets, wafers and patches.

48. The method of delivery of one or more pharmacologically active agents of claim 38 wherein the drug delivery device includes two or more layers of at least one protein matrix material.

49. The method of delivery of one or more pharmacologically active agents of claim 38 further comprising a release mechanism that releases the pharmacologically active agent upon contact with an outside stimuli.

50. The method of delivery of one or more pharmacologically active agents of claim 38 wherein the biocompatible protein materials are collagen and elastin.

51. The method of delivery of one or more pharmacologically active agents of claim 38 wherein the protein matrix material includes one or more additives in the amount of 0% to 300% based upon the weight of the biocompatible protein material.

52. The method of delivery of one or more pharmacologically active agents of claim 38 wherein the one or more pharmacologically active agents are included in the amount of 0.001% to 200% based upon the weight of the biocompatible protein material.

53. A method of treating a wound comprising:

providing a wound healing device comprising one or more biocompatible protein materials, combined with one or more biocompatible solvents and one or more pharmacologically active agents, cells or combinations thereof, wherein the protein material(s), biocompatible solvent(s) and pharmacologically active agent(s), cells or combinations thereof are formed into a cohesive solid body having a solvent content of about 20% to 80% and not having the characteristics of cracking, shattering, breaking or being crosslinked so as to inhibit the cohesive solid body from remaining cohesive unto itself when being formed and the cohesive solid body is compressed at a pressure of about 100 psi to 100,000 psi to remove bulk biocompatible solvent and generate additional intermolecular and intramolecular forces between one or more of the protein material(s), solvent(s) and/or pharmacologically active agent(s) to form the wound healing device having a solvent content of about 10% to 60%; and administering the wound healing device to a wound.

54. The method of treating a wound of claim 53 comprising wherein the biocompatible proteins are selected from the group consisting of elastin, collagen, albumin, keratin, fibronectin, silk, silk fibroin, actin, myosin, fibrinogen, thrombin, aprotinin, antithrombin III, genetically engineered proteins including blocks of peptide sequences comprising groups of amino acids, collagen-heparin and collagen-chondroiten.

55. The method of treating a wound of claim 53 wherein the biocompatible solvent is selected from the group consisting of water, dimethyl sulfoxide (DMSO), biocompatible alcohols, biocompatible acids, oils and biocompatible glycols.

56. The method of treating a wound of claim 53 further comprising one or more pharmacologically active agents, cells or a combination thereof.

57. The method of treating a wound of claim 56 wherein the one or more pharmacologically active agents are selected from the group consisting of analgesics, anesthetics, antipsychotic agents, steroids, antisteroids, corticosteroids, antiglacoma agents, antialcohol agents, anti-coagulants agents, genetic material, antithrombolytic agents, anticancer agents, anti-Parkinson agents, antiepileptic agents, anti-inflammatory agents, anticonception agents, enzymes agents, growth factors, antiviral agents, antibacterial agents, antifungal agents, hypoglycemic agents, antihistamine agents, chemoattractants, neutraceuticals, antiobesity, smoking cessation agents, obstetric agents, antimicrobial agents, glycosaminoglycans, cancer agents, and antiasmatic agents.

58. The method of treating a wound of claim 53 wherein the pharmacologically active agent comprises a second, migration-vulnerable drug delivery device.

59. The method of treating a wound of claim 53 further comprising one or more biocompatible polymeric materials.

60. The method of treating a wound of claim 59 wherein the one or more biocompatible polymeric materials are selected from the group consisting of epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid polymers, polyvinyl alcohol, 2 hydroxyethyl methacrylate polymers, polymethyl methacrylate, 1,3 bis(carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl based polymers, isopropyl styrene polymers, vinyl pyrrolidone polymers, cellulose acetate dibutyrate polymers, silicone rubber, and copolymers and combinations of these.

61. The method of treating a wound of claim 53 wherein all or a portion of the wound healing device is crosslinked with one or more crosslinking agents.

62. The method of treating a wound of claim 53 wherein the wound healing device is selected from the group consisting of bone inserts, meshes, strips, sutures, dental plugs, skin dressings, bandages, tissue plugs, vertebrae inserts, vertebral discs, joints, bronchial tissue inserts, abdominal inserts, vascular inserts, particles, biological fasteners, staples, hemostats and port seals.

63. The method of treating a wound of claim 62 wherein the bandage comprises a segment of protein matrix material positioned on a non-adhesive strip adjoined to adhesive ends.

64. The method of treating a wound of claim 62 wherein the wound healing device includes a patch delivery system adjoined behind the protein matrix dressing for delivery of additional pharmacologically active agents.

65. The method of treating a wound of claim 53 wherein the wound healing device includes two or more layers of at least one protein matrix material.

66. The method of treating a wound of claim 53 wherein the biocompatible protein materials are collagen and elastin.

* * * * *

UNITED STATES PATENT AND TRADEMARK OFFICE
CERTIFICATE OF CORRECTION

PATENT NO. : 7,662,409 B2
APPLICATION NO. : 09/796170
DATED : February 16, 2010
INVENTOR(S) : David B. Masters It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this

Twenty-eighth Day of December, 2010

David J. Kappos
*Director of the United States Patent and Trademark Office*